(12) United States Patent
Roux et al.

(10) Patent No.: US 12,227,767 B2
(45) Date of Patent: Feb. 18, 2025

(54) DELTA133P53BETA AND DELTA133P53GAMMA ISOFORMS ARE BIOMARKERS OF CANCER STEM CELLS

(71) Applicants: Centre National de la Recherche Scientifique (CNRS), Paris (FR); Universite de Montpellier, Montpellier (FR)

(72) Inventors: Pierre Roux, Saint Gely-du Fesc (FR); Nikola Arsic, Montpellier (FR); Gilles Gadea, Les Matelles (FR); Philippe Fort, Castelnau-le-Lez (FR); Fanny Tomas, Montpellier (FR); Véronique Gire, Montpellier (FR)

(73) Assignees: Centre National de la Recherche Scientifique (CNRS), Paris (FR); Universite de Montpellier, Montpellier (FR)

( * ) Notice: Subject to any disclaimer, the term of this patent is extended or adjusted under 35 U.S.C. 154(b) by 670 days.

(21) Appl. No.: 17/166,004

(22) Filed: Feb. 3, 2021

(65) Prior Publication Data

US 2021/0214691 A1 Jul. 15, 2021

Related U.S. Application Data

(63) Continuation of application No. 15/547,211, filed as application No. PCT/EP2016/052095 on Feb. 1, 2016, now Pat. No. 10,920,198.

(30) Foreign Application Priority Data

Jan. 30, 2015 (EP) .................................... 15305146

(51) Int. Cl.
| | | |
|---|---|---|
| C12Q 1/68 | (2018.01) |
| A61K 31/704 | (2006.01) |
| A61K 31/7048 | (2006.01) |
| C07K 14/47 | (2006.01) |
| C12N 5/095 | (2010.01) |
| C12Q 1/6886 | (2018.01) |
| G01N 33/50 | (2006.01) |
| G01N 33/574 | (2006.01) |

(52) U.S. Cl.
CPC .......... *C12N 5/0695* (2013.01); *A61K 31/704* (2013.01); *A61K 31/7048* (2013.01); *C07K 14/4746* (2013.01); *C12Q 1/6886* (2013.01); *G01N 33/5011* (2013.01); *G01N 33/5073* (2013.01); *G01N 33/57484* (2013.01); *C12N 2501/998* (2013.01); *C12N 2503/00* (2013.01); *C12N 2506/30* (2013.01); *C12N 2510/00* (2013.01); *C12Q 2600/106* (2013.01); *C12Q 2600/118* (2013.01); *C12Q 2600/156* (2013.01); *G01N 2333/4748* (2013.01); *G01N 2500/10* (2013.01)

(58) Field of Classification Search
None
See application file for complete search history.

(56) References Cited

U.S. PATENT DOCUMENTS

2008/0293056 A1 11/2008 Kondo

FOREIGN PATENT DOCUMENTS

| EP | 2272979 A1 | 1/2011 |
| JP | 2008263824 A | 11/2008 |
| JP | 2012531606 A | 12/2012 |
| JP | 2014-224085 A | 12/2014 |
| WO | 2009/029054 A1 | 3/2009 |
| WO | 2010/143168 A2 | 12/2010 |
| WO | 2011000891 A1 | 1/2011 |
| WO | 2011148983 A1 | 12/2011 |
| WO | 2012/044979 A2 | 4/2012 |

OTHER PUBLICATIONS

Milicevic, Z. et al., Identification of p53 and its Isoforms in Human Breast Carcinoma Cells, The Scientific World Journal, 2014, vol. 11, No. 4, pp. 1-10.
Mizuno, H. et al., Inactivation of p53 in breast cancers correlates with stem cell transcriptional signatures, Proceedings of the National Academy of Sciences, 2010, vol. 107, No. 52, pp. 22745-22750.
Machado-Silva, A. et al., p53 family members in cancer diagnosis and treatment, Seminars in Cancer Biology, 2010, vol. 20, No. 1, pp. 57-62.
Anensen N, Oyan AM, Bourdon JC et al. (2006) A distinct p53 protein isoform signature reflects the onset of Induction chemotherapy for acute myeloid leukemia. Clin Cancer Res 12:3985-92.
Avery-Kiejda, K.A., Morten, B., Wong-Brown, M.W., Mathe, A., and Scott, R.J. (2014). The relative mRNA expression of p53 isoforms in breast cancer is associated with clinical features and outcome. Carcinogenesis 35, 586-596.
Bernard H, Garmy-Susini B, Ainaoui N, Van Den Berghe L, Peurichard A, Javerzat S, Bikfalvi A, Lane DP, Bourdon JC, Prats AC. (2013) The p53 isoform, ?133p53?, stimulates angiogenesis and tumour progression. Oncogene. Apr. 25, 2013;32(17):2150-60.
Bieging, K.T., Mello, S.S., and Attardi, L.D. (2014). Unravelling mechanisms of p53-mediated tumour suppression. Nature reviews Cancer 14, 359-370.

(Continued)

*Primary Examiner* — Celine X Qian
(74) *Attorney, Agent, or Firm* — Banner & Witcoff, Ltd.

(57) ABSTRACT

The present invention is in the field of oncology, and more particularly of cancer stem cells. It relates to a method for producing cancer stem cells based on overexpression of Δ133p53β isoform, Δ133p53γ isoform, or both Δ133p53β and Δ133p53γ isoforms; a method for predicting the risk that treatment with a chemotherapeutic anti-cancer agent induces cancer stem cells in a subject suffering from cancer from a cancer sample of said subject, based on detection of an increase in Δ133p53β isoform, Δ133p53γ isoform, or both Δ133p53β and Δ133p53γ isoforms following chemotherapeutic anti-cancer treatment; to therapeutic uses of a combination of chemotherapeutic anti-cancer agent and an agent reducing Δ133p53β isoform, Δ133p53γ isoform, or both Δ133p53β and Δ133p53γ isoforms expression; and also to screening methods for anti-cancer stem cells agents.

11 Claims, 17 Drawing Sheets

Specification includes a Sequence Listing.

(56) References Cited

OTHER PUBLICATIONS

Boldrup, L., Bourdon, J.C., Coates, P.J., Sjostrom, B., and Nylander, K. (2007). Expression of p53 isoforms in squamous cell carcinoma of the head and neck. European journal of cancer 43, 617-623.

Bourdon, J.C., Fernandes, K., Murray-Zmijewski, F., Liu, G., Diot, A., Xirodimas, D.P., Saville, M.K., and Lane, D.P. (2005). p53 isoforms can regulate p53 transcriptional activity. Genes & development 19, 2122-2137.

Bourdon, J.C. (2007). p53 and its isoforms in cancer. Br J Cancer 97, 277-282.

Bourdon, J.C., Khoury, M.P., Diot, A., Baker, L., Fernandes, K., Aoubala, M., Quinlan, P., Purdie, C.A., Jordan, L.B. Prats, A.C., et al. (2011). p53 mutant breast cancer patients expressing p53gamma have as good a prognosis as wild-type p53 breast cancer patients. Breast cancer research : BCR 13, R7.

Charras G.T. (2008). A short history of blebbing. Journal of Microscopy, vol. 231. Pt 3 pp. 446-478.

Cheng L., Ramesh A. V., Flesken-Nikitin A., Choi J., Nikitin A. Y. (2010) Mouse models for cancer stem cell research. Toxicologic Pathology. 2010;38(1):62-71.

Chiou S-H., Wang M-L., Chou Y-T., Chen C-J;, Hong C-F., Hsieh W-J., Chang H-T., Chen Y-S., Lin T-W., Hsu H-S., Wu C-W. (2010) Coexpression of Oct4 and Nanog Enhances Malignancy in Lung Adenocarcinoma by Inducing Cancer Stem Cell-Like Properties and Epithelial Mesenchymal Transdifferentiation. Cancer Res; 70(24) Dec. 15.

Davidson, W.R., Kari, C., Ren, Q., Daroczi, B., Dicker, A.P., and Rodeck, U. Differential regulation of p53 function by the N-terminal DeltaNp53 and Delta113p53 isoforms in zebrafish embryos. BMC Dev Biol 10, 102.

Fujita, K., Mondal, A.M., Horikawa, I., Nguyen, G.H., Kumamoto, K., Sohn, J.J., Bowman, E.D., Mathe, E.A., Schetter, A.J., Pine, S.R., et al. (2009). p53 isoforms Delta133p53 and p53beta are endogenous regulators of replicative cellular senescence. Nat Cell Biol 11, 1135-1142.

Gadea, G., de Toledo, M., Anguille, C., and Roux, P. (2007a). Loss of p53 promotes RhoA-ROCK-dependent cell migration and invasion in 3D matrices. J Cell Biol 178, 23-30.

Gadea, G., de Toledo, M., Anguille, C., and Roux, P. (2007b). Loss of p53 promotes RhoA-ROCK-dependent cell migration and invasion in 3D matrices. The Journal of cell biology 178, 23-30.

Gavert N, Vivanti A, Hazin J, Brabletz T, Ben-Ze'ev A. L1-mediated colon cancer cell metastasis does not require changes in EMT and cancer stem cell markers. Mol Cancer Res. Jan. 2011;9(1): 14-24.

Golebiewska A, Brons NH, Bjerkvig R, Niclou SP. Critical appraisal of the side population assay in stem cell and cancer stem cell research. Cell Stem Cell. Feb. 4, 2011;8(2):136-47.

Grez, M., et al. (1990). Embryonic stem cell virus, a recombinant murine retrovirus with expression in embryonic stem cells. Proc. Natl. Acad. Sci. USA 87:9202-9206.

Hafsi, H., Santos Silva, D., Courtois-Cox, S., and Hainaut, P. (2013). Effects of Delta40p53, an isoform of p53 lacking the N-terminus, on transactivation capacity of the tumor suppressor protein p53. BMC cancer 13, 134.

Hofstetter, G., Berger, A., Berger, R., Zoric, A., Braicu, E.I., Reimer, D., Fiegl, H., Marth, C., Zeimet, A.G., Ulmer, H., et al. (2012). The N-terminally truncated p53 isoform Delta40p53 influences prognosis in mucinous ovarian cancer. International journal of gynecological cancer : official journal of the International Gynecological Cancer Society 22, 372-379.

Hong, H., Takahashi, K., Ichisaka, T., Aoi, T., Kanagawa, O., Nakagawa, M., Okita, K., and Yamanaka, S. (2009). Suppression of induced pluripotent stem cell generation by the p53-p21 pathway. Nature 460, 1132-1135.

Jeter CR., Liu B., Liu X., Chen X., Liu C., Calhoun-Davis T., Repass J., Zaehres H., Shen JJ., Tang DG., (2011). NANOG promotes cancer stem cells characteristics and prostate cancer resistance to androgen deprivation. Oncogene 30, 3833-3845.

Kawamura, T., Suzuki, J., Wang, Y.V., Menendez, S., Morera, L.B., Raya, A., Wahl, G.M., and Izpisua Belmonte, J. C. (2009). Linking the p53 tumour suppressor pathway to somatic cell reprogramming. Nature 460, 1140-1144.

Khoury, M.P., and Bourdon, J.C. (2011). p53 Isoforms: An Intracellular Microprocessor? Genes & cancer 2, 453-465.

Lane, D.P. (1992). Cancer. p53, guardian of the genome. Nature 358, 15-16.

Li, M., He, Y., Dubois, W., Wu, X., Shi, J., and Huang, J. (2012). Distinct regulatory mechanisms and functions for p53-activated and p53-repressed DNA damage response genes in embryonic stem cells. Mol Cell 46, 30-42.

Liu, Y., Dong, Q.Z., Zhao, Y., Dong, X.J., Miao, Y., Dai, S.D., Yang, Z.Q., Zhang, D., Wang, Y., Li, Q.C., et al. (2009). P120-catenin isoforms 1A and 3A differently affect invasion and proliferation of lung cancer cells. Exp Cell Res 315, 890-898.

Mavroudis D. Circulating cancer cells. Ann Oncol. Oct. 2010;21 Suppl 7:vii95-100.

Miller, A. D. & Rosman, G. J. (1989). Improved retroviral vectors for gene transfer and expression. BioTechniques 7:980-990.Muller, P.A., Caswell, P.T., Doyle, B., Iwanicki, M.P., Tan, E.H., Karim, S., Lukashchuk, N., Gillespie, D.A., Ludwig, R.L., Gosselin, P., et al. (2009). Mutant p53 drives invasion by promoting integrin recycling. Cell 139, 1327-1341.

Norikatsu Miyoshi, Hideshi Ishiia, b, 1, Ken-ichi Nagaia, Hiromitsu Hoshinoa, Koshi Mimorib, Fumiaki Tanakab, Hiroaki Naganoa, Mitsugu Sekimotoa, Yuichiro Dokia, and Masaki Mori. (2010). Defined factors induce reprogramming of gastrointestinal cancer cells. 40-45 | PNAS vol. 107 | No. 1.

Oshima N., Yamada Y., Nagayama S., Kawada K., Hasegawa S., Okabe H., Sakai Y., TAoi T. (2014). Induction of Cancer Stem Cell Properties in Colon CancerCells by Defined Factors. PLOS ONE | www.plosone.org, vol. 9 | Issue 7 | e101735.

Roger, L., Jullien, L., Gire, V., and Roux, P. (2010). Gain of oncogenic function of p53 mutants regulates E-cadherin expression . uncoupled from cell invasion in colon cancer cells. Journal of cell science 123, 1295-1305.

Sarig, R., Rivlin, N., Brosh, R., Bornstein, C., Kamer, I., Ezra, O., Molchadsky, A., Goldfinger, N., Brenner, O., and Rotter, V. (2010). Mutant p53 facilitates somatic cell reprogramming and augments the malignant potential of reprogrammed cells. J Exp Med 207, 2127-2140.

Schatton T, Frank NY, Frank MH. (2009) Identification and targeting of cancer stem cells. BioEssays: news and reviews in molecular, cellular and developmental biology. Oct. 2009;31(10):1038-49.

Takahashi, R., Markovic, S.N., and Scrable, H.J. (2014). Dominant effects of Delta40p53 on p53 function and melanoma cell fate. The Journal of investigative dermatology 134, 791-800.

Tirino V, Desiderio V, Paino F, De Rosa A, Papaccio F, La Noce M, Laino L, De Francesco F, Papaccio G. Cancer stem cells in solid tumors: an overview and new approaches for their isolation and characterization. FASEB J. Jan. 2013;27(1):13-24.

Utikal, J., Polo, J.M., Stadtfeld, M., Maherali, N., Kulalert, W., Walsh, R.M., Khalil, A., Rheinwald, J.G., and Hochedlinger, K. (2009). Immortalization eliminates a roadblock during cellular reprogramming into iPS cells. Nature 460, 1145-1148.

Vinot, S., Anguille, C., de Toledo, M., Gadea, G., and Roux, P. (2008). Analysis of cell migration and its regulation by Rho GTPases and p53 in a three-dimensional environment. Methods Enzymol 439, 413-424.

Zhao, T., and Xu, Y. (2010). p53 and stem cells: new developments and new concerns. Trends Cell Biol 20, 170-175.

Yoon et al. "A novel carbazole derivative, MHY407, sensitizes cancer cells to doxorubicin-, etoposide-, and radiation treatment via DNA damage". European Journal of Pharmacology 697 (2012) 24-31.

Liu et al. "Chemotherapy targeting cancer stem cells". Am J Cancer Res 2015; 5(3):880-893.

Senapati et al. "Promising approaches os small interfering RNAs (siRNAs) mediated cancer gene therapy". Gene 2019, vol. 719, pp. 1-12.

Yin et al. "Non-viral vectors for gene-based therapy" Nature Reviews, Genetics vol. 15, Aug. 2014 , pp. 541-555.

(56) References Cited

OTHER PUBLICATIONS

Alix-Panabieres et al. Circulating tumor cells: liquid biopsy of cancer. Clin Chem. Jan. 2013;59(1):110-8.
Dovey et al. (2009) Defining cancer stem cells by xenotransplantation in zebrafish, Meth. Mol. Biol.568: 1-5 (Chapter).
Telford WG. Stem cell side population analysis and sorting using DyeCycle violet. Curr Protoc Cytom. Jan. 2010; Chapter 9:Unit9.30.
Vojtesek et al. Conformational changes in p53 analyzed using new antibodies to the core DNA binding domain of the protein. Oncogene. Jan. 19, 1995; 10(2): 389-93.
Yasunari Kanda, Cancer stem cells as a new pharmacological target, Folia Pharmacologica Japonica, 2014, vol. 144, Issue 1, pp. 17-21.
Ando et al. Cancer stem cell The therapy strategy, W'Waves, 2014, 20 (1), 24-28.
Oct. 18, 2019 (JP) Notice of reasons of refusal JP Application No. 2017-540163.

FIG. 5A
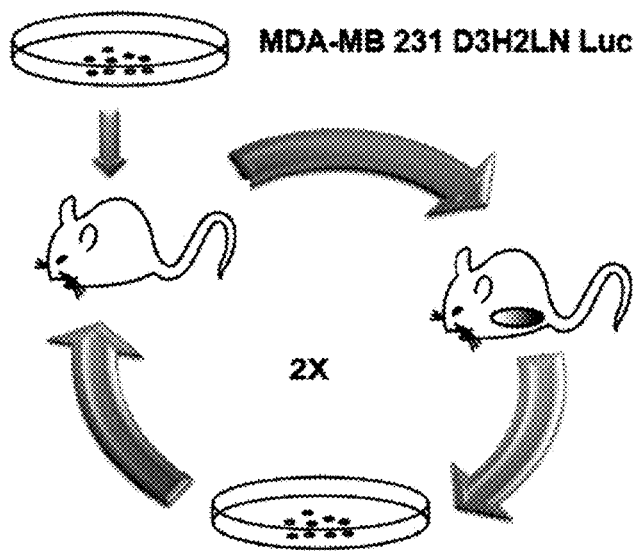
FIG. 5B
| Passage No. | Cell lines | Primary tumor take rate | Metastasis dissemination | | |
|---|---|---|---|---|---|
| | | | Rate | Organs | Day of first detection |
| 0 | MDA-MB 231 D3H2LN | 100% | 20% | Ax/br LN | 82 |
| 2 | C3 LND | 100% | 100% | Ax/br LN | 20 |
FIG. 5C
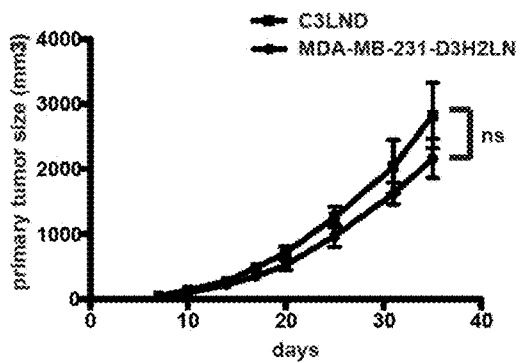
FIG. 5D
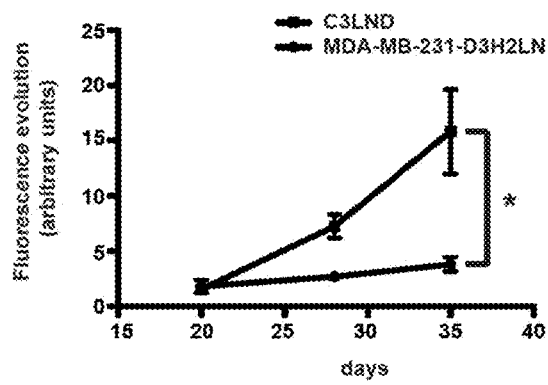

SEQUENCE LISTING

```
<160> NUMBER OF SEQ ID NOS: 19

<210> SEQ ID NO 1
<211> LENGTH: 209
<212> TYPE: PRT
<213> ORGANISM: Homo sapiens
<220> FEATURE:
<221> NAME/KEY: SITE
<222> LOCATION: (1)..(209)
<223> OTHER INFORMATION: Homo sapiens tumor protein p53, isoform
      delta133p53beta (Genbank NP_001119588.1)

<400> SEQUENCE: 1

Met Phe Cys Gln Leu Ala Lys Thr Cys Pro Val Gln Leu Trp Val Asp
1               5                   10                  15

Ser Thr Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190
```

```
           Gly Glu Tyr Phe Thr Leu Gln Asp Gln Thr Ser Phe Gln Lys Glu Asn
                195                 200                 205

Cys

<210> SEQ ID NO 2
<211> LENGTH: 2404
<212> TYPE: DNA
<213> ORGANISM: Homo sapiens
<220> FEATURE:
<221> NAME/KEY: misc_feature
<223> OTHER INFORMATION: Homo sapiens tumor protein p53, isoform
      delta133p53beta (Genbank NM_001126116.1)

<400> SEQUENCE: 2
tgaggccagg agatggaggc tgcagtgagc tgtgatcaca ccactgtgct ccagcctgag      60
tgacagagca agaccctatc tcaaaaaaaa aaaaaaaaa gaaaagctcc tgaggtgtag     120
acgccaactc tctctagctc gctagtgggt tgcaggaggt gcttacgcat gtttgtttct     180
ttgctgccgt cttccagttg ctttatctgt tcacttgtgc cctgactttc aactctgtct     240
ccttcctctt cctacagtac tcccctgccc tcaacaagat gttttgccaa ctggccaaga     300
cctgccctgt gcagctgtgg gttgattcca caccccgcc cggcacccgc gtccgcgcca     360
tggccatcta caagcagtca cagcacatga cggaggttgt gaggcgctgc ccccaccatg     420
agcgctgctc agatagcgat ggtctggccc ctcctcagca tcttatccga gtggaaggaa     480
atttgcgtgt ggagtatttg gatgacagaa acacttttcg acatagtgtg gtggtgccct     540
atgagccgcc tgaggttggc tctgactgta ccaccatcca ctacaactac atgtgtaaca     600
gttcctgcat gggcggcatg aaccggaggc ccatcctcac catcatcaca ctggaagact     660
ccagtggtaa tctactggga cggaacagct ttgaggtgcg tgtttgtgcc tgtcctggga     720
gagaccggcg cacagaggaa gagaatctcc gcaagaaagg ggagcctcac acgagctgc     780 ccccagggag cactaagcga gcactgccca caacaccag ctcctctccc agccaaaga     840 agaaaccact ggatggagaa tatttcaccc ttcaggacca gaccagcttt caaaaagaaa     900
attgttaaag agagcatgaa aatggttcta tgactttgcc tgatacagat gctacttgac     960
ttacgatggt gttacttcct gataaactcg tcgtaagttg aaaatattat ccgtgggcgt    1020
gagcgcttcg agatgttccg agagctgaat gaggccttgg aactcaagga tgcccaggct    1080
gggaaggagc caggggggag cagggctcac tccagccacc tgaagtccaa aaagggtcag    1140
tctacctccc gccataaaaa actcatgttc aagacagaag ggcctgactc agactgacat    1200
tctccacttc ttgttcccca ctgacagcct cccacccca tctctccctc ccctgccatt    1260
ttgggttttg ggtctttgaa cccttgcttg caataggtgt gcgtcagaag cacccaggac    1320
ttccatttgc tttgtcccgg ggctccactg aacaagttgg cctgcactgg tgttttgttg    1380
tggggaggag gatggggagt aggacatacc agcttagatt ttaaggtttt tactgtgagg    1440
gatgtttggg agatgtaaga aatgttcttg cagttaaggg ttagtttaca atcagccaca    1500
ttctaggtag gggcccactt caccgtacta accagggaag ctgtccctca ctgttgaatt    1560
ttctctaact tcaaggccca tatctgtgaa atgctggcat ttgcacctac ctcacagagt    1620
gcattgtgag ggttaatgaa ataatgtaca tctggccttg aaaccacctt ttattacatg    1680
gggtctagaa cttgacccc ttgagggtgc ttgttccctc tccctgttgg tcggtgggtt    1740 ggtagttttct acagttgggc agctggttag gtagagggga ttgtcaagtc tctgctggcc    1800
cagccaaacc ctgtctgaca acctcttggt gaaccttagt acctaaaagg aaatctcacc    1860
```

```
ccatcccaca ccctggagga tttcatctct tgtatatgat gatctggatc caccaagact   1920
tgttttatgc tcagggtcaa tttcttttt  ctttttttt  tttttttttc ttttctttg    1980 agactgggtc tcgctttgtt gcccaggctg gagtggagtg gcgtgatctt ggcttactgc   2040
agcctttgcc tccccggctc gagcagtcct gcctcagcct ccggagtagc tgggaccaca   2100
ggttcatgcc accatggcca gccaactttt gcatgttttg tagagatggg gtctcacagt   2160
gttgcccagg ctggtctcaa actcctgggc tcaggcgatc cacctgtctc agcctcccag   2220
agtgctggga ttacaattgt gagccaccac gtccagctgg aagggtcaac atcttttaca   2280
ttctgcaagc acatctgcat tttcacccca cccttcccct ccttctccct ttttatatcc   2340 cattttata  tcgatctctt attttacaat aaaactttgc tgccacctgt gtgtctgagg   2400
ggtg                                                                2404
```

<210> SEQ ID NO 3
<211> LENGTH: 214
<212> TYPE: PRT
<213> ORGANISM: Homo sapiens
<220> FEATURE:
<221> NAME/KEY: SITE
<222> LOCATION: (1)..(214)
<223> OTHER INFORMATION: Homo sapiens tumor protein p53, isoform
      delta133p53gamma (Genbank NP_001119589.1)

<400> SEQUENCE: 3

Met Phe Cys Gln Leu Ala Lys Thr Cys Pro Val Gln Leu Trp Val Asp
1               5                   10                  15

Ser Thr Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Met Leu Leu Asp Leu Arg Trp Cys Tyr
        195                 200                 205

Phe Leu Ile Asn Ser Ser
    210

<210> SEQ ID NO 4
<211> LENGTH: 2331
<212> TYPE: DNA

<213> ORGANISM: Homo sapiens
<220> FEATURE:
<221> NAME/KEY: misc_feature
<223> OTHER INFORMATION: Homo sapiens tumor protein p53, isoform
      delta133p53gamma (Genbank NM_001126117.1)

<400> SEQUENCE: 4

| | | | | | |
|---|---|---|---|---|---|
| tgaggccagg | agatggaggc | tgcagtgagc | tgtgatcaca | ccactgtgct | ccagcctgag | 60 |
| tgacagagca | agaccctatc | tcaaaaaaaa | aaaaaaaaaa | gaaaagctcc | tgaggtgtag | 120 |
| acgccaactc | tctctagctc | gctagtgggt | tgcaggaggt | gcttacgcat | gtttgtttct | 180 |
| ttgctgccgt | cttccagttg | ctttatctgt | tcacttgtgc | cctgactttc | aactctgtct | 240 |
| ccttcctctt | cctacagtac | tcccctgccc | tcaacaagat | gttttgccaa | ctggccaaga | 300 |
| cctgccctgt | gcagctgtgg | gttgattcca | caccccgcc | cggcacccgc | gtccgcgcca | 360 |
| tggccatcta | caagcagtca | cagcacatga | cggaggttgt | gaggcgctgc | ccccaccatg | 420 |
| agcgctgctc | agatagcgat | ggtctggccc | ctcctcagca | tcttatccga | gtggaaggaa | 480 |
| atttgcgtgt | ggagtatttg | gatgacagaa | acacttttcg | acatagtgtg | gtggtgccct | 540 |
| atgagccgcc | tgaggttggc | tctgactgta | ccaccatcca | ctacaactac | atgtgtaaca | 600 |
| gttcctgcat | gggcggcatg | aaccggaggc | ccatcctcac | catcatcaca | ctggaagact | 660 |
| ccagtggtaa | tctactggga | cggaacagct | ttgaggtgcg | tgtttgtgcc | tgtcctggga | 720 |
| gagaccggcg | cacagaggaa | gagaatctcc | gcaagaaagg | ggagcctcac | cacgagctgc | 780 |
| ccccagggag | cactaagcga | gcactgccca | acaacaccag | ctcctctccc | cagccaaaga | 840 |
| agaaaccact | ggatggagaa | tatttcaccc | ttcagatgct | acttgactta | cgatggtgtt | 900 |
| acttcctgat | aaactcgtcg | taagttgaaa | atattatccg | tgggcgtgag | cgcttcgaga | 960 |
| tgttccgaga | gctgaatgag | gccttggaac | tcaaggatgc | ccaggctggg | aaggagccag | 1020 |
| gggggagcag | ggctcactcc | agccacctga | agtccaaaaa | gggtcagtct | acctcccgcc | 1080 |
| ataaaaaact | catgttcaag | acagaagggc | ctgactcaga | ctgacattct | ccacttcttg | 1140 |
| ttccccactg | acagcctccc | acccccatct | ctccctcccc | tgccattttg | ggttttgggt | 1200 |
| ctttgaaccc | ttgcttgcaa | taggtgtgcg | tcagaagcac | ccaggacttc | catttgcttt | 1260 |
| gtcccggggc | tccactgaac | aagttggcct | gcactggtgt | tttgttgtgg | ggaggaggat | 1320 |
| ggggagtagg | acataccagc | ttagatttta | aggttttac | tgtgagggat | gtttgggaga | 1380 |
| tgtaagaaat | gttcttgcag | ttaagggtta | gtttacaatc | agccacattc | taggtagggg | 1440 |
| cccacttcac | cgtactaacc | agggaagctg | tccctcactg | ttgaatttc | tctaacttca | 1500 |
| aggcccatat | ctgtgaaatg | ctggcatttg | cacctacctc | acagagtgca | ttgtgagggt | 1560 |
| taatgaaata | atgtacatct | ggccttgaaa | ccacctttta | ttacatgggg | tctagaactt | 1620 |
| gaccccttg | agggtgcttg | ttccctctcc | ctgttggtcg | gtgggttggt | agtttctaca | 1680 |
| gttgggcagc | tggttaggta | gagggagttg | tcaagtctct | gctggcccag | ccaaaccctg | 1740 |
| tctgacaacc | tcttggtgaa | ccttagtacc | taaaaggaaa | tctcaccca | tcccacaccc | 1800 |
| tggaggattt | catctcttgt | atatgatgat | ctggatccac | caagacttgt | tttatgctca | 1860 |
| gggtcaattt | cttttttctt | tttttttttt | tttttctttt | tcttttgaga | ctgggtctcg | 1920 |
| ctttgttgcc | caggctggag | tggagtggcg | tgatcttggc | ttactgcagc | ctttgcctcc | 1980 |
| ccggctcgag | cagtcctgcc | tcagcctccg | gagtagctgg | gaccacaggt | tcatgccacc | 2040 |
| atggccagcc | aacttttgca | tgttttgtag | agatgggggtc | tcacagtgtt | gcccaggctg | 2100 |
| gtctcaaact | cctgggctca | ggcgatccac | ctgtctcagc | ctcccagagt | gctgggatta | 2160 |

-continued

```
caattgtgag ccaccacgtc cagctggaag ggtcaacatc ttttacattc tgcaagcaca    2220
tctgcatttt caccccaccc ttccctcct tctccctttt tatatcccat ttttatatcg    2280
atctcttatt ttacaataaa actttgctgc cacctgtgtg tctgagggt g             2331
```

<210> SEQ ID NO 5
<211> LENGTH: 393
<212> TYPE: PRT
<213> ORGANISM: Homo sapiens
<220> FEATURE:
<221> NAME/KEY: SITE
<222> LOCATION: (1)..(393)
<223> OTHER INFORMATION: Homo sapiens tumor protein p53
      (Genbank NP_000537.3)

<400> SEQUENCE: 5

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
        340                 345                 350

Ala Gln Ala Gly Lys Glu Pro Gly Gly Ser Arg Ala His Ser Ser His
    355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 6
<211> LENGTH: 2586
<212> TYPE: DNA
<213> ORGANISM: Homo sapiens
<220> FEATURE:
<221> NAME/KEY: misc_feature
<223> OTHER INFORMATION: Homo sapiens tumor protein p53 cDNA
       (Genbank NM_000546.4)

<400> SEQUENCE: 6

| | |
|---|---|
| gattggggtt tcccctcccc atgtgctcaa gactggcgct aaaagttttg agcttctcaa | 60 |
| aagtctagag ccaccgtcca gggagcaggt agctgctggg ctccggggac actttgcgtt | 120 |
| cgggctggga gcgtgctttc cacgacggtg acacgcttcc ctggattggc agccagactg | 180 |
| ccttccgggt cactgccatg gaggagccgc agtcagatcc tagcgtcgag ccccctctga | 240 |
| gtcaggaaac attttcagac ctatggaaac tacttcctga aaacaacgtt ctgtcccct | 300 |
| tgccgtccca gcaatggatg atttgatgc tgtccccgga cgatattgaa caatggttca | 360 |
| ctgaagaccc aggtccagat gaagctccca gaatgccaga gctgctccc ccgtggccc | 420 |
| ctgcaccagc agctcctaca ccggcggccc ctgcaccagc cccctcctgg cccctgtcat | 480 |
| cttctgtccc ttcccagaaa acctaccagg gcagctacgg tttccgtctg gcttcttgc | 540 |
| attctgggac agccaagtct gtgacttgca cgtactcccc tgccctcaac aagatgtttt | 600 |
| gccaactggc caagacctgc cctgtgcagc tgtgggttga ttccacaccc cgcccggca | 660 |
| cccgcgtccg cgccatggcc atctacaagc agtcacagca catgacggag gttgtgaggc | 720 |
| gctgccccca ccatgagcgc tgctcagata gcgatggtct ggcccctcct cagcatctta | 780 |
| tccgagtgga aggaaatttg cgtgtggagt atttggatga cagaaacact tttcgacata | 840 |
| gtgtggtggt gccctatgag ccgcctgagg ttggctctga ctgtaccacc atccactaca | 900 |
| actacatgtg taacagttcc tgcatgggcg gcatgaaccg gaggcccatc ctcaccatca | 960 |
| tcacactgga agactccagt ggtaatctac tgggacggaa cagctttgag gtgcgtgttt | 1020 |
| gtgcctgtcc tgggagagac cggcgcacag aggaagagaa tctccgcaag aaaggggagc | 1080 |
| ctcaccacga gctgccccca gggagcacta agcgagcact gcccaacaac accagctcct | 1140 |
| ctccccagcc aaagaagaaa ccactggatg gagaatattt cacccttcag atccgtgggc | 1200 |
| gtgagcgctt cgagatgttc cgagagctga atgaggcctt ggaactcaag gatgcccagg | 1260 |
| ctgggaagga gccaggggg agcagggctc actccagcca cctgaagtcc aaaaagggtc | 1320 |
| agtctacctc ccgccataaa aaactcatgt tcaagacaga agggcctgac tcagactgac | 1380 |
| attctccact tcttgttccc cactgacagc ctcccaccccc catctctccc tcccctgcca | 1440 |
| ttttgggttt tgggtctttg aacccttgct tgcaataggt gtgcgtcaga agcacccagg | 1500 |
| acttccattt gctttgtccc ggggctccac tgaacaagtt ggcctgcact ggtgttttgt | 1560 |

-continued

```
tgtggggagg aggatggggga gtaggacata ccagcttaga tttttaaggtt tttactgtga    1620 gggatgtttg ggagatgtaa gaaatgttct tgcagttaag ggttagttta caatcagcca    1680
cattctaggt aggggcccac ttcaccgtac taaccaggga agctgtccct cactgttgaa    1740
ttttctctaa cttcaaggcc catatctgtg aaatgctggc atttgcacct acctcacaga    1800
gtgcattgtg agggttaatg aaataatgta catctggcct tgaaaccacc ttttattaca    1860
tggggtctag aacttgaccc ccttgagggt gcttgttccc tctccctgtt ggtcggtggg    1920
ttggtagttt ctacagttgg gcagctggtt aggtagaggg agttgtcaag tctctgctgg    1980
cccagccaaa ccctgtctga caacctcttg gtgaaccttaa gtacctaaaa ggaaatctca    2040
ccccatccca caccctggag gatttcatct cttgtatatg atgatctgga tccaccaaga    2100
cttgttttat gctcagggtc aatttctttt ttctttttt ttttttttt tctttttctt      2160 tgagactggg tctcgctttg ttgcccaggc tggagtggag tggcgtgatc ttggcttact     2220
gcagcctttg cctccccggc tcgagcagtc ctgcctcagc ctccggagta gctgggacca    2280
caggttcatg ccaccatggc cagccaactt ttgcatgttt tgtagagatg gggtctcaca    2340
gtgttgccca ggctggtctc aaactcctgg gctcaggcga tccacctgtc tcagcctccc    2400
agagtgctgg gattacaatt gtgagccacc acgtccagct ggaagggtca acatctttta    2460
cattctgcaa gcacatctgc atttccaccc caccccttccc ctccttctcc cttttatat    2520 cccatttta tatcgatctc ttattttaca ataaaactt gctgccacct gtgtgtctga     2580
ggggtg                                                            2586
```

```
<210> SEQ ID NO 7
<211> LENGTH: 26
<212> TYPE: DNA
<213> ORGANISM: Artificial sequence
<220> FEATURE:
<223> OTHER INFORMATION: Forward primer for amplifying human delta133p53
      isoforms (Alpha, Beta and gamma)

<400> SEQUENCE: 7
actctgtctc cttcctcttc ctacag                                        26

<210> SEQ ID NO 8
<211> LENGTH: 21
<212> TYPE: DNA
<213> ORGANISM: Artificial sequence
<220> FEATURE:
<223> OTHER INFORMATION: Reward primer for amplifying human delta133p53
      isoforms (Alpha, Beta and gamma)

<400> SEQUENCE: 8
gtgtggaatc aacccacagc t                                             21

<210> SEQ ID NO 9
<211> LENGTH: 28
<212> TYPE: DNA
<213> ORGANISM: Artificial sequence
<220> FEATURE:
<223> OTHER INFORMATION: Probe for detecting human delta133p53 isoforms
      (Alpha, Beta and gamma)

<400> SEQUENCE: 9 tccectgccc tcaacaagat gttttgcc                                      28

<210> SEQ ID NO 10
<211> LENGTH: 25
```

```
<212> TYPE: DNA
<213> ORGANISM: Artificial sequence
<220> FEATURE:
<223> OTHER INFORMATION: Forward primer for amplifying human p53 beta
      isoforms (p53 TAbeta, delta40p53beta, delta133p53beta, and
      delta160p53beta)

<400> SEQUENCE: 10
aaccactgga tggagaatat ttcac                                         25

<210> SEQ ID NO 11
<211> LENGTH: 26
<212> TYPE: DNA
<213> ORGANISM: Artificial sequence
<220> FEATURE:
<223> OTHER INFORMATION: Reward primer for amplifying human p53 beta
      isoforms (p53 TAbeta, delta40p53beta, delta133p53beta, and
      delta160p53beta)

<400> SEQUENCE: 11
tcatagaacc attttcatgc tctctt                                        26

<210> SEQ ID NO 12
<211> LENGTH: 34
<212> TYPE: DNA
<213> ORGANISM: Artificial sequence
<220> FEATURE:
<223> OTHER INFORMATION: Probe for detecting human p53 beta isoforms
      (p53 TAbeta, delta40p53beta, delta133p53beta, and delta160p53beta)

<400> SEQUENCE: 12
caggaccaga ccagctttca aaagaaaat tgtt                                34

<210> SEQ ID NO 13
<211> LENGTH: 19
<212> TYPE: DNA
<213> ORGANISM: Artificial sequence
<220> FEATURE:
<223> OTHER INFORMATION: Sequence of DBD domain in all human p53
      isoforms targeted by shRNA Sh1

<400> SEQUENCE: 13
gactccagtg gtaatctac                                                19

<210> SEQ ID NO 14
<211> LENGTH: 19
<212> TYPE: DNA
<213> ORGANISM: Artificial sequence
<220> FEATURE:
<223> OTHER INFORMATION: Sequence of 5? UTR of all delta133 isoforms
      (Alpha, Beta and gamma) targeted by shRNA Sh3

<400> SEQUENCE: 14
ggaggtgctt acacatgtt                                                19

<210> SEQ ID NO 15
<211> LENGTH: 19
<212> TYPE: DNA
<213> ORGANISM: Artificial sequence
<220> FEATURE:
<223> OTHER INFORMATION: Sequence of 5? UTR of all delta133 isoforms
      (Alpha, Beta and gamma) targeted by shRNA Sh4

<400> SEQUENCE: 15
cttgtgccct gactttcaa                                                19

<210> SEQ ID NO 16
```

```
<211> LENGTH: 18
<212> TYPE: DNA
<213> ORGANISM: Artificial sequence
<220> FEATURE:
<223> OTHER INFORMATION: Sequence of 3?end of all p53 beta isoforms
      (p53 TAbeta, delta40p53beta, delta133p53beta, and delta160p53beta)
      targeted by shRNA Sh5

<400> SEQUENCE: 16
ggaccagacc agctttca                                                 18

<210> SEQ ID NO 17
<211> LENGTH: 39
<212> TYPE: DNA
<213> ORGANISM: Artificial sequence
<220> FEATURE:
<223> OTHER INFORMATION: Oligonucleotide for introducing resistance to
      Sh1

<400> SEQUENCE: 17
catcacactg gaagattcta gcggcaatct actgggacg                          39

<210> SEQ ID NO 18
<211> LENGTH: 21
<212> TYPE: DNA
<213> ORGANISM: Artificial sequence
<220> FEATURE:
<223> OTHER INFORMATION: Sequence of TAD domain present in long TAp53
      and delta40p53 isoforms targeted by shRNA Sh2

<400> SEQUENCE: 18
gtccagatga agctcccaga a                                             21

<210> SEQ ID NO 19
<211> LENGTH: 19
<212> TYPE: DNA
<213> ORGANISM: Artificial sequence
<220> FEATURE:
<223> OTHER INFORMATION: Sequence of 3?end of all p53 alpha isoforms
      (p53 TAalpha, delta40p53alpha, delta133p53alpha, and
      delta160p53alpha) targeted by shRNA Sh6

<400> SEQUENCE: 19
gtgagcgctt cgagatgtt                                                19
```

DELTA133P53BETA AND DELTA133P53GAMMA ISOFORMS ARE BIOMARKERS OF CANCER STEM CELLS

RELATED APPLICATIONS

This application is a continuation of U.S. application Ser. No. 15/547,211, filed Jul. 28, 2017, which is a National Stage Application under 35 U.S.C. 371 of co-pending PCT application PCT/EP2016/052095 designating the United States and filed Feb. 1, 2016; which claims the benefit of EP application Ser. No. 15/305,146.1 and filed Jan. 30, 2015 each of which are hereby incorporated by reference in their entireties.

TECHNICAL FIELD OF THE INVENTION

The present invention is in the field of oncology, and more particularly of cancer stem cells. It relates to a method for producing cancer stem cells based on overexpression of Δ133p53β isoform, Δ133p53γ isoform, or both Δ133p53β and Δ133p53γ isoforms; a method for predicting the risk that treatment with a chemotherapeutic anti-cancer agent induces cancer stem cells in a subject suffering from cancer from a cancer sample of said subject, based on detection of an increase in Δ133p53β isoform, Δ133p53γ isoform, or both Δ133p53β and Δ133p53γ isoforms following chemotherapeutic anti-cancer treatment; to therapeutic uses of a combination of chemotherapeutic anti-cancer agent and an agent reducing Δ133p53β isoform, Δ133p53γ isoform, or both Δ133p53β and Δ133p53γ isoforms expression; and also to screening methods for anti-cancer stem cells agents.

BACKGROUND ART

Cancer stem cells (CSCs) are cancer cells with the ability to perpetuate through self-renewal and the ability to generate all distinct cell types found in their original tumor. CSCs usually represent a small fraction of the cells within a malignant tumor. However, owing to their capacity for self-renewal and asymmetric division, CSCs are believed to be the source of unlimited tumor regeneration, heterogeneity and resistance to standard treatment.

As CSC eradication seems necessary for the final cure of many cancer types in humans, it is vital to better understand their biology. However, due to their low abundance in cancer tissues, their study is difficult. There is thus a need for methods to generate sufficient numbers of CSCs for further study.

The tumor suppressor p53 exercises its functions mainly through modulation of gene expression and it was proposed to be the "guardian of the genome" (Lane, 1992). However, p53 functions are ubiquitously altered in cancer cells by mutations/perturbation of its signaling pathways and loss of p53 activity is a prerequisite for cancer development. Mutant p53 is thought to play a pivotal role in promoting invasion, favoring cancer cell exit from the primary tumor site and dissemination, ultimately leading to metastasis formation (Gadea et al., 2007a, b; Muller et al., 2009; Roger et al., 2010; Vinot et al., 2008).

Recent reports have documented the role of p53 in stem cell homeostasis and pluripotency. Wild type (wt) p53 counteracts somatic cell reprogramming (Hong et al., 2009; Kawamura et al., 2009; Liu et al., 2009; Utikal et al., 2009), whereas mutant p53 stimulates induced pluripotent stem (iPS) cell formation (Sarig et al., 2010). A recent genome-wide study demonstrated that p53 regulates approximately 3600 genes in mouse ES cells (Li et al., 2012). The group of positively regulated genes (about 2000) is enriched in genes responsible for cell differentiation, while the negatively regulated group (about 1600 genes) is involved mainly in maintaining the ES cell status. p53 represses key regulators of the stem cell phenotype, such as Oct 3/4, Nanog, Sox 2 and c-Myc (Yamanaka factors, Li et al., 2012). Stress-induced activation of the p53 signaling pathway in ES cells leads to cell differentiation rather than apoptosis and cell death (Zhao and Xu, 2010). Accordingly, p53 hinders cell reprogramming through the p21 signaling pathway (Hong et al., 2009). Depletion of p53 significantly increases cell reprogramming efficacy and facilitates iPS cell generation using only two factors from the Yamanaka cocktail (SOX 2 and Oct 3/4) (Kawamura et al., 2009). Consequently, p53 might be considered not only as the guardian of the genome, but also as the guardian of reprogramming.

All these functions are associated with full-length p53 (i.e., the TAp53α isoform). However, the TP53 gene encodes at least twelve different physiological isoforms [TAp53 (α, β and γ), Δ40p53 (α, β and γ), Δ133p53 (α, β and γ) and Δ160p53 (α, β and γ)] (Bourdon, 2007) via several mechanisms: use of alternative promoters (the TA and Δ133 isoforms), alternative intron splicing (intron 2: Δ40 isoforms and intron 9: α, β and γ isoforms) and alternative translational initiation sites (Δ40 isoforms and Δ160 isoforms). A scheme summarizing the features of isoforms α, β and γ of TAp53, Δ40p53, and Δ133p53 is presented in FIG. 1A. The TAp53α isoform is the best described and classically mentioned in the literature as p53. Basically, p53 isoforms can be divided in two groups: long isoforms that contain the transactivation domain (TA and Δ40) and short isoforms without transactivation domain (Δ133 and Δ160). Furthermore, the β and γ isoforms do not contain the canonical C-terminal oligomerization domain, but an additional domain with unknown function(s) to date (Khoury and Bourdon, 2011).

Several clinical studies have reported that p53 isoforms are abnormally expressed in many human cancer types (Avery-Kiejda et al., 2014; Boldrup et al., 2007; Bourdon et al., 2005; Bourdon et al., 2011; Hofstetter et al., 2012). As differential expression of p53 isoforms can affect p53 tumor suppressor activity, their deregulated expression could contribute to tumorigenesis in cancers that express wild type p53. For instance, the N-terminal truncated isoforms Δ40p53 and Δ133p53 exert dominant negative functions towards wild type p53, by inhibiting transactivation of its target genes and by interfering with p53-dependent growth suppression (Bourdon et al., 2005; Davidson et al.; Fujita et al., 2009). Moreover, Δ40p53 can modulate transcription by reorienting p53 signaling (Hafsi et al., 2013; Takahashi et al., 2014). All these results on the interactions between p53 and its N-terminal isoforms suggest that, in specific conditions, these isoforms may either enhance or decrease the basal level of p53 activity, thus contributing to set a threshold for p53-dependent responses to endogenous or exogenous stimuli.

WO2009/029054 suggests to treat or prevent cancer by reducing or inhibiting expression of at least one p53 isoform modulating expression or activity of p53, in particular by reducing or inhibiting expression of N-terminal truncated Δ113p53 or Δ133p53 isoforms, which are considered to act as dominant negative regulators of full-length p53. While both Δ113p53 and Δ133p53 isoforms are mentioned, data is provided only for Δ113p53. In addition, among the three Δ133 isoforms of p53, WO2009/029054 only suggests the use of Δ133p53 (which is also referred to as Δ133p53α), but not of isoforms Δ133p53β and Δ133p53γ.

WO2011/000891 describes that expression of isoforms Δ133p53β in cancer cells is a marker of increased risk of cancer metastasis. On this basis, this application proposes measuring the aggressiveness of cancer in a subject and determining the subject's response to an anti-cancer therapy based on determination of the expression level of Δ133p53α (also referred to as Δ133p53), Δ133p53β or Δ133p53γ in a cancer sample of said subject. The method of determining the subject's response to an anti-cancer therapy is based on the fact that metastatic cancer patients often do not respond positively to conventional anticancer therapy. WO2011/000891 further proposes screening potential anti-metastatic compounds based on the ability of test compounds to decrease the expression level of Δ133p53α (also referred to as Δ133p53), Δ133p53β or Δ133p53γ in a cell expressing Δ133p53α (also referred to as Δ133p53), Δ133p53β or Δ133p53γ. In light of WO2011/000891, it clearly appears that detecting the expression of at least one of Δ133p53α, Δ133p53β or Δ133p53γ isoforms is indicative for risk of metastatic cancer. Furthermore, it suggests that these isoforms may be involved in cell invasiveness by enhancing cell motility. However, this document does not suggest that said cell invasiveness is linked to the production of cancer stem cells.

In this respect, it should be made clear that while invasiveness is necessary for metastasis, it is not synonymous of the production of cancer stem cells. In particular, while both invasiveness and cancer stem cells are associated to metastasis, this does not mean that these two notions are equivalent.

This is illustrated by the fact that some genes, which are known to be associated to invasiveness, are not able to generate cancer stem cells, in particular alone, without the previous or concomitant induction of overexpression of transcription factors known to be useful of reprogramming cells towards pluripotency, such as Sox 2, Oct 3/4 and Nanog.

For instance, as explained above, WO2011/000891 suggests that Δ133p53α, Δ133p53β or Δ133p53γ isoforms may be involved in cell invasiveness by enhancing cell motility. Similarly, Bernard et al—2013 also suggests that specifically the Δ133p53α and Δ133p53γ isoforms, but not Δ133p53γ, stimulate angiogenesis and are thus involved in invasiveness. However, WO2012/044979 suggests that Δ133p53 (also referred to as Δ133p53α) may be used to produce cancer stem cells only when co-expressed with another reprogramming factor, such as OCT4, SOX2 or c-myc. In addition, the inventors found that Δ133p53α is actually not able, in the absence of another reprogramming factor, such as OCT4, SOX2 or c-myc, to generate cancer stem cells.

It should be noted that it was generally considered in the prior art that overexpression of transcription factors known to be useful of reprogramming cells towards pluripotency, such as Sox 2, Oct 3/4 and Nanog is considered as a prerequisite for reprogramming cells, including cancer cells, towards pluripotency.

Therefore, while many genes have been disclosed in the prior art as involved in invasiveness and metastasis, this does not help skilled persons to identify genes that would be able, without the previous or concomitant induction of overexpression of transcription factors known to be useful of reprogramming cells towards pluripotency, such as Sox 2, Oct 3/4 and Nanog, to reprogram cancer cells towards pluripotency and thus to generate cancer stem cells.

SUMMARY OF THE INVENTION

In the context of the present invention, the inventors have now found that Δ133p53β isoform (and also Δ133p53γ to a lesser extent), but not Δ133p53α isoform (also referred to as Δ133p53 isoform), is not only a marker of a risk of cancer metastasis, but actually promotes cancer stem cell phenotype. In particular, expression of Δ133p53β isoform (and also Δ133p53γ to a lesser extent), but not of Δ133p53α isoform (also referred to as Δ133p53 isoform), promotes cancer cell sphere-forming activity, and also promotes Sox 2, Oct 3/4 and Nanog expression (but not c-Myc), transcription factors known to be useful of reprogramming cells towards pluripotency.

This finding was not expected, since not all markers of metastasis risk are involved in development of cancer stem cells. For example, WO2011/000891 suggests detecting the presence of Δ133p53α isoform in order to determine if the tested patient risk to develop metastatic cancer. Other authors (Bernard et al., 2013) have also suggested that Δ133p53α isoform is able to stimulate angiogenesis and is thus involved in cancer cell invasiveness. However, in the present invention, the inventors demonstrated that Δ133p53α isoform is unable to induce the development of cancer stem cells. Indeed, while increasing evidences suggest that CSCs and metastasis development are closely linked, many questions are still unsolved concerning the precise role of CSCs in metastasis development.

The above finding the inventors is very important since it provides a mean for producing high numbers of CSCs, thus permitting to study and better understand their biology, a crucial point for improving anticancer therapies.

In a first aspect, the present invention thus relates to a method for producing cancer stem cells, comprising:
a) transducing cancer cells with a vector expressing Δ133p53β isoform, Δ133p53γ isoform, or both Δ133p53β and Δ133p53γ isoforms;
b) culturing transduced cancer cells in a medium supporting expansion of transduced cancer cells; and
c) isolating cancer stem cells.

The inventors further surprisingly found that anticancer treatment of cancer cells by etoposide (a topoisomerase II inhibitor) may not be only inefficient but may further promote cancer stemness by increasing Δ133p53β expression level, which itself increases the expression level of transcription factors specifically expressed by stem cells, such as Oct 3/4, Nanog and Sox 2. As a result, treating cancer patients with etoposide may promote CSC formation and would then be rather deleterious than useful.

The present invention thus also relates to a method for predicting the risk that treatment with a chemotherapeutic anti-cancer agent induces cancer stem cells in a subject suffering from cancer from a cancer sample of said subject, comprising:
a) measuring in vitro the expression level of Δ133p53β isoform, Δ133p53γ isoform, or both Δ133p53β and Δ133p53γ isoforms in said cancer sample, untreated with the chemotherapeutic anti-cancer agent;
b) treating said cancer sample with said chemotherapeutic anti-cancer agent;
c) measuring in vitro the expression level of Δ133p53β isoform, Δ133p53γ isoform, or both Δ133p53β and Δ133p53γ isoforms in the treated cancer sample;
d) comparing the values obtained in steps a) and c); and
e) concluding to:
(i) the presence of a significant risk that treatment with said chemotherapeutic anti-cancer agent induces cancer stem cells in said subject if the expression level of Δ133p53β isoform, Δ133p53γ isoform, or both Δ133p53β and Δ133p53γ isoforms measured in step c) is higher than the expression level of Δ133p53β isoform, Δ133p53γ isoform, or both Δ133p53β and Δ133p53γ isoforms measured in step a), or (ii) the absence of a significant risk that treatment with said chemotherapeutic anti-cancer agent induces cancer stem cells in said subject if the expression level of Δ133p53β isoform, Δ133p53γ isoform, or both Δ133p53β and Δ133p53γ isoforms measured in step c) is lower than or equal to the expression level of Δ133p53β isoform, Δ133p53γ isoform, or both Δ133p53β and Δ133p53γ isoforms measured in step a).

Based on the same finding of the inventors that anticancer treatment of cancer cells by etoposide (a topoisomerase II inhibitor) may not be only inefficient (resistance to treatment) but may further promote cancer stemness by increasing Δ133p53β expression level, the present invention also relates to a chemotherapeutic anti-cancer agent, for use in the treatment of cancer in a subject suffering from a cancer, wherein said chemotherapeutic anti-cancer agent is administered to said subject in combination with an agent reducing Δ133p53β or Δ133p53γ isoform expression.

Similarly, the present invention also relates to a method for treating cancer in a subject suffering from a cancer, comprising:
a) Administering to said subject a therapeutically efficient amount of an agent reducing Δ133p53β isoform, Δ133p53γ isoform, or both Δ133p53β and Δ133p53γ isoforms expression; and
b) Administering to said subject a therapeutically efficient amount of a chemotherapeutic anti-cancer treatment.

The results obtained by the inventors show that Δ133p53β or Δ133p53γ isoform expression promotes cancer stem cell potential, in particular by upregulating expression of transcription factors Sox 2, Oct 3/4 and Nanog, suggesting that expression of Δ133p53β or Δ133p53γ isoform may be an early event of reprogramming of cancer cells towards cancer stem cells, and that detection of other cancer stem cells features in addition to detection of Δ133p53β or Δ133p53γ isoform expression may improve the reliability of prediction of a risk of cancer metastasis in a subject suffering from cancer. The present invention thus also relates to a method for predicting a risk of cancer metastasis in a subject suffering from cancer from a cancer sample of said subject, comprising:
a) detecting sphere-forming cancer cells expressing Δ133p53β isoform, Δ133p53γ isoform, or both Δ133p53β and Δ133p53γ isoforms in said cancer sample; and
b) concluding to the presence of a significant risk of cancer metastasis in said subject if sphere-forming cancer cells expressing Δ133p53β isoform, Δ133p53γ isoform, or both Δ133p53β and Δ133p53γ isoforms are detected and to the absence of a significant risk of cancer metastasis in said subject if sphere-forming cancer cells expressing Δ133p53β isoform, Δ133p53γ isoform, or both Δ133p53β and Δ133p53γ isoforms are not detected. Δ133p53β or Δ133p53γ isoform expression promoting cancer stem cell potential may also be used to predict a risk of cancer relapse in a treated cancer subject after successful elimination of most cancer cells.

The present invention thus also relates to a method for predicting a risk of cancer relapse in a treated cancer subject from a cell sample of said subject, comprising:
a) detecting the expression of Δ133p53β isoform, of Δ133p53γ isoform, or of both Δ133p53β and Δ133p53γ isoforms; and
b) concluding to the presence of a significant risk of cancer relapse in said subject if the expression of Δ133p53β isoform, of Δ133p53γ isoform, or of both Δ133p53β and Δ133p53γ isoforms is detected and to the absence of a significant risk of cancer relapse in said subject if neither the expression of Δ133p53β isoform nor the expression of Δ133p53γ isoform are detected.

Based on the same finding that Δ133p53β or Δ133p53γ isoform expression promotes cancer stem cell potential, in particular by upregulating expression of transcription factors Sox 2, Oct 3/4 and Nanog, suggesting that expression of Δ133p53β or Δ133p53γ isoform may be an early event of reprogramming of cancer cells towards cancer stem cells, the present invention also relates to a method for screening potential anti-cancer stem cells compounds, comprising:
a) providing sphere-forming cancer stem cells expressing Δ133p53β isoform, Δ133p53γ isoform, or both Δ133p53β and Δ133p53γ isoforms;
b) contacting said cancer stem cells with a test compound;
c) measuring in vitro the expression level of said Δ133p53β isoform, Δ133p53γ isoform, or both Δ133p53β and Δ133p53γ isoforms in treated cells and/or the sphere-forming ability of treated cells;
d) selecting said test compound as a potential anti-cancer stem cells compound if the expression level of said Δ133p53β isoform, Δ133p53γ isoform, or both Δ133p53β and Δ133p53γ isoforms in treated cells is lower than before treatment with the test compound, and/or if the sphere-forming ability of treated cells is lower than before treatment with the test compound.

DESCRIPTION OF THE FIGURES

FIGS. 5A-5G. Derivation and characterization of the C3LND cell line. A. Schematic representation of the approach used to derive the highly metastatic C3LND sub-clone starting from the MDA-MB231 D3H2LN cell line. B. Major oncogenic characteristics of the sub-clones obtained during C3LND isolation starting from MDA-MB-231 D3H2LN cells. LN: Lymph nodes; Ax/Br: Axillary/Branchial. C. Quantification of primary tumor growth (n=5 for each group and time point). D. Quantification of bioluminescence during tumor growth (n=5 for each group and time point). E. RT-qPCR analysis of c-Myc, Oct 3/4, Nanog and Sox 2 expression in C3LND cells after overexpression of the Δ133p53β isoform (n=3). F. Western blot analysis of p53 isoform transduced with Sh3 in MDA-MB-231 C3LND. G. Quantification of luminescence (n=2 for each group and time point).

DETAILED DESCRIPTION OF THE INVENTION

Definitions

P53 Isoforms

Figure 1A:
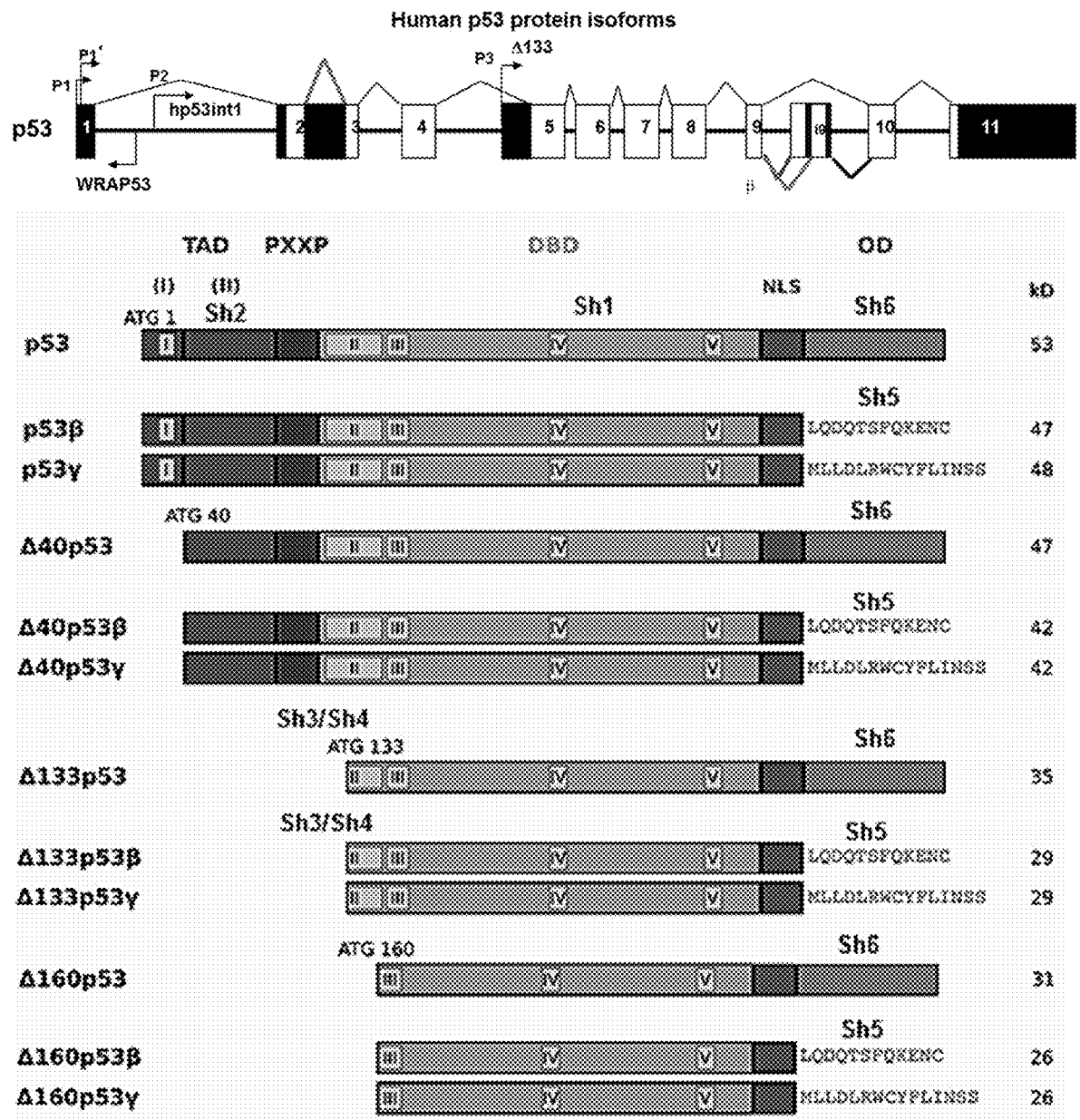
FIGS. 1A-1G. Selective depletion of p53 isoforms affects the sphere-forming ability of MCF-7 cells. A. Schematic representation of p53 isoforms with the targets of the different shRNAs (Sh) used in this study. The calculated molecular weights of the different isoforms are indicated. TA: transactivation domain; 5'UTR: 5' untranslated region; DBD: DNA binding domain; NLS: nuclear localization sequence; OD: oligomerization domain. B. Mammosphere quantification in MCF-7 cells after transduction of Sh1, Sh2, Sh3 Sh4 and Sh5 (n=3). C, D and E. Western blot analysis of p53 isoform depletion in the corresponding cells. F. and G. RT-qPCR quantification of the expression level of c-Myc, Sox 2, Oct 3/4 and Nanog (F) as well as of Δ133p53 (α, β and γ) and p53 β isoforms (p53 TAB, Δ40p53β, Δ133p53β, and Δ160p53β) (G) after transduction with Sh1 and Sh2 (n=4).

P53 isoforms are presented in FIG. 1A.

In addition, Table 1 below provides amino acids and nucleic acid sequences of full-length p53 (denoted as "p53"), and of Δ133p53β and Δ133p53γ isoforms.

TABLE 1

Amino acids and nucleic acid sequences of full-length p53 (denoted as "p53"), and of Δ133p53β and Δ133p53γ isoforms.

| Isoform | Amino acids sequence (SEQ ID NO:/Genbank accession number) | Nucleic acid sequence (SEQ ID NO:/Genbank accession number) |
| --- | --- | --- |
| Δ133p53β | SEQ ID NO: 1/ NP_001119588.1 | SEQ ID NO: 2/ NM_001126116.1 |
| Δ133p53γ | SEQ ID NO: 3/ NP_001119589.1 | SEQ ID NO: 4/ NM_001126117.1 |
| p53 | SEQ ID NO: 5/ NP_000537.3 | SEQ ID NO: 6/ NM_000546.4 |

Cancer, Cancer Stem Cells, Chemotherapeutic Anti-Cancer Treatments, Anti-Cancer Stem Cells Agents In the present description, "cancer" refers to a malignant neoplasm characterized by deregulated or uncontrolled cell growth. In particular, a "cancer cell" refers to a cell with deregulated or uncontrolled cell growth.

The term "cancer" includes primary malignant tumours (e.g., those whose cells have not migrated to sites in the subject's body other than the site of the original tumor) and secondary malignant tumours (e. g., those arising from metastasis, the migration of tumour cells to secondary sites that are different from the site of the original tumour). Such cancer may notably be selected from the group of solid cancers, and in particular from the group consisting of breast cancer, colorectal cancer ovarian cancer, digestive cancers (also referred as gastrointestinal cancer including colorectal cancer, oesophageal cancer, gastric cancer, pancreatic cancer, hepatocellular carcinoma, cholangiocellular cancer and teratocarcinoma), pancreatic cancer and throat cancer, particularly of human subject, the more preferred is breast cancer, a colorectal cancer gastrointestinal cancer, lung cancer and prostate cancer, and even more preferably a breast cancer or a colorectal cancer. Such cancer may also be selected from the group of hematopoietic cancers, and in particular from the group consisting of leukaemias and lymphomas, particularly of human subject.

In the present description, "cancer relapse" refers to the return of the cancer or the signs and symptoms thereof after a period of improvement.

By "cancer sample", it is meant any sample comprising cancer cells, including but not limited to a cancer biopsy or a complete or partial cancer surgical resection, or a blood sample. Indeed, it is well known in the art that circulating cancer cells are present in blood.

By "untreated cancer sample" is meant a cancer sample that has not been treated with a chemotherapeutic anti-cancer agent. In contrast, by "treated cancer sample" is meant a cancer sample that has been treated with a chemotherapeutic anti-cancer agent.

By "non-cancerous cell sample" it is meant any sample comprising or supposed to comprise a healthy non cancer cells including but not limited to tissue biopsy or blood sample.

In the present description, a "chemotherapeutic anti-cancer agent" refers to any chemical drug used for anticancer therapy. Chemotherapeutic anti-cancer agent may be any one of those listed by the American Cancer Society. Such chemotherapeutic anti-cancer agent notably includes any of the following conventional anti-cancer treatments: topoisomerase II inhibitors (including etoposide, tenoposide, doxorubicine, daunorubicin, mitoxantrone, and amsacrine), anti-tubuline agent (including taxanes such as paclitaxel and docetaxel; and vinca alkaloids such as vinblastine, vincristine, vindesine, and vinorelbine), antimetabolites (such as pyrimidine analogue 5-Fluorouracil (5-FU).

In the present description, a "cancer stem cells" (abbreviated as "CSCs") refers to cancer cells with features associated to normal stem cells, such as the ability to give rise to all cell types found in a particular cancer sample. CSCs are also characterized by the expression of transcription factors specifically expressed in stem cells, such as Oct 3/4, Nanog and Sox 2; the ability to form spheres in appropriate conditions; the presence of side populations (SP); and/or the expression or non-expression of surface markers associated to cancer stem cells. Based on the teachings of Tirino et al., 2013, surface phenotype, detection of side-population (SP) phenotypes by Hoechst 33342 exclusion, of sphere-forming ability, and/or detection of aldehyde dehydrogenase (ALDH) activity of various cancer stem cells are disclosed in Table 2a below.

TABLE 2a surface phenotype, detection of side-population (SP) phenotypes by Hoechst 33342 exclusion, of sphere-forming ability, and/or detection of aldehyde dehydrogenase (ALDH) activity of various cancer stem cells as disclosed in Tirino et al., 2013.

| Tumor type | CSC surface phenotype | Detection of SP phenotypes | Sphere-forming ability | ALDH activity |
|---|---|---|---|---|
| Breast cancer | $CD44^+CD24^{-/low}$/ | | Yes | / |
| Glioblastoma | $CD133^+$ | / | Yes | / |
| Melanoma | $CD20^+$ | / | Yes | / |
| Prostate cancer | $CD44^+/\alpha_2\beta_1^{hi}$/ $CD133^+$ | / | Yes | / |
| Ovarian cancer | / | Yes | Yes | / |
| Gastric cancer | $CD44^+$ | Yes | / | / |
| Lung cancer | $CD133^{+,}$ | Yes | Yes | / |
| HNSCC | $CD44^+$ | / | / | / |
| Osteosarcoma | $CD133^+$, $CD117^+$, $Stro-1^+$ | Yes | Yes | Yes |
| Chondrosarcoma | $CD133^+$ | Yes | Yes | / |
| Synovial sarcoma | $CD133^+$ | / | / | / |
| Ewing's sarcoma | $CD133^+$ | / | / | Yes |
| Rhabdomyosarcoma | $CD133^+$ | / | / | / |
| Mesenchymal neoplasms | / | Yes | / | / |

HNSCC: head and neck squamous cell carcinoma.

TABLE 2b below shows cell surface phenotype of CSC identified in hematological malignancies:

| Tumor type | Cell surface markers |
|---|---|
| AML (acute myeloid leukemia) | $CD34^+CD38^-$ $CD34^+CD38^-$ $CD34^+CD38^-$ |
| B-ALL (acute lymphoblastic leukemia) | $CD34^+CD10^-/CD34^+CD19^-$ $CD34^+CD38^-CD19^+$ |
| Multiple Myeloma | $CD34^-CD138^-$ |
| T-ALL (acute lymphoblastic leukemia) | $CD34^+CD4^-/CD34^+CD7^-$ |

Table 2b: surface phenotype detection summarized by Schatton et al. (2009).

In order to experimentally check the "stemness" of a given cancer cell population, often rely on xenotransplantation assays in immunocompromised mice using human tumor biopsy-derived cancer subpopulations sorted for the presence or absence of a particular candidate CSC marker or set of markers as indicated above (Schatton et al., 2009). Cancer stem cell may by also defined by xenotransplantation in zebrafish (Dovey et al., 2009).

Traditionally, CSCs have also been identified through sphere formation in cell culture with matrigel or extra-low attachment conditions (Le Cheng et al, 2009).

In the present description, "sphere", "spheroid" or "tumorsphere" refers to a solid, spherical formation developed from the proliferation of one cancer cell. Such spheres are easily distinguishable from single or aggregated cells as the cells appear to become fused together and individual cells cannot be identified. Their size may vary between 50 and 250 µm. The ability to form spheres is considered to be associated to the presence of cancer stem cells. Such spheres as defined in the present invention are distinct from commonly known blebbes, as defined for example by Charras (2008). In particular, blebs are protrusions of the cell membrane of one cell which are the result of actomyosin contraction of the cortex causing either transient detachment of the cell membrane from the actin cortex or a rupture in the actin cortex. In contrast, the spheres are formed by the aggregation of several cells.

In addition to the surface markers defined in Tables 2a and 2b above for CSCs of various origin, CSCs generally also express surface markers of normal stem cells, such as the carbohydrate epitopes TRA-1-60 and TRA-1-81 recognized by commercially available anti-TRA-1-60 and anti-TRA-1-81 monoclonal antibodies.

As used herein, a "therapeutically efficient amount" refers to an amount sufficient for the intended use. For a chemotherapeutic anti-cancer agent, it refers to an amount sufficient to reduce cancer growth or spreading. For an agent reducing Δ133p53β or Δ133p53γ isoform expression, it refers to an amount sufficient to significantly reduce Δ133p53β or Δ133p53γ isoform expression level.

Vectors

A "plasmid vector" as used herein refers to a replicable DNA construct.

The term "viral vector" as used herein refers to a nucleic acid vector that includes at least one element of a virus genome and may be packaged into a viral particle. The terms "virus", "virions", "viral particles" and "viral vector particle" are used interchangeably to refer to viral particles that are formed when the nucleic acid vector is transduced into an appropriate cell or cell line according to suitable conditions allowing the generation of viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or subject. As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. mRNA).

Other Definitions

In the present description, the term "subject" refers to mammals, e. g., humans, dogs, cows, horses, kangaroos, pigs, sheep, goats, cats, mice, rabbits, rats, and transgenic non-human animals. In preferred embodiments of the present invention, a subject is a human subject, and more preferably a woman in the context of breast cancer.

In the present description, the expression "measured in vitro" means that the expression level is not known (it cannot be merely retrieved from a database) and has to be physically measured by some treatment step, which is performed in a laboratory.

The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 10 to 25 or more nucleotides, depending upon the complexity of the target sequence, although it may contain fewer nucleotides.

Method for Producing Cancer Stem Cells

In the context of the present invention, the inventors have found that Δ133p53β isoform (and also Δ133p53γ to a lesser extent), but not Δ133p53α isoform (also referred to as Δ133p53 isoform), is not only a marker of a risk of cancer metastasis, but actually promotes cancer stem cell phenotype. In particular, expression of Δ133p53β isoform (and also Δ133p53γ to a lesser extent), but not of Δ133p53α isoform (also referred to as Δ133p53 isoform), promotes cancer cell sphere-forming activity, and also promotes Sox 2, Oct 3/4 and Nanog expression (but not c-Myc), transcription factors known to be useful of reprogramming cells towards pluripotency.

This finding is very important since it provides a mean for producing high numbers of CSCs, thus permitting to study and better understand their biology, a crucial point for improving anticancer therapies.

In a first aspect, the present invention thus relates to a method for producing cancer stem cells, comprising:
  a) transducing cancer cells with a vector expressing Δ133p53β isoform, Δ133p53γ isoform, or both Δ133p53β and Δ133p53γ isoforms;
  b) culturing transduced cancer cells in a medium supporting expansion of transduced cancer cells; and
  c) isolating cancer stem cells.

Cancer Cells

In the method for producing cancer stem cells of the present invention, cancer cells are preferably selected from the group of solid cancer cells, and in particular from the group consisting of breast cancer cells, colorectal cancer cells ovarian cancer cells, digestive cancers cells (also referred as gastrointestinal cancer including colorectal cancer, oesophageal cancer, gastric cancer, pancreatic cancer, hepatocellular carcinoma, cholangiocellular cancer and teratocarcinoma), pancreatic cancer cells and throat cancer cells, particularly of human subject, more preferably cancer cells are selected from breast cancer cells colorectal cancer cells, gastrointestinal cancer cells, lung cancer cells and prostate cancer cells and even more preferably cancer cells are breast cancer cells or colorectal cancer cells.

Moreover, the cancer cells may be selected from the group of hematopoietic cancer cells, and in particular from the group consisting of leukaemia cells and lymphoma cells. Preferably, the hematopoietic cancer cells are human hematopoietic cancer cells. It is known in the art that many types of cancer cells, when transduced by at least one and preferably several of Yamanaka factors (Oct 3/4, Nanog, Sox 2 and c-Myc), may give rise to CSCs. Examples of cancer cells in which this has been shown include:
  colon (or colorectal) cancer cells (see for instance Oshima et al (2014), which describes that colon cancer cells transduced with factors Oct 3/4, Sox 2 and KLF4 showed significantly enhanced CSCs proprieties in terms of marker gene expression and sphere formation),
  gastrointestinal cancer cells (including cells of colorectal cancer, oesophageal cancer, gastric cancer, pancreatic cancer, hepatocellular carcinoma, cholangiocellular cancer and teratocarcinoma). Miyoshi et al (2010) disclose that cells obtained from the above cited gastrointestinal cancers induced with Nanog transcriptional factor manifest a pluripotency like CSCs, lung cancer cells (see Chiou et al., 2010, which describes that ectopic expression of Oct4 and Nanog transcriptional factors in lung adenocarcinoma cells induce the sphere formation), and prostate cancer cells (see Jeter et al, 2011, which describes that tetracycline-inducible Nanog-overexpression in prostate cancer cell lines promotes tumour regeneration by enhancing the expression of several CSCs associated molecules.

Since transduction with Δ133p53β isoform or Δ133p53γ isoform induces the expression of Sox 2, Nanog and Oct 3/4, its transduction in any cancer cell known to give rise to CSCs when transduced by at least one and preferably several of Yamanaka factors (Oct 3/4, Nanog, Sox 2 and c-Myc) is expected to generate CSCs. This has been demonstrated by the inventors for two distinct types of cancer cells: breast and colon cancer cells. Such cancer cells may be obtained from any cancer sample, including a cancer biopsy, a complete or partial cancer surgical resection, or a blood sample. Indeed, cancer cells (including cancer stem cells) are well known to circulate in blood (Mavroudis-2010; Alix-Panabières et al,. 2013).

Isoform

In a preferred embodiment of the method for producing cancer stem cells according to the invention, it is the Δ133p53β isoform or both Δ133p53β and Δ133p53γ isoforms (preferably only the Δ133p53β isoform) that is/are transduced in cancer cells in step b). Indeed, expression of Δ133p53β isoform is particularly associated to induction of cancer stem cells.

Vector Expressing Δ133p53β Isoform, Δ133p53γ Isoform, or Both Δ133p53β and Δ133p53γ Isoforms (Step b)

Any appropriate vector expressing Δ133p53β isoform, Δ133p53γ isoform, or both Δ133p53β and Δ133p53γ isoforms may be used.

A suitable vector comprises a nucleic acid molecule encoding Δ133p53β isoform, Δ133p53γ isoform, or both Δ133p53β and Δ133p53γ isoforms and elements necessary to allow expression thereof.

Suitable vectors notably include plasmid vectors and viral vectors.

Viral vectors can be replication-competent or-selective (e.g. engineered to replicate better or selectively in specific host cells), or can be genetically disabled so as to be replication-defective or replication-impaired. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them.

In an embodiment, a plasmid vector expressing Δ133p53β isoform, Δ133p53γ isoform, or both Δ133p53β and Δ133p53γ isoforms is used.

Representative examples of suitable plasmid vectors include, without limitation, pREP4, pCEP4 (Invitrogen), pCI (Promega), pVAX (Invitrogen) and pGWiz (Gene Therapy System Inc).

For transduction, a plasmid vector may be complexed to lipids or polymers to form particulate structures such as liposomes, lipoplexes or nanoparticles.

In a preferred embodiment, a viral vector expressing Δ133p53β isoform, Δ133p53γ isoform, or both Δ133p53β and Δ133p53γ isoforms is used (i.e a viral vector comprising a nucleic acid molecule encoding Δ133p53β isoform, Δ133p53γ isoform, or both Δ133p53β and Δ133p53γ isoforms and elements necessary to allow expression thereof). Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatis virus, etc). As described above, the term "viral vector" encompasses vector DNA, genomic DNA as well as viral particles generated thereof, and especially infectious viral particles.

In a preferred embodiment, a retroviral vector expressing Δ133p53β isoform, Δ133p53γ isoform, or both Δ133p53β and Δ133p53γ isoforms isoform is used (i.e a retroviral vector comprising a nucleic acid molecule encoding Δ133p53β isoform, Δ133p53γ isoform, or both Δ133p53β and Δ133p53γ isoforms and elements necessary to allow expression thereof).

Retroviruses have the property of infecting, and in most cases integrating into, dividing cells and in this regard are particularly appropriate for use in the context of the present invention for producing cancer stem cells. A suitable retrovirus generally contains the LTR sequences, an encapsidation region and a nucleic acid molecule encoding Δ133p53β or Δ133p53γ isoform. The recombinant retrovirus can be derived from a retrovirus of any origin (murine, primate, feline, human, etc.) and in particular from the MoMuLV (Moloney murine leukemia virus), MVS (Murine sarcoma virus), Friend murine retrovirus (Fb29), Murine Embryonic Stem Cell Virus (MESV), LN virus or Murine Stem Cell Virus (MSCV). It is propagated in an encapsidation cell line which is able to supply in trans the viral polypeptides gag, pol and/or env which are required for constituting a viral particle. Such cell lines are described in the literature (PA317, Psi CRIP GP +Am-12, HEK 293T etc.). The retroviral vector according to the invention can contain modifications, in particular in the LTRs (replacement of the promoter region with a eukaryotic promoter) or the encapsidation region (replacement with a heterologous encapsidation region).

In a particularly preferred embodiment, the vector used for transducing cancer cells in step b) is a Murine Stem Cell Virus (MSCV), which is derived from the Murine Embryonic Stem Cell Virus (MESV) and the LN retroviral vectors (Grez, M., et al. 1990; Miller, A. D. et al. 1989). Notably, the transducing vector may be obtained by cloning a molecule encoding Δ133p53β isoform, Δ133p53γ isoform, or both Δ133p53β and Δ133p53γ isoforms into a pMSCV vector commercialized by Clontech, such as pMSCVhyg, pMSCVneo, or pMSCVpuro.

However, other types of viral vectors expressing Δ133p53β isoform, Δ133p53γ isoform, or both Δ133p53β and Δ133p53γ isoforms may be used.

Examples of viral vectors that are useful in the context of the invention include adenoviral vectors, which may be derived from a variety of human or animal sources (e.g. canine, ovine, simian adenovirus, etc). Any serotype can be employed with a special preference for human adenoviruses and a specific preference for subgenus C such as Ad2, Ad5, Ad6, and subgenus B such as Ad11, Ad34 and Ad35. The cited adenovirus are available from ATCC or have been the subject of numerous publications describing their sequence, organization and methods of producing, allowing the artisan to apply them. When an adenoviral vector is used, it is preferably an E1-defective adenoviral vector with an E1 deletion extending from approximately positions 459 to 3328 or from approximately positions 459 to 3510 (by reference to the sequence of Ad5 disclosed in the GenBank under the accession number M73260.1). The cloning capacity can further be improved by deleting additional portion(s) of the adenoviral genome (all or part of the non-essential E3 region (e.g. deletion from approximately positions 27867 to 30743) or of other essential E2 and/or E4 regions. The nucleic acid molecule encoding Δ133p53β isoform, Δ133p53γ isoform, or both Δ133p53β and Δ133p53γ isoforms can then be inserted in any location of the adenoviral genome, with a specific preference for insertion in replacement of the E1 and/or E3 region. They may be positioned in sense or antisense orientation relative to the natural transcriptional direction of the region in question.

Other examples of viral vectors that may be used in the context of the invention include poxvirus vectors such as fowlpox vectors (e.g. FP9), canarypox vectors (e.g. ALVAC) and vaccinia virus vectors, the latter being preferred. Suitable vaccinia viruses include without limitation the Copenhagen strain, the Wyeth strain, NYVAC and the modified Ankara (MVA) strain. The general conditions for constructing and producing recombinant poxvirus are well known in the art. The nucleic acid molecule encoding Δ133p53β isoform, Δ133p53γ isoform, or both Δ133p53β and Δ133p53γ isoforms is preferably inserted within the poxviral genome in a non-essential locus. Thymidine kinase gene is particularly appropriate for insertion in Copenhagen vaccinia vectors and deletion II or III for insertion in MVA vector.

Other viral vectors suitable in the context of the invention are morbillivirus which can be obtained from the paramyxoviridae family, with a specific preference for measles virus. Insertion of the nucleic acid molecule encoding Δ133p53β isoform, Δ133p53γ isoform, or both Δ133p53β and Δ133p53γ isoforms between P and M genes or between H and L genes is particularly appropriate.

In the above vectors, the nucleic acid molecule encoding Δ133p53β isoform, Δ133p53γ isoform, or both Δ133p53β and Δ133p53γ isoforms are in a form suitable for expression in cancer cells, which means that each of the nucleic acid molecules set forth herein is operably linked to appropriate regulatory sequences.

It will be appreciated by those skilled in the art that the choice of the regulatory sequences can depend on such factors as the vector itself and the cancer cells to be transduced, and will be easily selected by those skilled in the art based on common general knowledge and publications on this topic. Suitable promoters for constitutive expression in eukaryotic systems include viral promoters, such as SV40 promoter, the cytomegalovirus (CMV) immediate early promoter or enhancer, the adenovirus early and late promoters, the thymidine kinase (TK) promoter of herpes simplex virus (HSV)-1 and retroviral long-terminal repeats (e.g. MoMuLV and Rous sarcoma virus (RSV) LTRs) as well as cellular promoters such as the phosphoglycero kinase (PGK) promoter. Examples of suitable promoters for a Murine Stem Cell Virus (MSCV) vector include those present in pMSCV vector commercialized by Clontech, such as pMSCVhyg, pMSCVneo, or pMSCVpuro.

Culture of Transduced Cancer Cells (Step b)

In step b), transduced cancer cells are cultured in a medium supporting their expansion. Such a medium may be a basal medium (comprising inorganic salts, amino acids, vitamins and glucose, such as DMEM), which may be supplemented with a reducing agent (such as B-mercaptoethanol), at least one antibiotic (such as Penicillin-Streptomycin), and/or at least one growth factor able to sustain expansion of the type of cancer cells transduced (including, but not limited to, Epidermal Growth Factor (EGF) and/or basic Fibroblast Growth Factor (bFGF)).

For breast cancer cells and more generally cancer cells of epithelial origin (cancer cells derived from a carcinoma), a preferred medium in step b) may contain a basal medium comprising inorganic salts, amino acids, vitamins and glucose, B-mercaptoethanol, at least one antibiotic, and bFGF.

Step b) is performed for a period sufficient in order to recover cancer stem cells from the transduced cancer cell culture. A suitable period should be optimized for each type of cancer cells, but will generally be between 3 and 21 days, in particular between 7 and 14 days.

Isolation of Cancer Stem Cells (Step c)

In step c), cancer stem cells are isolated from the transduced cancer cells culture.

In the transduced cancer cells culture, cancer stem cells may be isolated based on selection of any feature specific to cancer stem cells compared to other cancer cells.

In particular, depending on the type of cancer cells, CSCs can be identified and isolated by means of at least one of the 4 following methods:
  i) isolation according to CSC-specific cell surface markers;
  ii) isolation by flow cytometry based on side-population (SP) phenotype by DNA dye exclusion;
  iii) isolation by flow cytometry based on high aldehyde dehydrogenase (ALDH) activity; and
  iv) submission to sphere-forming assay and collection of spheres.

The suitability of the four above mentioned methods may notably be determined by those skilled in the art depending on the type of cancer cells based on information provided above in the definitions of cancer stem cells (and in particular in Tables 2a and 2b).

In method i), CSCs are isolated based on CSC-specific cell surface markers. In this method, transduced cancer cells are stained using antibodies directed to one or more CSC-specific cell surface markers, and cells having the desired surface marker phenotype are sorted. Those skilled in the art know how to implement such siolation based on surface cell markers. For instance, flow cytometry cell-sorting may be used, transduced cancer cells are directly or indirectly fluorescently stained with antibodies directed to one or more CSC-specific cell surface markers and cells by detected by flow cytometer laser as having the desired surface marker phenotype are sorted. In another embodiment, magnetic separation may be used. In this case, antibody labelled transduced cancer cells (which correspond to CSCs if an antibody directed to a CSC marker is used, or to non-CSC if an antibody specifically not expressed by CSCs is used) are contacted with magnetic beads specifically binding to the antibody (for instance via avidin/biotin interaction, or via antibody-antigen binding) and separated from antibody non-labelled transduced cancer cells. Several rounds of magnetic purification may be used based on markers specifically expressed and non-expressed by CSCs.

In method ii), CSCs are isolated by flow cytometry cell-sorting based on DNA dye side population (SP) phenotype. This method is based on the passive uptake of cell-permeable DNA dyes by live cells and pumping out of such DNA dyes by a side population of stem cells via ATP-Binding Cassette (ABC) transporters allowing the observation of a side population that has a low DNA dye fluorescence at the appropriate wavelength. ABC pumps can be specifically inhibited by drugs such as verapamil (100 μM final concentration) or reserpine (5 μM final concentration), and these drugs may be used to generate control samples, in which no SP phenotype may be detected. Appropriate cell-permeable DNA dyes that may be used include Hoechst 33342 (the main used DNA dye for this purpose, see Golebiewska et al., 2011) and Vybrant® DyeCycle™ stains available in various fluorescences (violet, green, and orange; see Telford et al-2010).

In method iii), CSCs are isolated by flow cytometry cell-sorting based on high ALDH activity. Indeed, several types of CSCs have been characterized as displaying high ALDH activity. In this method, transduced cancer cells are incubated with a fluorescent ALDH substrate, which freely diffuses into intact and viable cells (such as the BODIPY™-aminoacetaldehyde (BAAA) reagent of ALDEFLUOR™ kit commercialized by Stemcell Technologies). In the presence of ALDH, this fluorescent substrate is converted into a fluorescent metabolite (such as the BODIPY™-aminoacate (BAA) reagent obtained from BODIPY™-BAAA in the ALDEFLUOR™ kit commercialized by Stemcell Technologies), which is retained inside the cells. The amount of fluorescent reaction product is proportional to the ALDH activity in the cells and is measured using a flow cytometer. Viable ALDH$^{bright}$ (ALDH$_{br}$) cells can, in principle, be isolated using a cell sorter. Active efflux of the reaction product is inhibited by an efflux inhibitor in the ALDEFLUOR™ Assay Buffer. A specific inhibitor of ALDH, such as diethylaminobenzaldehyde (DEAB), is used to control for background fluorescence.

In method iv), CSCs are isolated by submitting transduced cancer cells to sphere-forming assay and collecting spheres. This method relies on the preferential ability of cancer stem cells to form spheres under serum-free (and preferably low adherence) culture conditions, whereas bulk tumor cells are less likely to be able to form spheres under the same conditions. A suitable sphere-forming assay for isolation of CSCs may comprise:

1) resuspending transduced cancer cells into a serum-free medium, preferably in the presence of specific growth factors (including, but not limited to, Epidermal Growth Factor (EGF) and basic Fibroblast Growth Factor (bFGF)), and plating them into tissue culture dishes, to which mammalian cells preferably poorly adhere;
2) incubating the cancer cells during 5 to 20 days; and
3) collecting spheres.

In step 1), cancer cells are resuspended into a serum-free medium (e.g., MammoCult®, available from StemCell Technologies, Inc., Vancouver, Canada), preferably in the presence of specific growth factors such as EGF and bFGF, and plated into tissue culture dishes. Preferably, tissue culture dishes to which mammalian cells poorly adhere are selected (e.g. Ultra Low Cluster Plate, 24-well, Flat Bottom from Corning Inc). In this step, the seeding density is preferably kept between 250 and 2500 cells/cm$^2$, and is preferably optimized for each type of cancer cells.

For instance, for breast cancer cells in MammoCult™ Medium enriched with MammoCult™Proliferation Supplements, hydrocortisone and heparin (Stem Cell Technologies), a seeding density of 500 cells/well of Ultra Low Cluster Plate, 24-well, Flat Bottom (Corning Inc) is appropriate.

In step 2), cancer cells are incubated, preferably at about 37° C. under 5% $CO_2$ atmosphere, during 5 to 20 days, preferably during 7 to 15 days.

Finally, in step 3), spheres at least 50 μm large that have formed during incubation are collected.

The isolated CSCs obtained using one of the above described methods may be then optionally be tested by using a xenotransplantation test. In this case, the isolated subpopulation of CSCs is submitted to serial transplantations into immunocompromised mice (for example SCID mice, see Schatton et al., 2009) or zebrafishes (see Dovey et al., 2009), preferably into immunocompromised mice (for example SCID mice). After transplantation of the CSCs population, the resulting tumor is expected to mirror the phenotypic heterogeneity of the original tumor and contain CSCs with preserved ability to self-renew in subsequent serial transplantations (Le Cheng, 2009).

Preferred Embodiments

Various preferred specific features corresponding to various generic elements of the method for producing cancer stem cells according to the invention have been described above in the section specifically relating to this element. In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the method for producing cancer stem cells according to the invention may be combined with any generic other element or with preferred embodiments of said other element.

Preferred embodiments correspond to those in which at least one element is limited to a preferred embodiment, as listed in Table 3 below:

TABLE 3

Preferred embodiment of various elements of the method for producing cancer stem cells according to the invention.

| Element | Preferred embodiment(s) |
|---|---|
| Cancer cell | Breast cancer cell or colorectal cancer cells |
| P53 isoform transduced in cancer cells | Δ133p53β isoform or Δ133p53β and Δ133p53γ isoforms, preferably Δ133p53β isoform |
| Type of vector used for transducing Δ133p53β isoform, Δ133p53γ isoform, or both Δ133p53β and Δ133p53γ isoforms | Retroviral vector, preferably Murine Stem Cell Virus (MSCV) vector |
| Medium for culture of transduced cancer cells | basal medium comprising inorganic salts, amino acids, vitamins and glucose, β-mercaptoethanol, at least one antibiotic, and bFGF |
| Collection of cancer stem cells | Selection based on surface markers or sphere-forming ability. |

In a particularly preferred embodiment of the method for producing cancer stem cells according to the invention, cancer cells used for transduction are breast cancer cells, the P53 isoform transduced in cancer cells is Δ133p53β isoform and is transduced using a Murine Stem Cell Virus (MSCV) vector, the medium used in step b) is a basal medium comprising inorganic salts, amino acids, vitamins and glucose, B-mercaptoethanol, at least one antibiotic, and bFGF, and cancer stem cells are isolated in step c) by selection based on surface markers or sphere-forming ability.

Prediction of the Risk that a Chemotherapeutic Anti-Cancer Treatment Induces Cancer Stem Cells in a Subject Suffering from Cancer The inventors further surprisingly found that anticancer treatment of cancer cells expressing Δ133p53β isoform by etoposide (a topoisomerase II inhibitor) is not only inefficient (resistance to treatment) but further promotes cancer stemness by increasing Δ133p53β expression level. As a result, treating cancer patients with Δ133p53γ-expressing would promote CSC formation and would thus be rather deleterious than useful.

The present invention thus also relates to a method for predicting the risk that treatment with a chemotherapeutic anti-cancer agent induces cancer stem cells in a subject suffering from cancer from a cancer sample of said subject, comprising:
 a) measuring in vitro the expression level of Δ133p53β isoform, Δ133p53γ isoform, or both Δ133p53β and Δ133p53γ isoforms in said cancer sample, untreated with the chemotherapeutic anti-cancer agent;
 b) treating said cancer sample with said chemotherapeutic anti-cancer agent;
 c) measuring in vitro the expression level of Δ133p53β isoform, Δ133p53γ isoform, or both Δ133p53β and Δ133p53γ isoforms in the treated cancer sample;
 d) comparing the values obtained in steps a) and c); and
 e) concluding to:
   (i) the presence of a significant risk that treatment with said chemotherapeutic anti-cancer agent induces cancer stem cells in said subject if the expression level of Δ133p53β isoform, Δ133p53γ isoform, or both Δ133p53β and Δ133p53γ isoforms measured in step c) is higher than the expression level of Δ133p53β isoform, Δ133p53γ isoform, or both Δ133p53β and Δ133p53γ isoforms measured in step a), or
   (ii) the absence of a significant risk that treatment with said chemotherapeutic anti-cancer agent induces cancer stem cells in said subject if the expression level of Δ133p53β isoform, Δ133p53γ isoform, or both Δ133p53β and Δ133p53γ isoforms measured in step c) is lower than or equal to the expression level of Δ133p53β isoform, Δ133p53γ isoform, or both Δ133p53β and Δ133p53γ isoforms measured in step a).

Chemotherapeutic Anti-Cancer Treatment

In the method of prediction of the risk that a chemotherapeutic anti-cancer treatment induces cancer stem cells according to the invention, the chemotherapeutic anti-cancer agent susceptible to induce cancer stem cells in a cancer subject is preferably selected from:
 a topoisomerase II inhibitor, including etoposide, etoposide, tenoposide, doxorubicine, daunorubicin, mitoxantrone, and amsacrine;
 an anti-tubuline agent, including taxanes such as paclitaxel and docetaxel, and vinca alkaloids such as vinblastine, vincristine, vindesine, and vinorelbine;
 antimetabolites, including pyrimidine analogue 5-Fluorouracil (5-FU).

In a preferred embodiment, the chemotherapeutic anti-cancer treatment susceptible to induce cancer stem cells in a cancer subject is a topoisomerase II inhibitor, in particular selected from etoposide, tenoposide, doxorubicine, daunorubicin, mitoxantrone, and amsacrine. More preferably, the chemotherapeutic anti-cancer treatment susceptible to induce cancer stem cells in a cancer subject is etoposide.

Cancer and Cancer Sample

In the method of prediction of the risk that a chemotherapeutic anti-cancer treatment induces cancer stem cells according to the invention, the cancer from which the subject is suffering is preferably selected from the group of solid cancers, and in particular from the group consisting of breast cancer, colorectal cancer, ovarian cancer, digestive cancers (also referred as gastrointestinal cancer, including colorectal cancer, oesophageal cancer, gastric cancer, pancreatic cancer, hepatocellular carcinoma, cholangiocellular cancer and teratocarcinoma), pancreatic cancer, lung cancer, prostate cancer and throat cancer, particularly of human subject, more preferably breast cancer colorectal cancer, gastrointestinal cancer, lung cancer and prostate cancer and even more preferably the cancer from which the subject is breast cancer or colorectal cancer.

Moreover, the cancer may be selected from the group of hematopoietic cancers, and in particular from the group consisting of leukaemias and lymphomas. Preferably, the hematopoietic cancer is a human hematopoietic cancer.

It is known in the art that many types of cancer cells, when transduced by at least one and preferably several of Yamanaka factors (Oct 3/4, Nanog, Sox 2 and c-Myc), may give rise to CSCs. Examples of cancer cells in which this has been shown include:
 colon (or colorectal) cancer cells (see for instance Oshima et al (2014), which describes that colon cancer cells transduced with factors Oct 3/4, Sox 2 and KLF4 showed significantly enhanced CSCs proprieties in terms of marker gene expression and sphere formation),
 gastrointestinal cancer cells (including cells of colorectal cancer, oesophageal cancer, gastric cancer, pancreatic cancer, hepatocellular carcinoma, cells obtained from the above cited gastrointestinal cancers induced with Nanog transcriptional factor manifest a pluripotency like CSCs,
 lung cancer cells (see Chiou et al., 2010, which describes that ectopic expression of Oct4 and Nanog transcriptional factors in lung adenocarcinoma cells induce the sphere formation), and
 prostate cancer cells (see Jeter et al, 2011, which describes that tetracycline-inducible Nanog-overexpression in prostate cancer cell lines promotes tumour regeneration by enhancing the expression of several CSCs associated molecules.

Since transduction with Δ133p53β isoform or Δ133p53γ isoform induces the expression of Sox 2, Nanog and Oct 3/4, its transduction in any cancer cell known to give rise to CSCs when transduced by at least one and preferably several of Yamanaka factors (Oct 3/4, Nanog, Sox 2 and c-Myc) is expected to generate CSCs. This has been demonstrated by the inventors for two distinct types of cancer cells: breast and colon cancer cells.

The cancer sample from which the expression level of Δ133p53β isoform, Δ133p53γ isoform, or both Δ133p53β and Δ133p53γ isoforms is measured in step a) may be a cancer biopsy or a complete or partial cancer surgical resection. Alternatively, the cancer sample from which the expression level of Δ133p53β isoform, Δ133p53γ isoform, or both Δ133p53β and Δ133p53γ isoforms is measured in step a) may be a blood sample. Indeed, cancer cells (including cancer stem cells) are well known to circulate in blood (Mavroudis—2010; Alix-Panabières et al,. 2013), and expression of Δ133p53β isoform, Δ133p53γ isoform, or both Δ133p53β and Δ133p53γ isoforms may thus also be detected in a blood sample of a cancer patient. The skilled artisan knows from Anensen et al. (2006) that p53 isoforms may be measured in the blood.

Isoform

In a preferred embodiment of the method of prediction of the risk that a chemotherapeutic anti-cancer treatment induces cancer stem cells according to the invention, it is the expression level of Δ133p53β isoform or both Δ133p53β and Δ133p53γ isoforms that is measured in step a). Indeed, expression of Δ133p53β isoform is particularly associated to induction of cancer stem cells in a cancer subject treated with a chemotherapeutic anti-cancer treatment.

Steps a) and c)—Measure of the Expression Level of Δ133p53β Isoform, Δ133p53γ Isoform, or Both Δ133p53β and Δ133p53γ Isoforms in Untreated (Step a)) or Treated (Step c)) Cancer Cells In step a), the expression level of Δ133p53β isoform, Δ133p53γ isoform, or both Δ133p53β and Δ133p53γ isoforms is measured in vitro in a cancer sample from the subject that has not been treated with the chemotherapeutic anti-cancer agent.

In step c), the expression level of Δ133p53β isoform, Δ133p53γ isoform, or both Δ133p53β and Δ133p53γ isoforms is measured in vitro in the cancer sample from the subject, which has been further treated with the chemotherapeutic anti-cancer agent.

In some embodiments, the method of prediction of the risk that a chemotherapeutic anti-cancer treatment induces cancer stem cells according to the invention may further comprise a preliminary step a1) of taking a cancer sample from the subject.

In addition, step a), step c) or both may further comprise preliminary substeps of transformation of the untreated and treated cancer sample, which may vary depending if the expression level of Δ133p53β isoform, Δ133p53γ isoform, or both Δ133p53β and Δ133p53γ isoforms is measured at the protein or nucleic acid level.

Since the expression level of Δ133p53β isoform, Δ133p53γ isoform, or both Δ133p53β and Δ133p53γ isoforms has to be measured in a cancer sample of the subject both before and after treatment with the chemotherapeutic anti-cancer agent, and since the measure may involve preliminary substeps of transformation of the untreated and treated cancer sample, the initial cancer sample may be divided in several parts, one part being used for measuring the expression level of Δ133p53β isoform, Δ133p53γ isoform, or both Δ133p53β and Δ133p53γ isoforms before treatment with the chemotherapeutic anti-cancer agent in step a), another part being used for measuring the expression level of Δ133p53β isoform, Δ133p53γ isoform, or both Δ133p53β and Δ133p53γ isoforms after treatment with the chemotherapeutic anti-cancer agent in step c). The initial cancer sample will then be divided so that all parts be as much similar as possible (number and types of cells present in the sample), in order to prevent or reduce to the minimal any bias due to sampling.

Measure at the Protein Level

In an embodiment of the method of prediction of the risk that a chemotherapeutic anti-cancer treatment induces cancer stem cells according to the invention, the expression levels of Δ133p53β isoform, Δ133p53γ isoform, or both Δ133p53β and Δ133p53γ isoforms in said untreated and treated cancer sample are measured at the protein level.

In this case, preliminary substeps of transformation of the untreated and treated cancer sample may include a substep of extraction of proteins present in the cancer sample, for further measure of the amount of Δ133p53β, Δ133p53γ, or both Δ133p53β and Δ133p53γ proteins in the cancer sample protein extract. Methods for extracting proteins from a cell or tissue sample are well known to those skilled in the art. Such preliminary substep of extracting proteins is nevertheless not necessary when some particular technologies able to measure the amount of a particular protein directly in a cell or tissue sample are used.

When the expression level of Δ133p53β isoform, Δ133p53γ isoform, or both Δ133p53β and Δ133p53γ isoforms in said untreated and treated cancer sample is measured at the protein level, any appropriate technology known to those skilled in the art for measuring protein expression levels may be used. Suitable technologies include enzyme-linked immunosorbent assays (ELISAs), Western blots, immunoprecipitations, immunohistochemistry, and immunofluorescence.

Most of suitable technologies use an antibody able to bind to Δ133p53β isoform, Δ133p53γ isoform, or both Δ133p53β and Δ133p53γ isoforms. Such antibody may specifically bind to Δ133p53β isoform (anti-Δ133p53β antibody) and/or to Δ133p53γ isoform (anti-Δ133p53γ antibody), or may recognize several p53 isoforms, including the Δ133p53β isoform, the Δ133p53γ isoform, or both the Δ133p53β and Δ133p53γ isoforms.

When performed at the protein level, step a) is thus preferably performed by an immunoassay using an antibody able to bind to Δ133p53β isoform, Δ133p53γ isoform, or both Δ133p53β and Δ133p53γ isoforms, such as an antibody binding to Δ133p53β and/or Δ133p53γ isoform and to other p53 isoforms, an anti-Δ133p53β antibody or an anti-Δ133p53γ antibody. The antibody can be a polyclonal antibody or a monoclonal antibody, although monoclonal antibodies are preferred. Preferably, said antibody is labelled.

When an antibody binding to Δ133p53β isoform, Δ133p53γ isoform, or both Δ133p53β and Δ133p53γ isoforms and to other p53 isoforms (including an antibody binding all p53 isoforms) is used, the relative amount of Δ133p53β or Δ133p53γ isoform may be determined using western blot analysis, based on the distinct molecular weights of the various p53 isoforms (see FIG. 1A). Such antibody binding to Δ133p53β and/or Δ133p53γ isoform and to other p53 isoforms are commercially available, such as the p53 (DO-1): sc-126 antibody recognizing amino acids 11-25 of human p53 available from Santa Cruz Biotechnology.

Using an anti-Δ133p53β or anti-Δ133p53γ specific antibody, detection may be accomplished using any of a variety of immunoassays.

For example, by radioactively labelling an antibody, it is possible to detect the antibody through the use of radioimmune assays. A description of a radioimmune assay (RIA) may be found in Laboratory Techniques and Biochemistry in Molecular Biology, by Work T. S. et al., North Holland Publishing Company, NY (1978), with particular reference to the chapter entitled "An Introduction to Radioimmune Assay and Related Techniques" by Chard T. The radioactive isotope can be detected by such means as the use of a gamma counter or a scintillation counter or by audioradiography.

Isotopes which are particularly useful for the purpose of the present invention are: 3H, 1311, 35S, 14C, and preferably 1251.

It is also possible to label an antibody with a fluorescent compound. When the fluorescently labelled antibody is exposed to light of the proper wave length, its presence can then be detected due to fluorescence. Among the most commonly used fluorescent labelling compounds are fluorescein isothiocyanate, rhodamine, phycoerytherin, phycocyanin, allophycocyanin, ophthaldehyde and fluorescamine.

An antibody can also be detectably labelled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody can also be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, luciferin, isoluminol, theromatic acridinium ester, imidazole, acridinium salt and oxalate ester.

Likewise, a bioluminescent compound may be used to label an antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labelling are luciferin, luciferase and aequorin.

In the detection assays of the invention, the amount of binding of the antibody to the biological sample can be determined by the intensity of the signal emitted by the labelled antibody and/or by the number cells in the biological sample bound to the labelled antibody.

The detection or the expression level of Δ133p53β or Δ133p53γ isoform in a cancer sample may notably be determined by a radioimmunoassay (RIA), an immunoradiometric assay (IRMA), and/or an enzyme immunoassay (such as Enzyme-Linked Immunosorbent Assay (ELISA)).

"Radioimmunoassay" is a technique for detecting and measuring the concentration of an antigen using a radioactively labelled form of the antigen (i.e. Δ133p53β or Δ133p53γ polypeptide). Examples of radioactive labels for antigens include $^3$H, $^{14}$C, and $^{125}$I. The concentration of the antigen (Δ133p53β or Δ133p53γ polypeptide) in a biological sample is measured by having the non-labelled antigen in the sample compete with a radioactively labelled antigen for binding to an antibody to the antigen (anti-Δ133p53β or anti-Δ133p53γ antibody). To ensure competitive binding between the labelled antigen and the unlabeled antigen, the labelled antigen is present in a sufficient concentration to saturate the binding sites of the antibody. The higher the concentration of antigen in the sample, the lower the concentration of labelled antigen that will bind to the antibody will be.

In a radioimmunoassay, to determine the concentration of labelled antigen bound to an antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed S. aureus. Yet another method for separating the antigen-antibody complex from the free antigen is by performing a "solid-phase radioimmunoassay" where the antibody is linked (i.e. covalently) to Sepharose beads, polystyrene wells, polyvinylchloride wells, or microtiter wells. By comparing the concentration of labelled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labelled. An IRMA requires the production of a multivalent antigen conjugate by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere.

Unlabelled "sample" antigen and radioactively labelled antibody to antigen are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)". The "Enzyme-Linked Immunosorbent Assay (ELISA)" is a technique for detecting and measuring the concentration of an antigen using a labelled (i.e. enzyme linked) form of the antibody.

In a "sandwich ELISA", an antibody (anti-Δ133p53β or anti-Δ133p53γ antibody) is linked to a solid phase (i.e. a microtiter plate) and exposed to a biological sample containing antigen (Δ133p53β or Δ133p53γ polypeptide). The solid phase is then washed to remove unbound antigen. An enzyme-linked antibody to the antigen is then bound to the bound-antigen (if present) forming an antibody-antigen-antibody sandwich. Examples of enzymes that can be linked to the antibody are alkaline phosphatase, horseradish peroxidase, luciferase, urease, and 3-galactosidase. The enzyme linked antibody reacts with a substrate to generate a colored reaction product that can be assayed for.

In a "competitive ELISA", an antibody (anti-Δ133p53β or anti-Δ133p53γ antibody) is incubated with a sample containing antigen (Δ133p53β or Δ133p53γ polypeptide). The antigen-antibody mixture is then contacted with an antigen-coated solid phase (i.e. a microtiter plate). The more antigen present in the sample, the less free antibody that will be available to bind to the solid phase. An enzyme-linked secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e. g., luciferase, alkaline phosphatase, horseradish peroxidase, or P-galactosidase), or chemical methods (e.g., DAB/Substrate chromagen) or gold, fluorescent or labelled antibodies by any of the many different methods known to those skilled in this art.

Measure at the Nucleic Level

In another embodiment of the method of prediction of the risk that a chemotherapeutic anti-cancer treatment induces cancer stem cells according to the invention, the expression levels of Δ133p53β or Δ133p53γ isoform in said untreated and treated cancer sample are measured at the nucleic level by measuring the amount of Δ133p53β isoform, Δ133p53γ isoform, or both Δ133p53β and Δ133p53γ isoforms mRNA or corresponding cDNA. In this case, preliminary substeps of transformation of the untreated and treated cancer sample may include a substep of extraction of mRNAs present in the cancer sample, optionally followed by converting said mRNAs into cDNA. Methods for extracting mRNAs from a cell or tissue sample and for converting mRNAs into cDNAs are well known to those skilled in the art. Such preliminary substep of extracting mRNAs and optionally of converting mRNAS into cDNAs are nevertheless not necessary when some particular technologies able to measure the amount of a particular mRNA directly in a cell or tissue sample are used (such as in situ hybridization).

When the expression level of Δ133p53β isoform, Δ133p53γ isoform, or both Δ133p53β and Δ133p53γ isoforms in said untreated and treated cancer sample is measured at the nucleic level by measuring the amount of Δ133p53β isoform, Δ133p53γ isoform, or both Δ133p53β and Δ133p53γ isoforms mRNA or corresponding cDNA, any appropriate technology known to those skilled in the art for measuring mRNA or cDNA expression levels may be used. Suitable technologies include nucleic microarrays, quantitative PCR, next generation sequencing and hybridization with a labelled probe (including Northern hybridization and in situ hybridization).

In particular, real time quantitative RT-PCR (qRT-PCR) may be useful. qRT-PCR is a well-known and easily available technology for those skilled in the art and does not need a precise description. Examples of qRT-PCR-based methods can be found, for example, in U.S. Pat. No. 7,101,663. Commercially available qRT-PCR based methods (e.g., Taqman® Array) may for instance be employed, the design of primers and/or probe being easily made based on the sequences of Δ133p53β or Δ133p53γ isoform disclosed in Table 1 above. In a preferred embodiment of the method of prediction of the invention, the expression level of Δ133p53β isoform, Δ133p53γ isoform, or both Δ133p53β and Δ133p53γ isoforms in said cancer sample is measured at the nucleic level by measuring the amount of Δ133p53β isoform, Δ133p53γ isoform, or both Δ133p53β and Δ133p53γ isoforms mRNA or corresponding cDNA by qRT-PCR.

Nucleic acid assays or arrays can also be used to assess in vitro the expression level of Δ133p53β isoform, Δ133p53γ isoform, or both Δ133p53β and Δ133p53γ isoforms in a cancer sample, by measuring in vitro the amount of Δ133p53β isoform, Δ133p53γ isoform, or both Δ133p53β and Δ133p53γ isoforms mRNA or cDNA in the cancer sample.

In some embodiments, a nucleic acid microarray can be prepared or purchased. An array typically contains a solid support and at least one nucleic acid (cDNA or oligonucleotide) contacting the support, where the oligonucleotide corresponds to at least a portion of a gene. Any suitable assay platform can be used to measure in vitro the amount of Δ133p53β or Δ133p53γ isoform in a cancer sample. For example, an assay may be in the form of a membrane, a chip, a disk, a test strip, a filter, a microsphere, a multiwell plate, and the like. An assay system may have a solid support on which a nucleic acid (cDNA or oligonucleotide) binding to the Δ133p53β isoform, the Δ133p53γ isoform, or both the 133p53β and Δ133p53γ isoforms mRNA or cDNA is attached. The solid support may comprise, for example, a plastic, silicon, a metal, a resin, or a glass.

The assay components can be prepared and packaged together as a kit for detecting a gene. To determine the expression profile of a target nucleic sample, said sample is labelled, contacted with the microarray in hybridization conditions, leading to the formation of complexes between target nucleic acids that are complementary to probe sequences attached to the microarray surface. The presence of labelled hybridized complexes is then detected. Many variants of the microarray hybridization technology are available to the person skilled in the art.

Other technologies using hybridization with a labelled probe may be used. The sequence of the labelled probe will be selected to specifically hybridize under stringent conditions to the Δ133p53β isoform, the Δ133p53γ isoform, or both the Δ133p53β and Δ133p53γ isoforms mRNA or cDNA. Examples of suitable probes sequences are disclosed in Table 4 below. The labelled probe includes a label group attached thereto, e. g., a radioisotope, a fluorescent compound, an enzyme, or an enzyme co-factor.

In another embodiment, the in vitro measure of Δ133p53β isoform, Δ133p53γ isoform, or both Δ133p53β and Δ133p53γ isoforms mRNA or cDNA expression level may be performed by sequencing mRNA or cDNA extracted from the cancer sample.

In some embodiments, the mRNA or cDNA sample may be amplified to increase the sensitivity of detection of the method. Such amplification may be performed using any suitable technology known to those skilled in the art, including PCR or RT-PCR reaction.

In this case, primers permitting amplification of the Δ133p53β isoform, the Δ133p53γ isoform, or both Δ133p53β and Δ133p53γ isoforms mRNA or cDNA are used. Said primers may notably have the sequences presented in Table 4 below.

TABLE 4

Examples of suitable forward/reward amplification primers and hybridization probes for amplifying or detecting Δ133p53β isoform, Δ133p53γ isoform, or both Δ133p53β and Δ133p53γ isoforms.

|  | Δ133p53 isoforms (α, β and γ) | β isoforms (p53 TAβ, Δ40p53β, Δ133p53β, and Δ160p53β) |
|---|---|---|
| Forward primer | 5'-ACTCTGTCTCCTT CCTCTTCCTACAG-3' (SEQ ID NO: 7) | 5'-AACCACTGGATGG AGAATATTTCAC-3' (SEQ ID NO: 10) |
| Reward primer | 5'-GTGTGGAATCAAC CCACAGCT-3' (SEQ ID NO: 8) | 5'-TCATAGAACCATT TTCATGCTCTCTT-3' (SEQ ID NO: 11) |
| Hybridization probe | 5'-TCCCCTGCCCTCA ACAAGATGTTTTGCC-3' (SEQ ID NO: 9) | 5'-CAGGACCAGACCA GCTTTCAAAAAGAAAA TTGTT-3' (SEQ ID NO: 12) |

Step b)—Treatment of the Cancer Sample with Said Chemotherapeutic Anti-Cancer Agent In step b), the cancer sample (or part thereof) is treated with said chemotherapeutic anti-cancer agent.

Step d) Comparison of the Expression Levels Measured in Steps a) and c)

In step d), the expression level of Δ133p53β isoform, Δ133p53γ isoform, or both Δ133p53β and Δ133p53γ isoforms in the subject's treated cancer sample measured in step c) is compared to the expression level of Δ133p53β isoform, Δ133p53γ isoform, or both Δ133p53β and Δ133p53γ isoforms in the subject's untreated cancer sample measured in step a).

More particularly, it is determined if the expression level of Δ133p53β isoform, Δ133p53γ isoform, or both Δ133p53β and Δ133p53γ isoforms in the subject's treated cancer sample measured in step c) is:

(i) Higher than the expression level of Δ133p53β isoform, Δ133p53γ isoform, or both Δ133p53β and Δ133p53γ isoforms in the subject's untreated cancer sample measured in step a), or
(ii) Lower than or equal to the expression level of Δ133p53β isoform, Δ133p53γ isoform, or both Δ133p53β and Δ133p53γ isoforms in the subject's untreated cancer sample measured in step a).

Step e)—Prediction of the Risk of Induction of Cancer Stem Cells)

In step e), it is concluded to:
(i) the presence of a significant risk that treatment with said chemotherapeutic anti-cancer agent induces cancer stem cells in said subject if the expression level of Δ133p53β isoform, Δ133p53γ isoform, or both Δ133p53β and Δ133p53γ isoforms measured in step c) is higher than the expression level of Δ133p53β isoform, Δ133p53γ isoform, or both Δ133p53β and Δ133p53γ isoforms measured in step a), or
(ii) the absence of a significant risk that treatment with said chemotherapeutic anti-cancer agent induces cancer stem cells in said subject if the expression level of Δ133p53β isoform, Δ133p53γ isoform, or both Δ133p53β and Δ133p53γ isoforms measured in step c) is lower than or equal to the expression level of Δ133p53β isoform, Δ133p53γ isoform, or both Δ133p53β and Δ133p53γ isoforms measured in step a).

PREFERRED EMBODIMENTS

Various preferred specific features corresponding to various generic elements of the method for predicting the risk that treatment with a chemotherapeutic anti-cancer agent induces cancer stem cells in a subject suffering from cancer according to the invention have been described above in the section specifically relating to this element.

In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the method for predicting the risk that treatment with a chemotherapeutic anti-cancer agent induces cancer stem cells in a subject suffering from cancer according to the invention may be combined with any generic other element or with preferred embodiments of said other element. Preferred embodiments correspond to those in which at least one element is limited to a preferred embodiment, as listed in Table 5 below:

TABLE 5

Preferred embodiment of various elements of the method for predicting the risk that treatment with a chemotherapeutic anti-cancer agent induces cancer stem cells in a subject suffering from cancer according to the invention.

| Element | Preferred embodiment(s) |
| --- | --- |
| Cancer cell | Breast cancer cell or colorectal cancer |
| Chemotherapeutic anti-cancer agent | topoisomerase II inhibitor, preferably etoposide |
| P53 isoform which expression is measured in steps a) and c) | Δ133p53β isoform or Δ133p53β and Δ133p53γ isoforms, preferably Δ133p53β isoform |
| Method for measuring expression level | Nucleic acid level, preferably by q-RT-PCR |

In a particularly preferred embodiment of the method for predicting the risk that treatment with a chemotherapeutic anti-cancer agent induces cancer stem cells in a subject suffering from cancer according to the invention, cancer cells provided in step a) are breast cancer cells, the P53 isoform which expression is measured in steps a) and c) is Δ133p53β isoform or Δ133p53β and Δ133p53γ isoforms, and the expression level is measured at the nucleic level by measuring the amount of mRNA or corresponding cDNA.

Treatment of Cancer in a Subject Suffering from a Cancer

Based on the same finding of the inventors that anticancer treatment of cancer cells by etoposide (a topoisomerase II inhibitor) may not be only inefficient (resistance to treatment) but may further promote cancer stemness by increasing Δ133p53β expression level, the present invention also relates to a chemotherapeutic anti-cancer agent, for use in the treatment of cancer in a subject suffering from a cancer, wherein said chemotherapeutic anti-cancer agent is administered to said subject in combination with an agent reducing Δ133p53β or Δ133p53γ isoform expression.

Similarly, the present invention also relates to a method for treating cancer in a subject suffering from a cancer, comprising:
a) Administering to said subject a therapeutically efficient amount of an agent reducing Δ133p53β isoform, Δ133p53γ isoform, or both Δ133p53β and Δ133p53γ isoforms expression; and
b) Administering to said subject a therapeutically efficient amount of a chemotherapeutic anti-cancer treatment.

Chemotherapeutic Anti-Cancer Treatment

In the therapeutic uses according to the invention, the chemotherapeutic anti-cancer agent administered to a cancer subject may be any one of those listed by the American Cancer Society. Preferably the chemotherapeutic anti-cancer agent is selected from:
 a topoisomerase II inhibitor, including etoposide, etoposide, tenoposide, doxorubicine, daunorubicin, mitoxantrone, and amsacrine;
 an anti-tubuline agent, including taxanes such as paclitaxel and docetaxel, and vinca alkaloids such as vinblastine, vincristine, vindesine, and vinorelbine;

antimetabolites, including pyrimidine analogue 5-Fluorouracil (5-FU).

In a preferred embodiment, the chemotherapeutic anti-cancer treatment administered to a cancer subject is a topoisomerase II inhibitor, in particular selected from etoposide, etoposide, tenoposide, doxorubicine, daunorubicin, mitoxantrone, and amsacrine. More preferably, the chemotherapeutic anti-cancer treatment administered to a cancer subject is etoposide.

Agent Reducing Δ133p53β Isoform, Δ133p53γ Isoform, or Both Δ133p53β and Δ133p53γ Isoforms Expression Any agent reducing Δ133p53β isoform, Δ133p53γ isoform, or both Δ133p53β and Δ133p53γ isoforms expression may be used.

Agent reducing Δ133p53β isoform, Δ133p53γ isoform, or both Δ133p53β and Δ133p53γ isoforms expression include antisense RNA or interfering RNA (IRNA), including more particularly small interfering RNAs (siRNAs) and short hairpin RNAS (shRNAs).

Sequences targeted by specific shRNAs reducing Δ133p53β and/or Δ133p53γ isoform expression are provided in Table 6 below:

TABLE 6

Sequences targeted by specific shRNAs reducing Δ133p53β and/or Δ133p53γ isoform expression.

| Name | Region of p53 targeted/ targeted isoforms | 5' to 3' sequence |
|---|---|---|
| Sh1 | DBD domain/all p53 isoforms | 5'-GACTCCAGTGGTAATCTAC-3' (SEQ ID NO: 13) |
| Sh3 | 5' UTR of Δ133 isoforms/all Δ133 isoforms (α, β and γ) | 5'-GGAGGTGCTTACACATGTT-3' (SEQ ID NO: 14) |
| Sh4 | 5' UTR of Δ133 isoforms/all Δ133 isoforms (α, β and γ) | 5'-CTTGTGCCCTGACTTTCAA-3' (SEQ ID NO: 15) |
| Sh5 | 3'end of β isoforms (p53 TAβ, Δ40p53β, Δ133p53β, and Δ160p53β) | 5'-GGACCAGACCAGCTTTCA-3' (SEQ ID NO: 16) |

Δ133p53β and Δ133p53γ isoforms are expressed when alternative splicing of p53 gene occurs. As a result, agents reducing Δ133p53β and/or Δ133p53γ isoform expression also include agents targeting alternative splicing, including compounds of formulas (I), (Ia), (Ib), (Ic), (Id), (Ie), (If), (Ig), (Ih), (Ii), (Ij), (Ik), (Il), (Im), (Io), (Ip), (Iq), (Ir), (Iee), and more particularly compounds (1) to (168) and pharmaceutically acceptable salts thereof disclosed in WO2010/143168. Compounds (6), (18), (30), (35), (36), (37), (45), (48), (51), (52), (53), (55), (56), (58), (61), (63), (64), (109), (110), (112), (143), (144) and (148) are preferred.

The skilled artisan will be able to screen other agents reducing Δ133p53β and/or Δ133p53γ isoform expression by using the screening method of the present invention.

Administration Regimen

The chemotherapeutic anti-cancer agent and the agent reducing Δ133p53β isoform, Δ133p53γ isoform, or both Δ133p53β and Δ133p53γ isoforms expression are administered in therapeutically efficient amounts.

The chemotherapeutic anti-cancer agent and the agent reducing Δ133p53β isoform, Δ133p53γ isoform, or both Δ133p53β and Δ133p53γ isoforms expression may be administered simultaneously (in a same composition or in two distinct compositions) or sequentially, or both simultaneously (in a same composition or in two distinct compositions) and sequentially (i.e. both compounds are administered simultaneously during a period, but one or the other compound is administered alone before and/or after the simultaneous administration period).

In an embodiment, both compounds are administered simultaneously (in a same composition or in two distinct compositions).

In another embodiment, both compounds are administered sequentially. In this case, the chemotherapeutic anti-cancer agent may be administered before the agent reducing Δ133p53β isoform, Δ133p53γ isoform, or both Δ133p53β and Δ133p53γ isoforms expression, or the agent reducing Δ133p53β isoform, Δ133p53γ isoform, or both Δ133p53β and Δ133p53γ isoforms expression may be administered before the chemotherapeutic anti-cancer agent.

In another embodiment, both compounds are administered simultaneously during a period, but one or the other compound is administered alone before and/or after the simultaneous administration period. This includes:

Prior administration of chemotherapeutic anti-cancer agent alone followed by simultaneous administration of chemotherapeutic anti-cancer agent and agent reducing Δ133p53β isoform, Δ133p53γ isoform, or both Δ133p53β and Δ133p53γ isoforms expression, Prior administration of agent reducing Δ133p53β isoform, Δ133p53γ isoform, or both Δ133p53β and Δ133p53γ isoforms expression alone followed by simultaneous administration of chemotherapeutic anti-cancer agent and agent reducing Δ133p53β isoform, Δ133p53γ isoform, or both Δ133p53β and Δ133p53γ isoforms expression, Simultaneous administration of chemotherapeutic anti-cancer agent and agent reducing Δ133p53β isoform, Δ133p53γ isoform, or both Δ133p53β and Δ133p53γ isoforms expression followed by administration of chemotherapeutic anti-cancer agent alone, Simultaneous administration of chemotherapeutic anti-cancer agent and agent reducing Δ133p53β isoform, Δ133p53γ isoform, or both Δ133p53β and Δ133p53γ isoforms expression followed by administration of agent reducing Δ133p53β isoform, Δ133p53γ isoform, or both Δ133p53β and Δ133p53γ isoforms expression alone, Prior administration of chemotherapeutic anti-cancer agent alone followed by simultaneous administration of chemotherapeutic anti-cancer agent and agent reducing Δ133p53β isoform, Δ133p53γ isoform, or both Δ133p53β and Δ133p53γ isoforms expression, followed by administration of chemotherapeutic anti-cancer agent alone, Prior administration of chemotherapeutic anti-cancer agent alone followed by simultaneous administration of chemotherapeutic anti-cancer agent and agent reducing Δ133p53β isoform, Δ133p53γ isoform, or both Δ133p53β and Δ133p53γ isoforms expression, followed by administration of agent reducing Δ133p538 isoform, Δ133p53γ isoform, or both Δ133p53β and Δ133p53γ isoforms expression alone, Prior administration of agent reducing Δ133p53β isoform, Δ133p53γ isoform, or both Δ133p53β and Δ133p53γ isoforms expression alone followed by simultaneous administration of chemotherapeutic anti-cancer agent and agent reducing Δ133p53β isoform, Δ133p53γ isoform, or both Δ133p53β and Δ133p53γ isoforms expression, followed by administration of chemotherapeutic anti-cancer agent alone, and Prior administration of agent reducing Δ133p53β isoform, Δ133p53γ isoform, or both Δ133p53β and Δ133p53γ isoforms expression alone followed by simultaneous administration of chemotherapeutic anti-cancer agent and agent reducing Δ133p53β isoform, Δ133p53γ isoform, or both Δ133p53β and Δ133p53γ isoforms expression, followed by administration of agent reducing Δ133p53β isoform, Δ133p53γ isoform, or both Δ133p53β and Δ133p53γ isoforms expression alone.

Since chemotherapeutic anti-cancer agent may promote induction of cancer stem cells, preferred administration regimens are those in which the agent reducing Δ133p53β isoform, Δ133p53γ isoform, or both Δ133p53β and Δ133p53γ isoforms expression is administered simultaneously (at least during a period, in a same composition or in two distinct compositions) and/or after administration of the chemotherapeutic anti-cancer agent. Such preferred administration regimens include:

Simultaneous administration of both compounds,

Chemotherapeutic anti-cancer agent administration alone followed by administration of agent reducing Δ133p53β isoform, Δ133p53γ isoform, or both Δ133p53β and Δ133p53γ isoforms expression alone, Simultaneous administration of chemotherapeutic anti-cancer agent and agent reducing Δ133p53β isoform, Δ133p53γ isoform, or both Δ133p53β and Δ133p53γ isoforms expression followed by administration of agent reducing Δ133p538 isoform, Δ133p53γ isoform, or both Δ133p53β and Δ133p53γ isoforms expression alone, Prior administration of chemotherapeutic anti-cancer agent alone followed by simultaneous administration of chemotherapeutic anti-cancer agent and agent reducing Δ133p53β isoform, Δ133p53γ isoform, or both Δ133p53β and Δ133p53γ isoforms expression, followed by administration of agent reducing Δ133p53β isoform, Δ133p53γ isoform, or both Δ133p53β and Δ133p53γ isoforms expression alone, and Prior administration of agent reducing Δ133p53β isoform, Δ133p53γ isoform, or both Δ133p53β and Δ133p53γ isoforms expression alone followed by simultaneous administration of chemotherapeutic anti-cancer agent and agent reducing Δ133p53β isoform, Δ133p53γ isoform, or both Δ133p53β and Δ133p53γ isoforms expression, followed by administration of agent reducing Δ133p53β isoform, Δ133p53γ isoform, or both Δ133p53β and Δ133p53γ isoforms expression alone.

Preferred Embodiments

Various preferred specific features corresponding to various generic elements of the therapeutic uses of a combination of a chemotherapeutic anti-cancer agent and an agent reducing Δ133p53β isoform, Δ133p53γ isoform, or both Δ133p53β and Δ133p53γ isoforms expression according to the invention have been described above in the section specifically relating to this element. In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the therapeutic uses of a combination of a chemotherapeutic anti-cancer agent and an agent reducing Δ133p53β isoform, Δ133p53γ isoform, or both Δ133p53β and Δ133p53γ isoforms expression according to the invention may be combined with any generic other element or with preferred embodiments of said other element.

Preferred embodiments correspond to those in which at least one element is limited to a preferred embodiment, as listed in Table 7 below:

TABLE 7

Preferred embodiment of various elements of the therapeutic uses of a combination of a chemotherapeutic anti-cancer agent and an agent reducing Δ133p53β isoform, Δ133p53γ isoform, or both Δ133p53β and Δ133p53γ isoforms expression according to the invention.

| Element | Preferred embodiment(s) |
|---|---|
| Cancer | Breast cancer or colorectal cancer |
| Chemotherapeutic anti-cancer agent | topoisomerase II inhibitor, preferably etoposide |
| agent reducing Δ133p53β isoform, Δ133p53γ isoform, or both Δ133p53β and Δ133p53γ isoforms | siRNA, shRNAs, or agents targeting alternative splicing |
| Administration regimen | the agent reducing Δ133p53B isoform, Δ133p53γ isoform, or both Δ133p53B and Δ133p53γ isoforms expression is administered simultaneously (at least during a period, in a same composition or in two distinct compositions) and/or after administration of the chemotherapeutic anti-cancer agent |

In a particularly preferred embodiment of the therapeutic uses of a combination of a chemotherapeutic anti-cancer agent and an agent reducing Δ133p53β isoform, Δ133p53γ isoform, or both Δ133p53β and Δ133p53γ isoforms expression according to the invention, cancer is breast cancer, the chemotherapeutic anti-cancer agent is etoposide, the agent reducing Δ133p53β isoform, Δ133p53γ isoform, or both Δ133p53β and Δ133p53γ isoforms is a siRNA, a shRNA or an agent targeting alternative splicing selected from compounds of formulas (I), (Ia), (Ib), (Ic), (Id), (Ie), (If), (Ig), (Ih), (Ii), (Ij), (Ik), (Il), (Im, (Io), (Ip), (Iq), (Ir), (Iee), and more particularly compounds (1) to (168) and pharmaceutically acceptable salts thereof disclosed in WO2010/143168 (in particular compounds (6), (18), (30), (35), (36), (37), (45), (48), (51), (52), (53), (55), (56), (58), (61), (63), (64), (109), (110), (112), (143), (144) and (148)).

Prediction of Risk of Metastasis

The results obtained by the inventors show that Δ133p53β or Δ133p53γ isoform expression promotes cancer stem cell potential, in particular by upregulating expression of transcription factors Sox 2, Oct 3/4 and Nanog, suggesting that expression of Δ133p53β or Δ133p53γ isoform may be an early event of reprogramming of cancer cells towards cancer stem cells, and that detection of other cancer stem cells features in addition to detection of Δ133p53β or Δ133p53γ isoform expression may improve the reliability of prediction of a risk of cancer metastasis in a subject suffering from cancer. The present invention thus also relates to a method for predicting a risk of cancer metastasis in a subject suffering from cancer from a cancer sample of said subject, comprising:
  a) detecting sphere-forming cancer cells expressing Δ133p53β isoform, Δ133p53γ isoform, or both Δ133p53β and Δ133p53γ isoforms in said cancer sample; and
  b) concluding to the presence of a significant risk of cancer metastasis in said subject if sphere-forming cancer cells expressing Δ133p53β isoform, Δ133p53γ isoform, or both Δ133p53β and Δ133p53γ isoforms are detected and to the absence of a significant risk of cancer metastasis in said subject if sphere-forming cancer cells expressing Δ133p53β isoform, Δ133p53γ isoform, or both Δ133p53β and Δ133p53γ isoforms are not detected.

Cancer and Cancer Sample

In the method of prediction of risk of metastasis according to the invention, the cancer from which the subject is suffering is preferably selected from the group of solid cancers, and in particular from the group consisting of breast cancer, ovarian cancer, digestive cancers (also referred as gastrointestinal cancer, including colorectal cancer oesophageal cancer, gastric cancer, pancreatic cancer, hepatocellular carcinoma, cholangiocellular cancer and teratocarcinoma), pancreatic cancer and throat cancer, particularly of human subject, more preferably from breast cancer, colorectal cancer gastrointestinal cancer, lung cancer and prostate cancer, and even more preferably the cancer from which the subject is suffering is breast cancer or colorectal cancer.

Moreover, the cancer from which the subject is suffering may be selected from the group of hematopoietic cancers, and in in particular from the group consisting of leukaemias and lymphomas. Preferably, the hematopoietic cancer is a human hematopoietic cancer.

It is known in the art that many types of cancer cells, when transduced by at least one and preferably several of Yamanaka factors (Oct 3/4, Nanog, Sox 2 and c-Myc), may give rise to CSCs. Examples of cancer cells in which this has been shown include:
  colon (or colorectal) cancer cells (see for instance Oshima et al (2014), which describes that colon cancer cells transduced with factors Oct 3/4, Sox 2 and KLF4 showed significantly enhanced CSCs proprieties in terms of marker gene expression and sphere formation),
  gastrointestinal cancer cells (including cells of colorectal cancer, oesophageal cancer, gastric cancer, pancreatic cancer, hepatocellular carcinoma, cholangiocellular cancer and teratocarcinoma). Miyoshi et al (2010) disclose that cells obtained from the above cited gastrointestinal cancers induced with Nanog transcriptional factor manifest a pluripotency like CSCs,
  lung cancer cells (see Chiou et al., 2010, which describes that ectopic expression of Oct4 and Nanog transcriptional factors in lung adenocarcinoma cells induce the sphere formation), and
  prostate cancer cells (see Jeter et al, 2011, which describes that tetracycline-inducible Nanog-overexpression in prostate cancer cell lines promotes tumour regeneration by enhancing the expression of several CSCs associated molecules.

Since transduction with Δ133p53β isoform or Δ133p53γ isoform induces the expression of Sox 2, Nanog and Oct 3/4, its transduction in any cancer cell known to give rise to CSCs when transduced by at least one and preferably several of Yamanaka factors (Oct 3/4, Nanog, Sox 2 and c-Myc) is expected to generate CSCs. This has been demonstrated by the inventors for two distinct types of cancer cells: breast and colon cancer cells.

The cancer sample from which the expression level of Δ133p53β isoform, Δ133p53γ isoform, or both Δ133p53β and Δ133p53γ isoforms is measured in step a) may be a cancer biopsy or a complete or partial cancer surgical resection. Alternatively, the cancer sample from which the expression level of Δ133p53β isoform, Δ133p53γ isoform, or both Δ133p53β and Δ133p53γ isoforms is measured in step a) may be a blood sample. Indeed, cancer cells (including cancer stem cells) are well known to circulate in blood (Mavroudis-2010; Alix-Panabières et al,. 2013)

Isoform

In a preferred embodiment of the method of risk of metastasis according to the invention, it is the expression level of Δ133p53β isoform or both Δ133p53β and Δ133p53γ isoforms that is measured in step a). Indeed, expression of Δ133p53β isoform is particularly associated to induction of cancer stem cells.

Detection of Δ133p53β Isoform, Δ133p53γ Isoform, or Both Δ133p53β and Δ133p53γ Isoforms Expression In step a), expression of Δ133p53β isoform, Δ133p53γ isoform, or both Δ133p53β and Δ133p53γ isoforms is detected.

For this purpose, any method disclosed in relation to the method of prediction of the risk that a chemotherapeutic anti-cancer treatment induces cancer stem cells according to the invention may be used.

Detection of Cancer Cells Sphere-Forming Capacity

The cancer stem cell phenotype is also characterized by the preferential ability of cancer stem cells to form spheres under serum-free (and preferably low adherence) culture conditions, whereas bulk tumor cells are less likely to be able to form spheres under the same conditions.

The sphere-forming capacity of cancer cells may be tested using an assay comprising:
  i) resuspending cancer cells into a serum-free medium, preferably in the presence of specific growth factors (including, but not limited to, Epidermal Growth Factor (EGF) and basic Fibroblast Growth Factor (bFGF)), and plating them into tissue culture dishes, to which mammalian cells preferably poorly adhere;
  ii) incubating the cancer cells during 5 to 20 days; and
  iii) counting spheres.

In step i), cancer cells are resuspended into a serum-free medium (e.g., MammoCult®, available from StemCell Technologies, Inc., Vancouver, Canada), preferably in the presence of specific growth factors such as EGF and bFGF, and plated into tissue culture dishes. Preferably, tissue culture dishes to which mammalian cells poorly adhere are selected (e.g. Ultra Low Cluster Plate, 24-well, Flat Bottom from Corning Inc). In this step, the seeding density is preferably kept between 250 and 2500 cells/cm², and is preferably optimized for each type of cancer cells.

For instance, for breast cancer cells in MammoCult™ Medium enriched with MammoCult™Proliferation Supplements, hydrocortisone and heparin (Stem Cell Technologies), a seeding density of 500 cells/well of Ultra Low Cluster Plate, 24-well, Flat Bottom (Corning Inc) is appropriate.

In step ii), cancer cells are incubated, preferably at about 37° C. under 5% CO₂ atmosphere, during 5 to 20 days, preferably during 7 to 15 days.

Finally, in step c), spheres that have formed during incubation are counted. Such counting is preferably made using a microscope, preferably a phase-contrast microscope, and spheres that are at least 50 µm large are preferably counted.

It is considered that a cancer sample contains sphere-forming cancer cells when spheres can be counted at least at the maximal seeding density of 2500 cells/cm².

Preferred Embodiments

Various preferred specific features corresponding to various generic elements of the method for predicting risk of metastasis according to the invention have been described above in the section specifically relating to this element. In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the method for predicting risk of metastasis according to the invention may be combined with any generic other element or with preferred embodiments of said other element.

Preferred embodiments correspond to those in which at least one element is limited to a preferred embodiment, as listed in Table 8 below:

detected in step a) is Δ133p53β isoform or Δ133p53β and Δ133p53γ isoforms, its/their the expression level(s) is/are measured at the nucleic level by measuring the amount of mRNA or corresponding cDNA (preferably by q-RT-PCR), and sphere-forming ability is detected by the preferred assay described in Table 8 above.

Prediction of Risk of Cancer Relapse in a Treated Cancer Patient

As mentioned above, the results obtained by the inventors show that Δ133p53β or Δ133p53γ isoform expression promotes cancer stem cell potential, in particular by upregulating expression of transcription factors Sox 2, Oct 3/4 and Nanog, suggesting that expression of Δ133p53β or Δ133p53γ isoform may be an early event of reprogramming of cancer cells towards cancer stem cells. It is thus possible to predict if a treated cancer subject, in which most cancer cells have been successfully eliminated, is risking cancer relapse if one or both of Δ133p53β or Δ133p53γ isoforms is/are expressed in a cell sample obtained from said subject.

The present invention thus also relates to a method for predicting a risk of cancer relapse in a treated cancer subject from a cell sample of said subject, comprising:

a) detecting the expression of Δ133p53β isoform, of Δ133p53γ isoform, or of both Δ133p53β and Δ133p53γ isoforms in said cell sample; and b) concluding to the presence of a significant risk of cancer relapse in said subject if the expression of Δ133p53β isoform, of Δ133p53γ isoform, or of both Δ133p53β and Δ133p53γ isoforms is detected and to the absence of a significant risk of cancer relapse in said subject if neither the expression of Δ133p53β isoform nor the expression of Δ133p53γ isoform are detected.

Optionally, the method for predicting a risk of cancer relapse in a treated cancer subject according to the invention may also comprise an additional step c) of comparing the expression of Δ133p53β isoform, Δ133p53γ isoform, or of both Δ133p53β and Δ133p53γ isoforms in the tested cell sample to expression of the same isoforms in a previously tested cancer sample from said treated cancer subject.

TABLE 8

Preferred embodiment of various elements of the method for predicting risk of metastasis according to the invention.

| Element | Preferred embodiment(s) |
|---|---|
| Cancer | Breast cancer or colorectal cancer |
| P53 isoform which expression is detected in step a) | Δ133p53β isoform or Δ133p53β and Δ133p53γ isoforms, preferably Δ133p53β isoform |
| Method for detecting P53 isoform expression | Nucleic acid level, preferably by q-RT-PCR |
| Method for detecting sphere-forming ability | An assay comprising:<br>i) resuspending cancer cells into a serum-free medium, preferably in the presence of specific growth factors such as EGF and bFGF, and plating them into tissue culture dishes, to which mammalian cells poorly adhere, at a seeding density between 250 and 2500 cells/cm²;<br>ii) incubating the cancer cells during 7 to 15 days; and<br>iii) counting spheres that are at least 50 µm large. |

In a particularly preferred embodiment of the method for predicting risk of metastasis according to the invention, cancer is breast cancer, the P53 isoform which expression is This method may be performed in one or several ways after the treatment of cancer as a preventive method in order to confirm diagnosis of cancer relapse.

Cancer and Non-Cancerous Cell Sample

In the method of prediction of risk of cancer relapse according to the invention, the cancer for which the subject has been successfully treated (most of cancer cells have been eliminated) is preferably selected from the group of solid cancers, and in particular from the group consisting of breast cancer, ovarian cancer, digestive cancers (also referred as gastrointestinal cancer, including colorectal cancer oesophageal cancer, gastric cancer, pancreatic cancer, hepatocellular carcinoma, cholangiocellular cancer and teratocarcinoma), pancreatic cancer and throat cancer, particularly of human subject, more preferably breast cancer colorectal cancer, gastrointestinal cancer, lung cancer and prostate cancer and even more preferably the cancer is breast cancer or colorectal cancer.

Moreover, the cancer may be selected from the group of hematopoietic cancers, and in particular from the group consisting of leukaemias and lymphomas. Preferably, the hematopoietic cancer is a human hematopoietic cancer.

It is known in the art that many types of cancer cells, when transduced by at least one and preferably several of Yamanaka factors (Oct 3/4, Nanog, Sox 2 and c-Myc), may give rise to CSCs. Examples of cancer cells in which this has been shown include:

- colon (or colorectal) cancer cells (see for instance Oshima et al (2014), which describes that colon cancer cells transduced with factors Oct 3/4, Sox 2 and KLF4 showed significantly enhanced CSCs proprieties in terms of marker gene expression and sphere formation),
- gastrointestinal cancer cells (including cells of colorectal cancer, oesophageal cancer, gastric cancer, pancreatic cancer, hepatocellular carcinoma, cells obtained from the above cited gastrointestinal cancers induced with Nanog transcriptional factor manifest a pluripotency like CSCs,
- lung cancer cells (see Chiou et al., 2010, which describes that ectopic expression of Oct4 and Nanog transcriptional factors in lung adenocarcinoma cells induce the sphere formation), and
- prostate cancer cells (see Jeter et al, 2011, which describes that tetracycline-inducible Nanog-overexpression in prostate cancer cell lines promotes tumour regeneration by enhancing the expression of several CSCs associated molecules.

Since transduction with $\Delta 133p53\beta$ isoform or $\Delta 133p53\gamma$ isoform induces the expression of Sox 2, Nanog and Oct 3/4, its transduction in any cancer cell known to give rise to CSCs when transduced by at least one and preferably several of Yamanaka factors (Oct 3/4, Nanog, Sox 2 and c-Myc) is expected to generate CSCs. This has been demonstrated by the inventors for two distinct types of cancer cells: breast and colon cancer cells.

The cell sample from which the expression level of $\Delta 133p53\beta$ isoform, $\Delta 133p53\gamma$ isoform, or both $\Delta 133p53\beta$ and $\Delta 133p53\gamma$ isoforms is measured in step a) may be a biopsy of a tissue previously affected by a cancer of those described above or of subjacent tissue. Alternatively, the cancer sample from which the expression level of $\Delta 133p53\beta$ isoform, $\Delta 133p53\gamma$ isoform, or both $\Delta 133p53\beta$ and $\Delta 133p53\gamma$ isoforms is measured in step a) may be a blood sample. Indeed, cancer cells (including cancer stem cells) are well known to circulate in blood (Mavroudis-2010; Alix-Panabières et al,. 2013)

Isoform

In a preferred embodiment of the method of risk of relapsing cancer according to the invention, it is the expression level of $\Delta 133p53\beta$ isoform or both $\Delta 133p53\beta$ and $\Delta 133p53\gamma$ isoforms that is measured in step a). Indeed, expression of $\Delta 133p53\beta$ isoform is particularly associated to induction of cancer stem cells.

Detection of $\Delta 133p53\beta$ Isoform, $\Delta 133p53\gamma$ Isoform, or Both $\Delta 133p53\beta$ and $\Delta 133p53\gamma$ Isoforms Expression In step a), expression of $\Delta 133p53\beta$ isoform, $\Delta 133p53\gamma$ isoform, or both $\Delta 133p53\beta$ and $\Delta 133p53\gamma$ isoforms is detected.

For this purpose, any method disclosed in relation to the method of prediction of the risk that a chemotherapeutic anti-cancer treatment induces cancer stem cells according to the invention may be used.

Preferred Embodiments

Various preferred specific features corresponding to various generic elements of the method for predicting risk of metastasis according to the invention have been described above in the section specifically relating to this element. In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the method for predicting risk of relapsing of cancer of cured patient according to the invention may be combined with any generic other element or with preferred embodiments of said other element.

Preferred embodiments correspond to those in which at least one element is limited to a preferred embodiment, as listed in Table 8a below:

TABLE 8a

Preferred embodiment of various elements of the method for predicting risk of relapsing of cancer cured subject according to the invention.

| Element | Preferred embodiment(s) |
|---|---|
| Cancer | Breast cancer or colorectal cancer |
| P53 isoform which expression is detected in step a) | $\Delta 133p53\beta$ isoform or $\Delta 133p53\beta$ and $\Delta 133p53\gamma$ isoforms, preferably $\Delta 133p53\beta$ isoform |
| Method for detecting P53 isoform expression | Nucleic acid level, preferably by q-RT-PCR |
| Cell sample | Tissue sample |

In a particularly preferred embodiment of the method for predicting risk of relapsing of a cancer cured subject according to the invention, cancer is breast cancer, the P53 isoform which expression is detected in step a) is Δ133p53β isoform or Δ133p53β and Δ133p53γ isoforms, its/their the expression level(s) is/are measured at the nucleic level by measuring the amount of mRNA or corresponding cDNA (preferably by q-RT-PCR) in the non-cancerous cell tissue sample.

Screening of Anti-Cancer Stem Cells Agents

Based on the same finding that Δ133p53β or Δ133p53γ isoform expression promotes cancer stem cell potential, in particular by upregulating expression of transcription factors Sox 2, Oct 3/4 and Nanog, suggesting that expression of Δ133p53β or Δ133p53γ isoform may be an early event of reprogramming of cancer cells towards cancer stem cells, the present invention also relates to a method for screening potential anti-cancer stem cells compounds, comprising:

a) providing sphere-forming cancer stem cells expressing Δ133p53β isoform, Δ133p53γ isoform, or both Δ133p53β and Δ133p53γ isoforms;
b) contacting said cancer stem cells with a test compound;
c) measuring in vitro the expression level of said Δ133p53β isoform, Δ133p53γ isoform, or both Δ133p53β and Δ133p53γ isoforms in treated cells and/or the sphere-forming ability of treated cells;
d) selecting said test compound as a potential anti-cancer stem cells compound if the expression level of said Δ133p53β isoform, Δ133p53γ isoform, or both Δ133p53β and Δ133p53γ isoforms in treated cells is lower than before treatment with the test compound, and/or if the sphere-forming ability of treated cells is lower than before treatment with the test compound.

Sphere-Forming Cancer Stem Cells Expressing Δ133p53β Isoform, Δ133p53γ Isoform, or Both Δ133p53β and Δ133p53γ Isoforms Sphere-forming cancer stem cells expressing Δ133p53β isoform, Δ133p53γ isoform, or both Δ133p53β and Δ133p53γ isoforms provided in step a) may be either purified from a cancer sample or produced according to the method for producing cancer stem cells according to the invention.

When purified from a cancer sample, they may be obtained by submitting bulk cancer cells of the cancer sample to a sphere-forming assay, recovering spheres obtained in the assay and checking for Δ133p53β isoform, Δ133p53γ isoform, or both Δ133p53β and Δ133p53γ isoforms expression.

Test Compounds

The type of compounds tested in the method for screening of anti-cancer stem cells agents according to the invention are not particularly limited, and any type of chemical or biological compound may be tested.

Examples of test compounds include siRNAs, shRNAs, and agents targeting alternative splicing.

Measure of the Expression Level of Said Δ133p53β Isoform, Δ133p53γ Isoform, or Both Δ133p53β and Δ133p53γ Isoforms In step c), the expression level of Δ133p53β isoform, Δ133p53γ isoform, or both Δ133p53β and Δ133p53γ isoforms may be measured in vitro.

For this purpose, any method disclosed in relation to the method of prediction of the risk that a chemotherapeutic anti-cancer treatment induces cancer stem cells according to the invention may be used.

Measure of Sphere-Forming Ability of Treated Cells

In step c), the sphere-forming ability of treated cells may be measured in vitro. For this purpose, the assay disclosed above in relation of a method for predicting risk of metastasis according to the invention is preferably used.

Preferred Embodiments

Various preferred specific features corresponding to various generic elements of the method of screening of anti-cancer stem cells agents according to the invention have been described above in the section specifically relating to this element. In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the method of screening of anti-cancer stem cells agents according to the invention may be combined with any generic other element or with preferred embodiments of said other element.

Preferred embodiments correspond to those in which at least one element is limited to a preferred embodiment, as listed in Table 9 below:

TABLE 9

Preferred embodiment of various elements of the method of screening of anti-cancer stem cells agents according to the invention.

| Element | Preferred embodiment(s) |
| --- | --- |
| Cancer | Breast cancer or colorectal cancer |
| P53 isoform which expression is detected in step a) | Δ133p53β isoform or Δ133p53β and Δ133p53γ isoforms, preferably Δ133p53β isoform |
| Method for detecting P53 isoform expression | Nucleic acid level, preferably by q-RT-PCR |
| Method for detecting sphere-forming ability | An assay comprising: i) resuspending cancer cells into a serum-free medium, preferably in the presence of specific growth factors such as EGF and bFGF, and plating them into tissue culture dishes, to which mammalian cells poorly adhere, at a seeding density between 250 and |

TABLE 9-continued

Preferred embodiment of various elements of the method of screening of anti-cancer stem cells agents according to the invention.

| Element | Preferred embodiment(s) |
|---------|------------------------|
|  | 2500 cells/cm$^2$;<br>ii) incubating the cancer cells during 7 to 15 days; and<br>iii) counting spheres that are at least 50 µm large. |

In a particularly preferred embodiment of the method of screening of anti-cancer stem cells agents according to the invention, cancer is breast cancer, the P53 isoform which expression is detected in step a) is Δ133p53β isoform or Δ133p53β and Δ133p53γ isoforms, its/their the expression level(s) is/are measured at the nucleic level by measuring the amount of mRNA or corresponding cDNA (preferably by q-RT-PCR), and sphere-forming ability is detected by the preferred assay described in Table 9 above.

The following examples merely intend to illustrate the present invention.

EXAMPLES

Example 1: Materials and Methods

The following is a description of materials and methods used in following examples.

Plasmids

The human Δ133p53 isoforms (α, β and γ) were cloned with (Sh1-resistant variants) or without 3' fusion Flag tag in the pMSCVhyg (Clontech Laboratories) plasmid for retroviral production. Site-directed mutagenesis to obtain Sh1-resistant p53 isoforms was performed using the QuickChange II (Stratagene) mutagenesis kit. The silent mutation was introduced using the following oligonucleotide: 5'-CATCACACTGGAA<u>GATTCTAGCGGCAATC</u>TACTGGGACG-3' (SEQ ID NO: 17) (the underlined region is targeted by Sh1).

ShRNAs (Sh) were cloned in the RNAi-Ready pSIREN-Retro Q plasmid (Clontech Laboratories). The Sh sequences used in this study are (see also FIG. 1):

Sh1: 5'-GACTCCAGTGGTAATCTAC-3' (SEQ ID NO: 13)
Sh2: 5'-GTCCAGATGAAGCTCCCAGAA-3' (SEQ ID NO: 18)
Sh3: 5'-GGAGGTGCTTACACATGTT-3' (SEQ ID NO:14)
Sh4: 5'-CTTGTGCCCTGACTTTCAA-3' (SEQ ID NO: 15)
Sh5: 5'-GGACCAGACCAGCTTTCA-3' (SEQ ID NO: 16)
Sh6: 5'-GTGAGCGCTTCGAGATGTT-3' (SEQ ID NO:19)

All plasmids were verified by sequencing before use.

Cell Culture

The human breast cancer cell lines MCF-7, MDA-MB 231 D3H2LN and C3LND were grown in MEM supplemented with 10% FCS, sodium pyruvate and glutamine. Following viral infection, cells were used after 24-48 h or subjected to selection with 2 µg/ml puromycin (InvivoGen) or 300 µg/ml hygromycin B (Invitrogen) for two days. Etoposide treatment was performed with final doses of 12.5, 25 and 50 ng/ml for 16h or 50 ng/ml/day for 7 days.

For mammosphere formation, 1000 cells/ml (500 cells/well) were plated in Ultra Low Cluster Plate, 24-well, Flat Bottom (Corning Inc) with MammoCult™ Medium enriched with MammoCult™Proliferation Supplements, hydrocortisone and heparin (Stem Cell Technologies) and cultured for 15 days. For all mammosphere assays, at least three independent experiments for each condition were carried out and repeated 8-12 times. For self-renewal experiments, transfected cells were subjected to a first cycle of mammosphere formation. Upon 15 days of culture the created mammospheres were dissociated and cells were re-plated in identical conditions as for the first plating.

The same protocol has been used with human colon carcinoma cell line SW480.

MDA-MB231 C3LND Cell Line Establishment

The C3LND cell line was derived from distant metastases of the MDA-MB231-luc-D3H2LN cell line after two in vivo passages in nude mice.

Briefly, 1×10$^6$ cells per animal were resuspended in sterile PBS for intracardiac injections (first cycle of enrichment) or in 50% Matrigel (BD Biosciences, USA) for injection in the lower left mammary fat pad (second cycle of enrichment) of athymic nude mice (Hsd:Athymic Nude-Foxn1, Harlan). Tumor progression and time to metastasis were followed weekly by whole body bioluminescence imaging. Invaded organs were then resected and tumor cells isolated and propagated in vitro.

In Vivo Experiments

All in vivo experiments were performed in compliance with the French regulations and ethical guidelines for experimental animal studies in an accredited establishment (Agreement No. C34-172-27). 2.10$^6$ control or Sh3-treated C3LND cancer cells were grafted in 6 week-old female athymic mice (Harlan, Le Malourlet, France) by intracardiac injection (n=5-7/group). Bioluminescence detection was used to monitor tumor growth and distal metastasis formation in head and legs. Regions of interest (ROI) were delineated around the tumor sites and the total flux (ph/s) in the ROI was measured.

Antibodies, Immunoblotting and Immunofluorescence

The following antibodies were used for immunoblotting: anti-c-Myc (9E10 mouse hybridoma clone), -Nanog (sc-81961, Santa Cruz Biotechnology), -Oct 3/4 (sc-8630, Santa Cruz Biotechnology), -Sox 2 (sc-17320, Santa Cruz Biotechnology), -p53 (DO-1; sc-126 Santa Cruz Biotechnology), -p53 Sapu (Vojtesek et al. 1995), -α-tubulin (clone DM1A, Sigma-Aldrich), -β-actin (clone AC-74 Sigma-Aldrich), -p21 (sc-397 Santa Cruz Biotechnology) and -Flag (clone M2; Sigma-Aldrich). Secondary HRP-conjugated antibodies were from GE Healthcare. For luminescence quantification, cells were serially diluted and incubated with 0.5 mM D-luciferin (Sigma). Luminescence was quantified with a Polarstar Omega instrument (BMG LABTECH).

Flow Cytometry Analysis

Single cell suspensions were labeled on ice with CD24-FITC, CD44-PE and their respective isotype controls (BioLegend) at the dilutions indicated by the manufacturer in Phosphate Buffered Saline (PBS) with 10% FBS for 30 min. Cells were then washed once with PBS and re-suspended in PBS/10% FBS. All samples were analyzed on a CyAn analyzer (Becton Coulter, Inc) using Sytox Blue (Life Technologies) to monitor cell viability.

RNA Extraction and RT-qPCR

Total RNA was extracted (Qiagen) and reverse transcription (RT) was performed with 1-5 µg of total RNA using the SuperScript® III Reverse Transcriptase (Life Technologies) at 50° C. Levels of different mRNAs were quantified by real-time qPCR on a LightCycler480 apparatus (Roche). Briefly, 20 ng cDNA was amplified using 0.168 µM of each primer, 0.2 µM of probe (Table 4) and 1× LightCycler® 480 Probes Master Mix (Roche) for the p53 isoforms, or commercially available primers (Qiagen) and 1× LightCycler® 480 Sybr Green Master Mix (Roche) for the other genes. Data were normalized to the internal standard TBP. The different primers used and their corresponding sequences have been previously described (Bourdon et al., 2005). For each single-well amplification reaction, a threshold cycle (Ct) was calculated by using the LightCycler480 program (Roche) in the exponential phase of amplification. Relative changes in gene expression were determined using the 2ΔΔCt method and reported relative to a control. All quantification studies were performed with at least three independent experiments, repeated twice, for each condition. Data are presented as the arithmetic mean±SEM.

Statistical Analysis

All data are presented as the arithmetic mean±SEM. Statistical analyses were performed using the non-parametric Mann-Whitney t-test with the Prism software (GraphPad Software).

Example 2: Changes in the Expression of p53 Isoforms Affect Mammosphere Formation To study the role of the different p53 isoforms in CSC potential we designed shRNAs (Sh) that selectively silence specific groups of isoforms (FIG. 1A). Briefly, Sh1 knocks down all p53 isoforms, while Sh2 targets the long TAp53 (trans-activating) and Δ40p53 isoforms. Sh3 and Sh4 target the 5' UTR of the Δ133 isoforms (α, β and γ) and Sh5 and Sh6 respectively target the 3' end of the β and α isoforms.

Figure 1B:
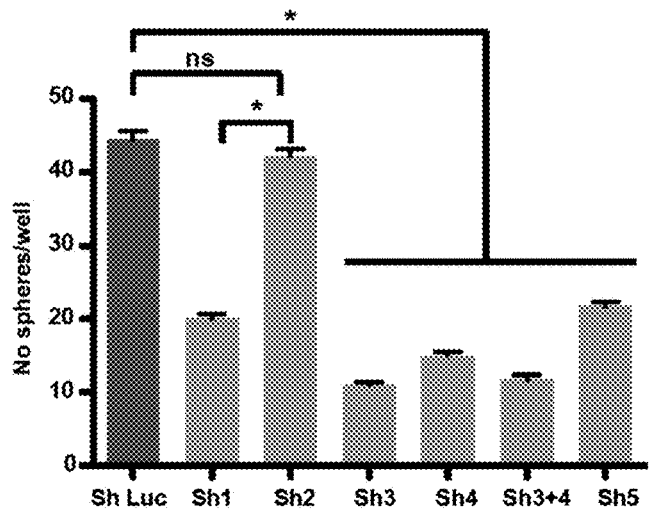
Figure 1C:
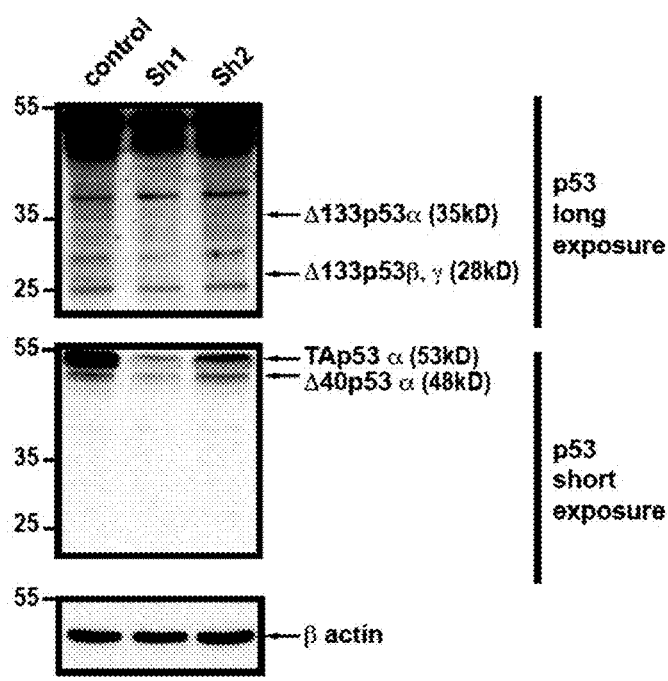
Figure 1D:
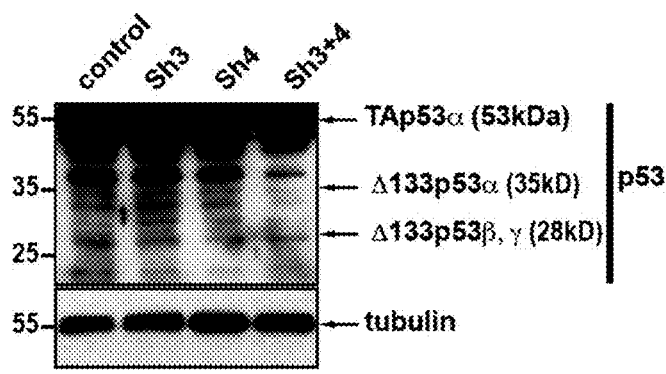
Figure 1E:
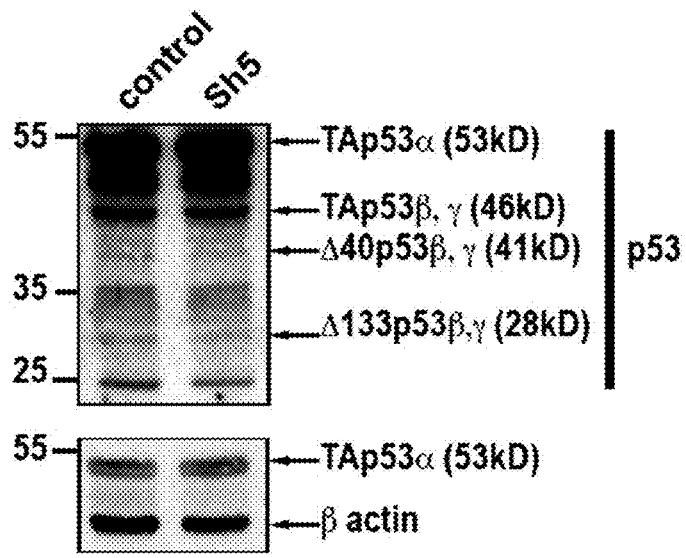
Figure 1F:
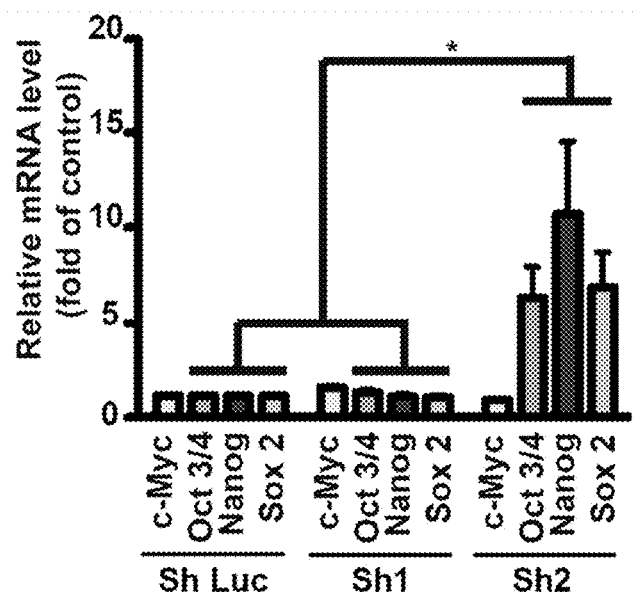
Figure 1G:
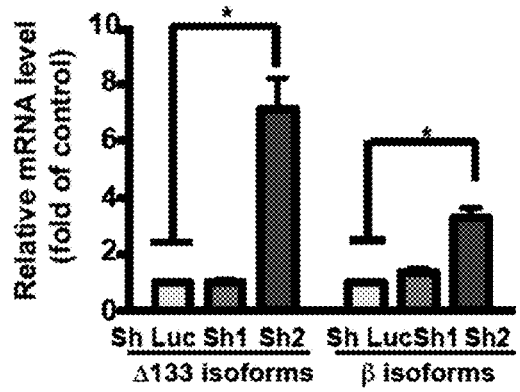

First we tested the ability of MCF-7 cells to form mammospheres, an assay widely used to assess CSC potential in vitro. Silencing of all p53 isoforms (with Sh1) resulted in a significant reduction of mammosphere formation compared to control cells, while knock-down of the TAp53 and Δ40p53 isoforms (Sh2) had no effect (FIGS. 1B and C). In parallel we measured the mRNA (FIG. 1F) and protein (FIG. 2A) expression of c-Myc, Sox 2, Oct 3/4 and Nanog, which are key regulators of cell pluripotency. TAp53 and Δ40p53 (Sh2) silencing resulted in increased expression of Oct 3/4, Nanog and Sox 2, but not of c-Myc, while depletion of all p53 isoforms (Sh1) had no effect. Moreover, depletion of TAp53 and Δ40p53 (Sh2) increased the expression of the Δ133 isoforms (FIG. 1G).

Figure 2A:
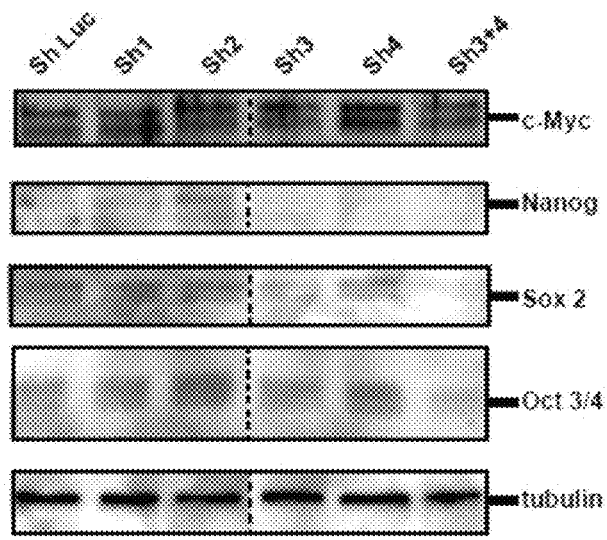
FIGS. 2A-2D. Analysis of key pluripotency/reprogramming genes expression following changes in p53 isoform levels. A. Western blot analysis of the expression of key pluripotency/reprogramming factors (c-Myc, Nanog, Sox 2 and Oct 3/4) after p53 isoform depletion using Sh1, Sh2, Sh3 or/and Sh4 and in control cells. B and C. Mammosphere quantification in MCF-7 cells upon p53 knock-down with Sh6 (n=3) (B) and western blot analysis of p53 depletion in the corresponding cells (C) and (D) Colospheres formation in SW480 colon carcinoma cells wherein Δ133p53 isoforms were knocked down using Sh3.
Figure 2B:
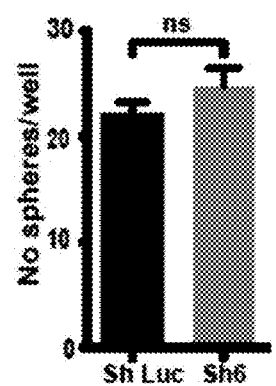
Figure 2C:
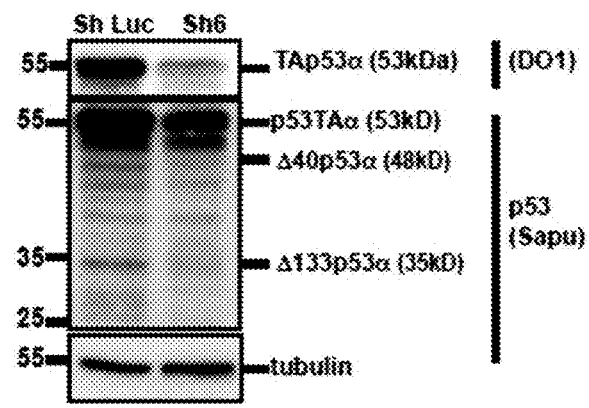

These results suggest that CSC potential in MCF-7 cells is not only regulated by TAp53α, which was previously identified as a suppressor of stemness. To investigate this hypothesis, we depleted all Δ133 isoforms using two different shRNAs (Sh3 and 4). Both shRNAs, used either alone or in combination, significantly reduced mammosphere formation in MCF-7 cells, suggesting that these isoforms are key regulators of CSC potential (FIGS. 1B and D). Accordingly, Oct 3/4, Nanog and Sox 2, were significantly down-regulated in Δ133 isoform-silenced cells (FIG. 2A). Again c-Myc expression was not affected. We then evaluated the effect of β and α isoform silencing. Mammosphere formation was significantly reduced in cells in which B isoforms where knocked down (Sh5; FIG. 1A). Silencing of all α isoforms (Sh6) did not affect mammosphere formation (Sh6; FIGS. 2B and 2C). Altogether these findings suggest that Δ133p53 (α, β, γ) isoforms are involved in regulating CSC potential in MCF-7 cells.

The inventors also investigated the ability of Δ133p53β isoform in promoting CSC potential in colon carcinoma cells SW480. For that, as described above Δ133p53 isoforms were knocked-down by using a shRNA (Sh3) in SW480 colon carcinoma cells.

Figure 2D:
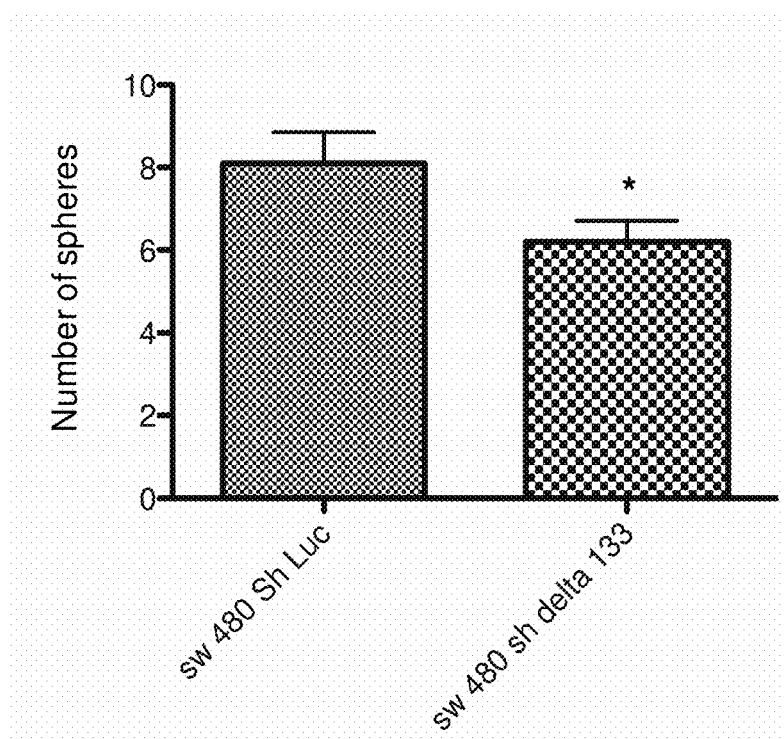

As demonstrated previously with MCF-7 breast cancer cell line, the results obtained with colon carcinoma cell line SW480 (FIG. 2D) also suggest that silencing Δ133p53β expression significantly reduced colospheres formation in these cells compared to control shLuc, indicating that these isoforms are key regulators of CSC potential in colon cancer also.

The same results may be expected with all cancers for which it has been demonstrated that transcriptional factors Sox 2, Oct 3/4 and/or Nanog are involved in CSCs induction from cancer cells.

Figure 3A:
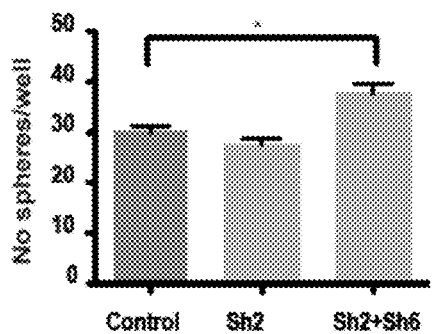
FIGS. 3A-3G. Δ133p53β promotes cancer stem cell potential in MCF-7 cells. A and B. Mammosphere quantification in MCF-7 cells after silencing with Sh2 (shRNAs against the TA and Δ40 isoforms) or with Sh2 and Sh6 (against the 3' end of the a isoforms) (A) and western blot analysis to confirm p53 depletion in the corresponding cell cultures (B) (n=3). C. Representative FACS dot blots for the double labeling of CD24 and CD44 in MCF-7 transduced with Sh Luc (Control), Sh2 or Sh2+6. D and E. Mammosphere quantification in MCF-7 cells after Δ133p53β or γ overexpression (D) and RT-qPCR analysis of c-Myc, Sox 2, Oct 3/4 and Nanog (E) expression in the corresponding cells (n=4). F. Mammosphere quantification in MCF-7 cells that overexpress Δ133p53β after harvesting and re-plating of the primary mammospheres. G. Mammosphere quantification in MCF-7 cells in which all p53 isoforms have been silenced with Sh1 and after expression in the same cells of Sh1-resistant Δ133p53β (n=3).
Figure 3B:
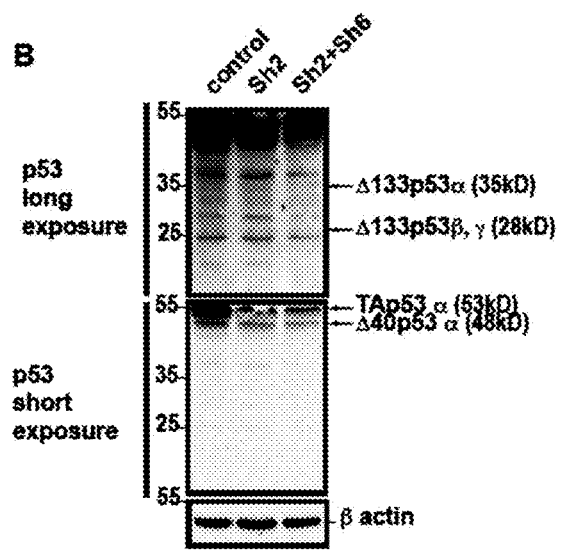
Figure 3C:
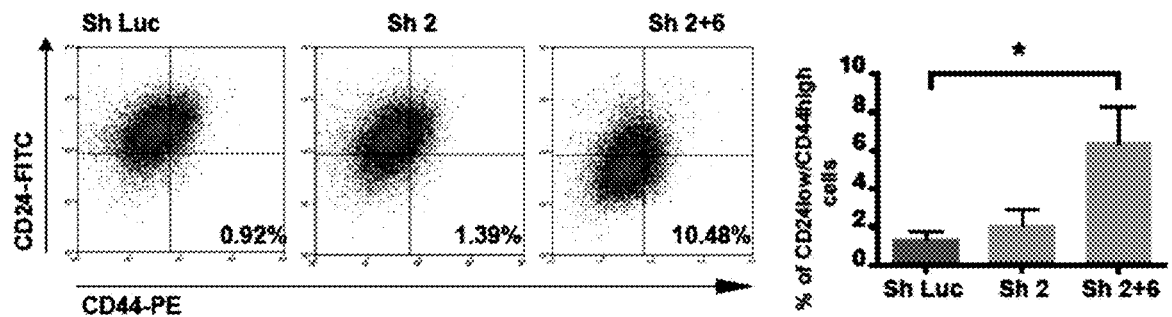
Figure 3D:
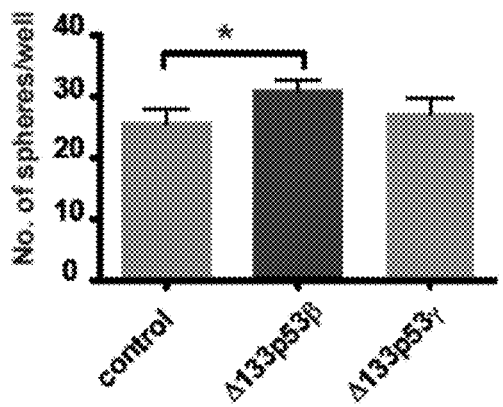
Figure 3E:
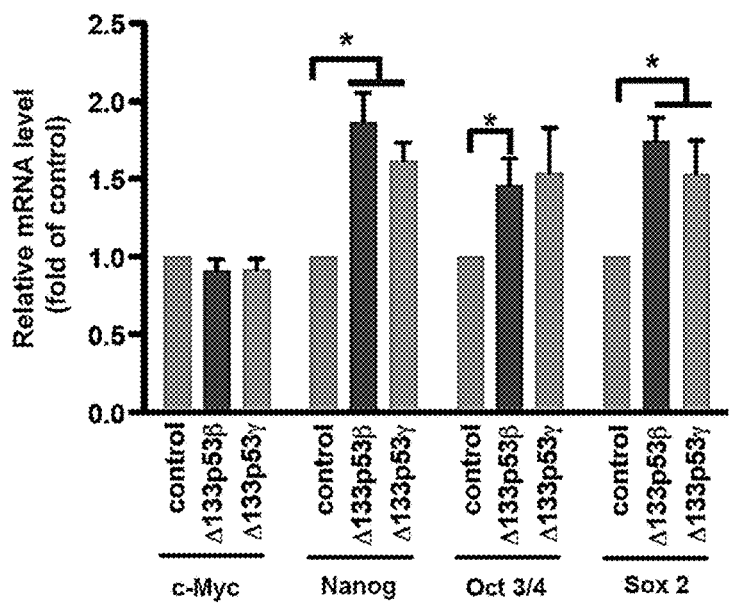
Figure 3F:
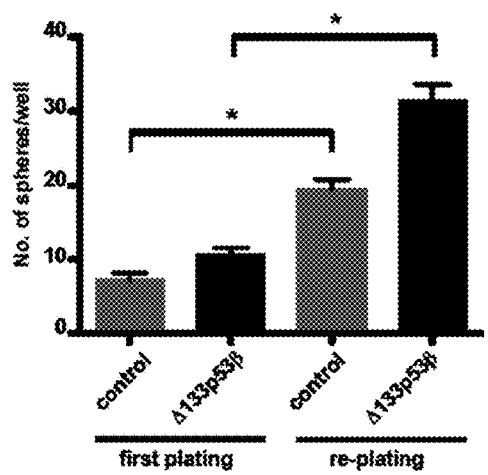
Figure 4:
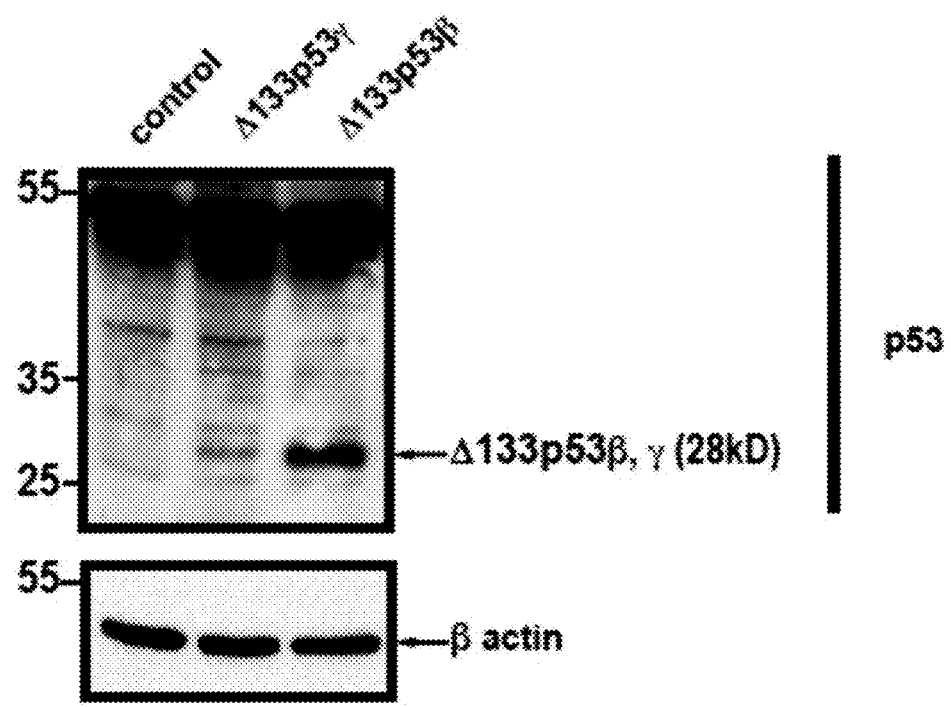
FIG. 4. Western blot analysis of p53 isoforms transduced in MCF-7 cells (Sapu antibody).

Example 3: The Δ133p53β Isoform Promotes Cancer Stem Cell Potential in MCF-7 Cells Indeed, mammosphere formation was significantly increased in MCF-7 that express only the Δ133p53β and Δ133p53γ isoforms following concomitant transduction with Sh2 and Sh6 (FIGS. 3A and 3B), suggesting an inhibitory effect of the Δ133p53α isoform. To confirm that sphere increase is indicative of CSC phenotype, we analyzed the proportion of CD44$^+$/CD24$^-$ cells because this subpopulation of cancer cells are considered to have CSC properties. Similarly to mammosphere formation variations, the proportion of CD44$^+$/CD24$^-$ cells was not affected by TAp53 and Δ40p53 isoform silencing with Sh2, whereas it was increased by co-transduction of Sh2 and Sh6 (FIG. 3C). To determine the specific contribution of the Δ133p53 (β and γ) isoforms in promoting mammosphere formation, we overexpressed them separately. In agreement with the previous results, over-expression of Δ133p53β significantly promoted mammosphere formation, while y isoform over-expression had a milder effect (FIG. 3D and FIG. 4). Moreover, Δ133p53β over-expression resulted in a significant increase of Sox 2, Nanog and Oct 3/4 expression, but not of c-Myc (FIG. 3E). In addition, mammosphere formed with Δ133p53β was higher after harvesting and re-plating of primary mammospheres, considered as the gold standard experiment to challenge CSC phenotype in vitro (FIG. 3F).

Figure 3G:
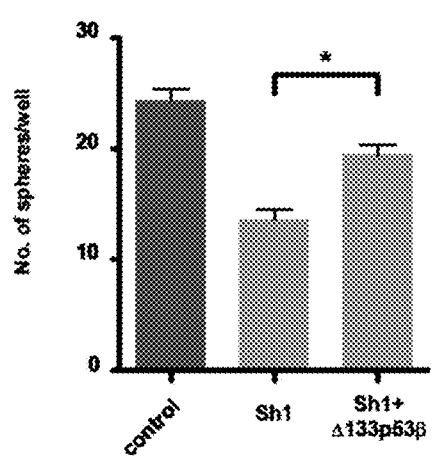

Finally, to confirm the role of the Δ133p53β isoform in promoting CSC potential in MCF-7 cells, we overexpressed a Sh1-resistant Δ133p53β isoform in MCF-7 cells in which all p53 isoforms had been knocked down with Sh1. As expected, expression of Sh1-resistant Δ133p53β rescued mammosphere formation (FIG. 3G).

Altogether these results indicate that the Δ133p53β isoform positively regulates CSC potential in MCF-7 breast cancer cells.

Figure 5E:
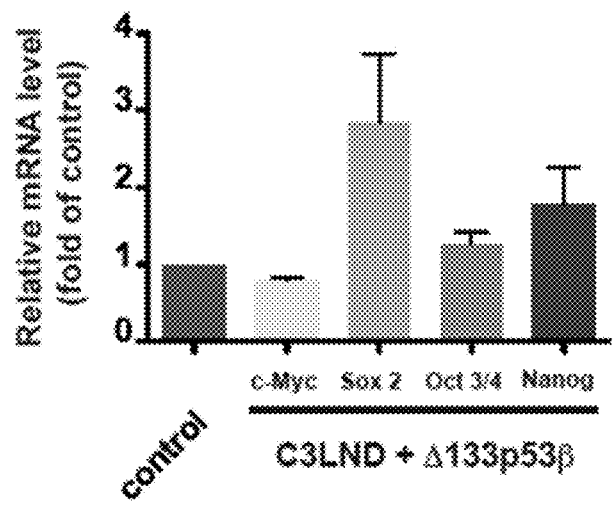

Example 4: High Δ133p53 Levels Correlate with Increased Metastatic Capacity and Mammosphere Formation Ability Increasing evidences suggest that CSC phenotype and metastasis development are closely linked. We therefore sought to determine whether the metastatic capacity of breast cancer cells was coupled to their CSC potential and Δ133p53 isoform expression. To this end, we used MDA-MB-231 D3H2LN cells, which can generate at low frequency lung metastasis when transplanted in immuno-deficient mice, to derive the highly cancer-prone and very metastatic C3LND cell line (see Methods in Example 1) (FIG. 5A). When this line was used for orthotopic transplantation experiments in nude mice, metastasis detection time was reduced from 82 days (with parental D3H2LN cells) to 20 days and lung metastases were detected in all transplanted animals (FIG. 5B). Although primary tumor growth was comparable in both cell lines (FIG. 5C), metastasis development was significantly accelerated in C3LND cells as indicated by bioluminescence quantification (FIG. 5D).

Figure 5F:
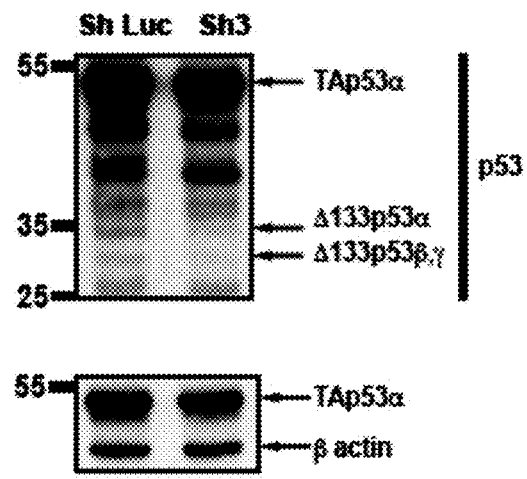
Figure 6A:
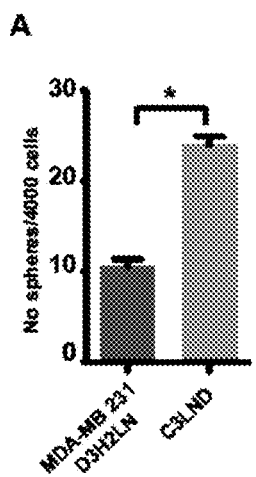
FIGS. 6A-6K. Evaluation of the cancer stem cell features of the MDA-MB 231 D3H2LN and C3LND cell lines. A. Mammosphere quantification in the modestly metastatic, parental MDA-MB-231 D3H2LN and the derived, highly metastatic C3LND cell line (n=3). B. RT-qPCR analysis of Δ133p53 (α, β and γ) isoforms expression in MDA-MB-231 D3H2LN and C3LND cells (n=4). C. RT-qPCR quantification of c-Myc, Oct 3/4, Nanog and Sox 2 expression in MDA-MB-231 D3H2LN and C3LND cells (n=4). D. Western blot analysis of Δ133p53β-Flag transduced in MDA-MB 231 D3H2LN cells (Flag antibody). E. RT-qPCR analysis of c-Myc, Oct 3/4, Nanog and Sox 2 expression in MDA-MB-231 D3H2LN cells after Δ133p53β overexpression (n=4). F. Mammosphere quantification in MDA-MB-231 D3H2LN cells that overexpress Δ133p53β. G. Mammosphere quantification in MDA-MB-231 C3LND transduced with Sh3 (n=3). H. RT-qPCR analysis of Δ133p53 (α, β and γ) isoforms expression in MDA-MB-231 C3LND transduced with Sh3. I. RT-qPCR quantification of c-Myc, Oct 3/4, Nanog and Sox 2 expression in MDA-MB-231 C3LND cells transduced with Sh3 (n=4). J. Representative FACS dot plots for the double labeling of CD44 and CD24 in MDA-MB-231 C3LND transduced with Sh Luc (Control), or Sh3. K. Quantification of distant metastasis in brain and femur using bioluminescence imaging (n=7/5) 25 days after the implantation.
Figure 6B:
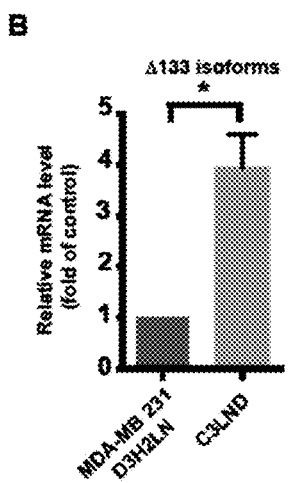
Figure 6C:
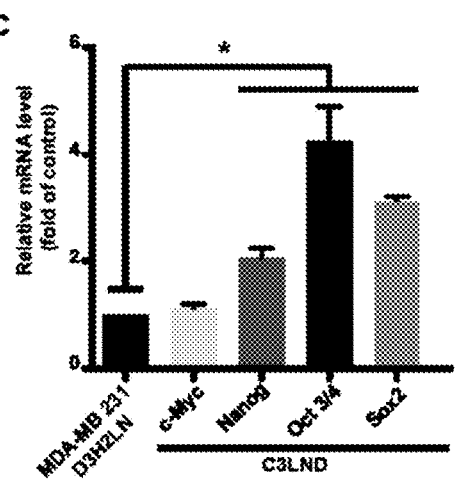
Figure 6D:
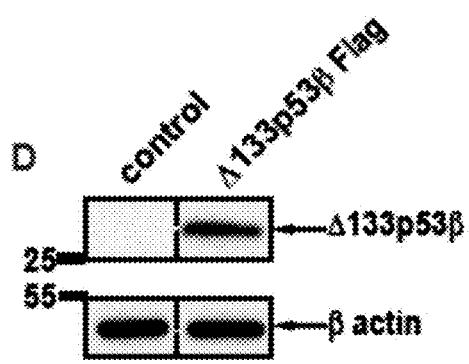
Figure 6E:
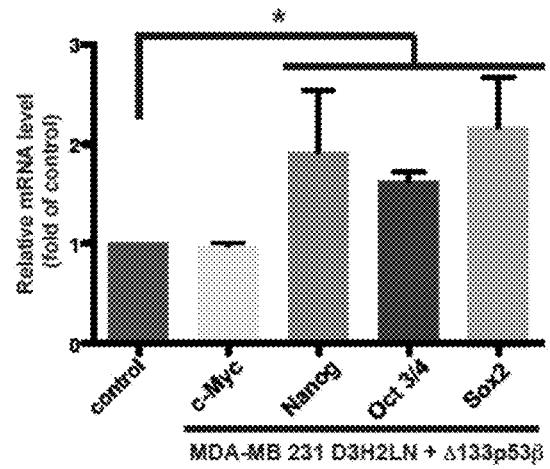
Figure 6F:
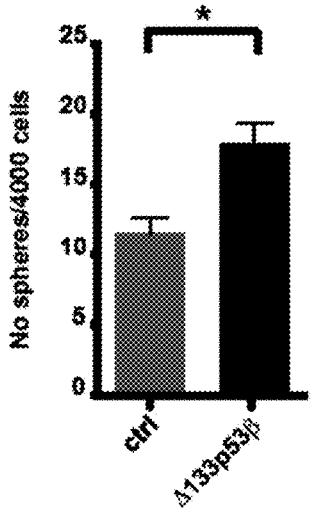

Evaluation of mammosphere formation in D3H2LN and C3LND cells showed that these latter formed two-times more mammospheres (FIG. 6A). Similarly, Δ133p53 isoforms expression was 3-fold higher and Oct 3/4, Nanog and Sox 2 levels were 2-3-fold higher in C3LND (FIGS. 6B and C). c-Myc expression was comparable in the two cells lines. We then asked whether pluripotency factor expression could be affected by changes in Δ133p53 expression. Overexpression of Δ133p53β in D3H2LN cells resulted in a significant increase of Oct 3/4, Nanog and Sox 2 expression, whereas c-Myc level was not affected, consistent with data obtained in MCF-7 cells (FIGS. 6D and 6E). Similar results were obtained in C3LND cells (FIG. 5F). In complete agreement with observations in MCF-7, Δ133p53β overexpression in D3H2LN cells resulted in a significant increase of mammosphere formation (FIG. 6F).

Figure 5G:
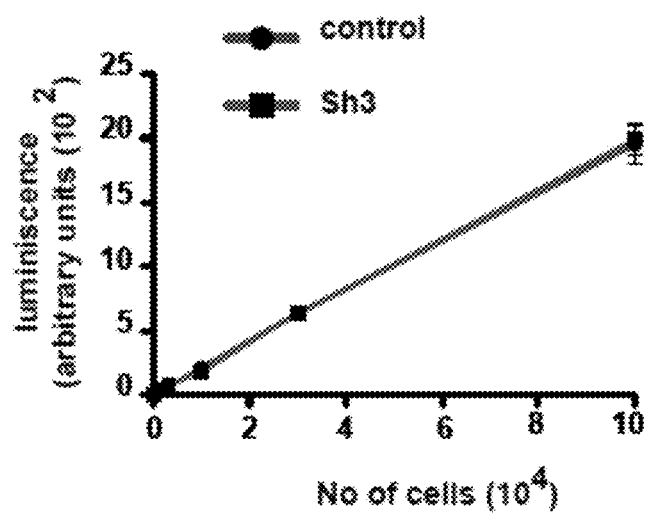
Figure 6G:
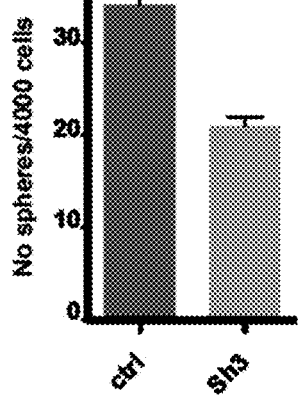
Figure 6H:
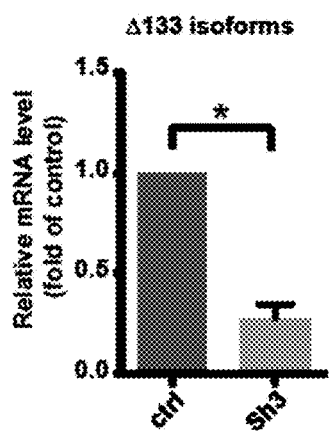
Figure 6I:
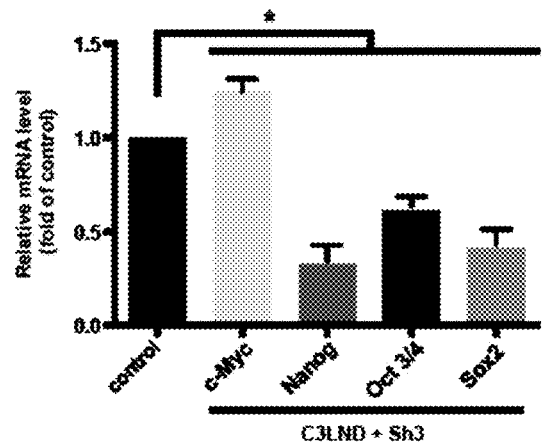
Figure 6J:
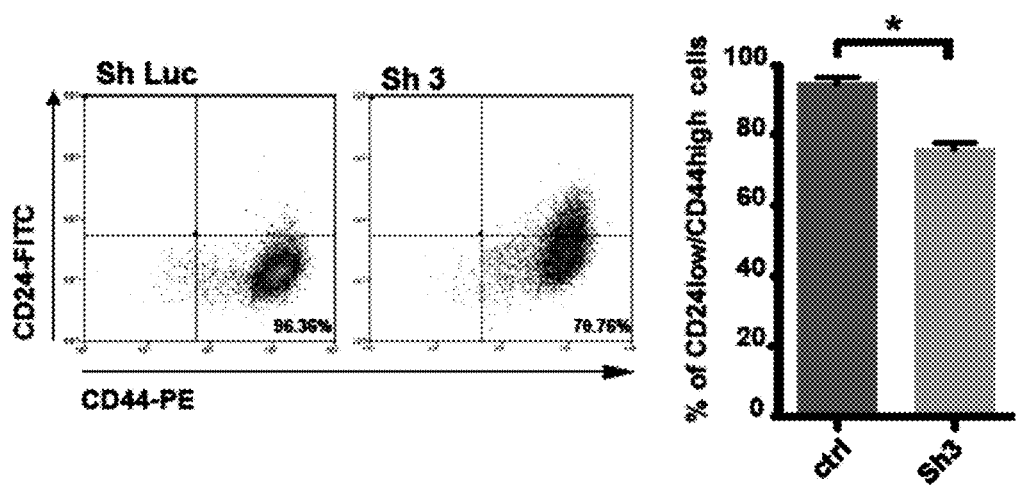
Figure 6K:
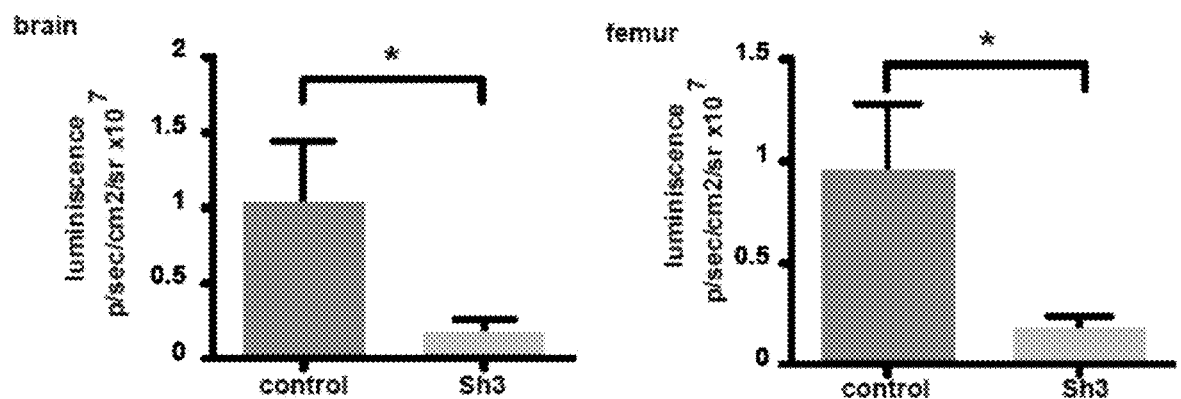

Conversely, Sh3-mediated knock-down of the Δ133p53 isoforms in C3LND cells led to a significant reduction of sphere formation associated with a marked decrease of Oct 3/4, Nanog and Sox 2 expression and a small increase of c-Myc level (FIGS. 6G, H and I), whereas Δ133p53β transduction increased them (FIG. 5F). In agreement, transduction of Sh3 decreased the proportion of $CD44^+/CD24^-$ cells (FIG. 6J) Finally, after intracardiac injection in athymic mice, Sh3-transduced C3LND cells were less prone to metastasize to distant sites compared to control cells (FIG. 6K and FIG. 5G). In summary, the more metastatic C3LND cell line is characterized by higher CSC potential, as indicated by mammosphere formation, and increased Δ133p53 as well as Oct 3/4, Nanog and Sox 2 (but not c-Myc) expression compared to the parental D3H2LN cell line. Δ133p53 overexpression increases the pluripotency potential of D3H2LN cells, while its knock-down produces the opposite effect and a marked reduction of the metastatic potential of these cells when grafted in mice. Altogether these data suggest that the Δ133p53β isoform specifically regulates CSC activity and metastasis formation through modulation of the expression of key players in the maintenance of cell pluripotency and reprogramming (i.e., Oct 3/4, Nanog and Sox 2).

Figure 7A:
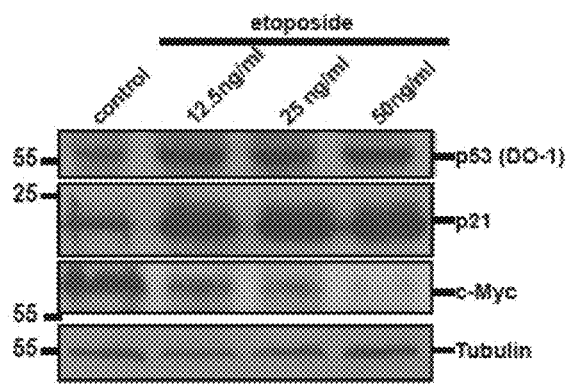
FIGS. 7A-7I. Chemotherapy treatment of MCF-7 breast cancer cells up-regulates Δ133p53 isoform expression and activates key pluripotency genes. A. Western blot analysis of p53, p21 and c-Myc expression in MCF-7 cells after treatment with increasing doses of etoposide for 16 hours (DO1 antibody). B. RT-qPCR analysis of c-Myc expression in MCF-7 cells upon treatment with increasing doses of etoposide (n=4). C. RT-qPCR analysis of Δ133p53 (α, β and γ) isoforms expression in MCF-7 cells after etoposide treatment (n=4). D. Western blot analysis of p53 isoform expression in MCF-7 cells after etoposide treatment. (Sapu antibody). E. RT-qPCR analysis of Sox 2, Oct 3/4 and Nanog expression in MCF-7 cells upon treatment with increasing doses of etoposide (n=4). F. RT-qPCR analysis of Δ133p53 (α, β and γ), Sox 2, Oct 3/4 and Nanog expression in control and MCF-7 cells transduced with Sh3 upon etoposide treatment (n=4). G. Mammosphere quantification in MCF-7 cells transduced with Sh2 and treated with 50 ng/ml/day etoposide for 7 days (n=3). H and I. RT-qPCR analysis of c-Myc, Nanog, Oct 3/4 and Sox 2 (H) and Δ133p53 (α, β and γ) isoforms (I) expression in MCF-7 cells transduced with Sh2 and treated with 50 ng/ml/day etoposide for 7 days (n=4).
Figure 7B:
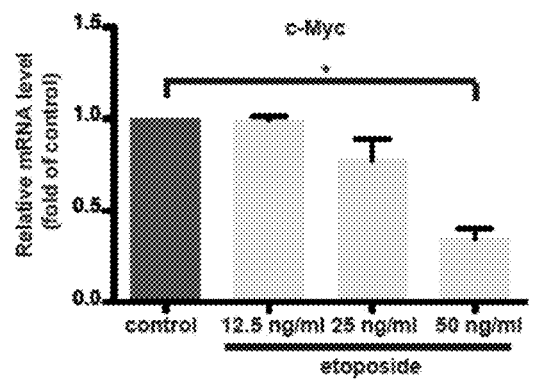
Figure 7C:
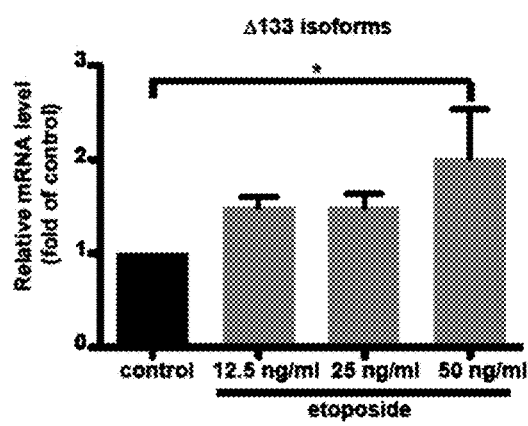
Figure 7D:
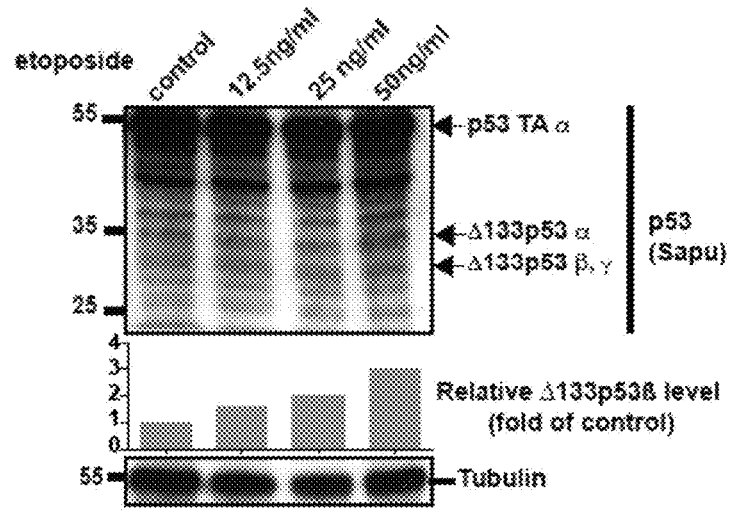
Figure 7E:
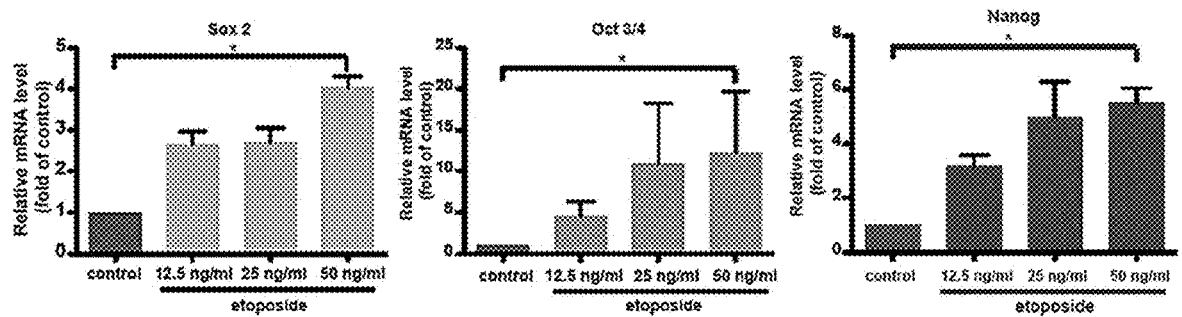

Example 5: Chemotherapy Treatment of Breast Cancer Cell Lines Up-Regulates the Expression of Δ133p53 Isoforms and Activates Key Reprogramming Genes Topoisomerase II inhibitors (etoposide-VP16 and doxorubicin) are frequently used as adjuvant chemotherapy treatment for several cancer types alone or in combination with other drugs (cisplatin most frequently). Topoisomerase II inhibitors induce double strand DNA breaks, a genotoxic stress that strongly activates p53 signaling. Up-regulation of TAp53 should be beneficial due to its ability to induce cell cycle arrest, apoptosis and to negatively regulate cell reprogramming. We thus assessed whether etoposide could affect Δ133p53 expression and CSC potential in breast cancer cell lines. Increasing concentrations of etoposide resulted in TAp53α stabilization in MCF-7. As expected, p21 expression (positively regulated by p53) was increased, whereas c-Myc expression (negatively regulated by p53) was reduced (FIG. 7A), as also confirmed by RT-qPCR quantification (FIG. 7B). Moreover, RT-qPCR and western blot analysis showed that, upon etoposide treatment, Δ133p53 isoforms (FIGS. 7C and 7D) as well as Oct 3/4, Nanog and Sox 2 (FIG. 7E) were strongly up-regulated in a dose-dependent manner. This last result is particularly intriguing because TAp53α, which is considered as a negative regulator of pluripotency/reprogramming genes, is stabilized and transcriptionally active.

Figure 7F:
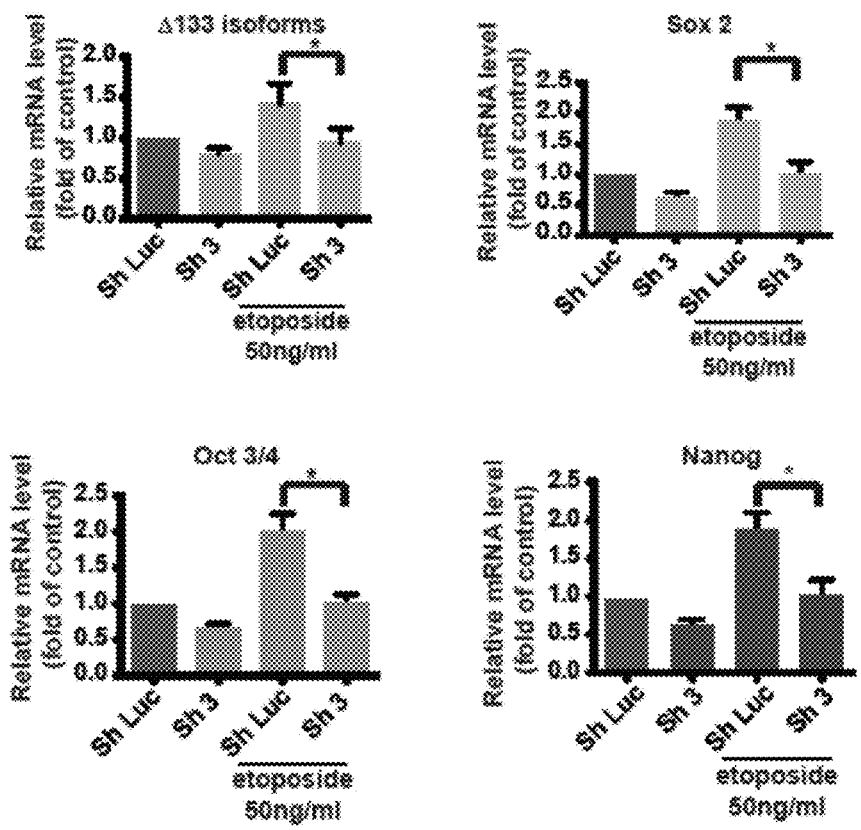

To determine whether Oct 3/4, Nanog and Sox2 up-regulation in this condition required Δ133p53 expression, we transduced MCF-7 cells with Sh3 to specifically knock them down. Oct 3/4, Nanog and Sox2 expression was reduced in both treated and etoposide untreated cells following Δ133p53 silencing (FIG. 7F), confirming the specific role of Δ133p53 isoforms in the regulation of genes involved in cell pluripotency/reprogramming.

Figure 7G:
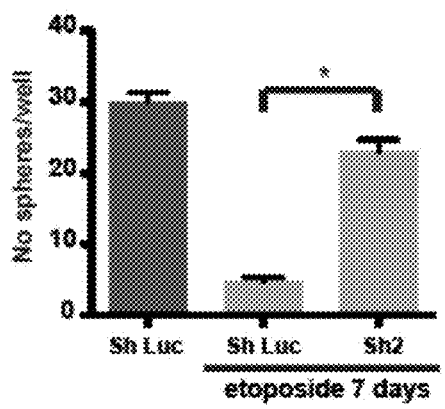
Figure 7H:
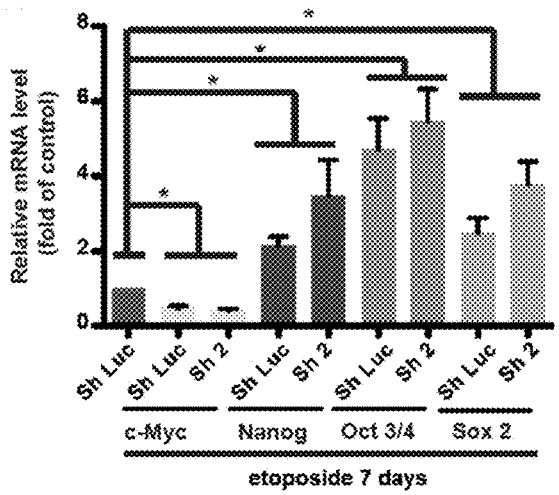
Figure 7I:
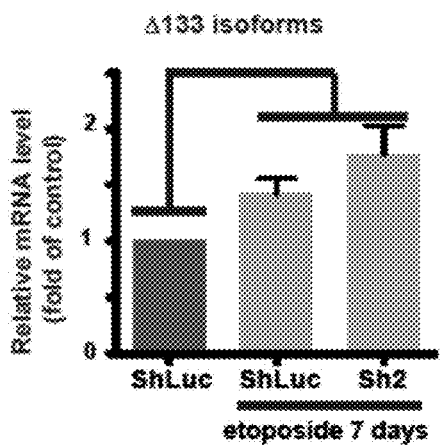

Finally, we evaluated the effect of etoposide treatment on mammosphere formation of Sh2-transduced MCF-7 cells. Etoposide treatment in control cells (active TAp53) significantly reduced mammosphere formation, whereas it did not have any significant effect in Sh2-transduced cells (FIG. 7G). Moreover, Δ133p53 level was correlated with the expression of reprogramming genes (FIGS. 7H and 7I). These data indicate that TAp53 and Δ133p53β have an antagonistic action in sphere formation.

Figure 8A:
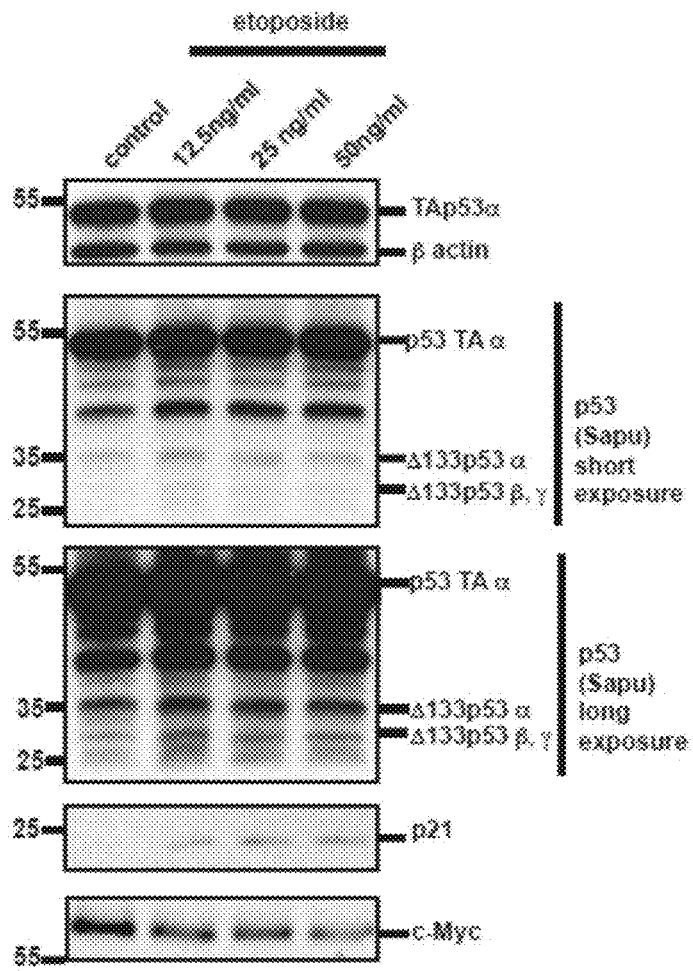
FIGS. 8A-8D. Etoposide treatment of MDA-MB-231 D3H2LN cells up-regulates Δ133p53 isoform expression and activates key pluripotency genes. A. Western blot analysis of p53, p21 and c-Myc expression in MDA-MB-231 D3H2LN cells after treatment with increasing doses of etoposide for 16 hours. B. RT-qPCR analysis of c-Myc expression in MDA-MB-231 D3H2LN cells upon treatment with increasing doses of etoposide (n=4). C. RT-qPCR analysis of Δ133p53 (α, β and γ) isoforms expression in MDA-MB-231 D3H2LN cells after etoposide treatment (n=4). D. RT-qPCR analysis of Nanog, Oct 3/4 and Sox 2 expression in MDA-MB-231 D3H2LN cells upon treatment with increasing doses of etoposide (n=4).
Figure 8B:
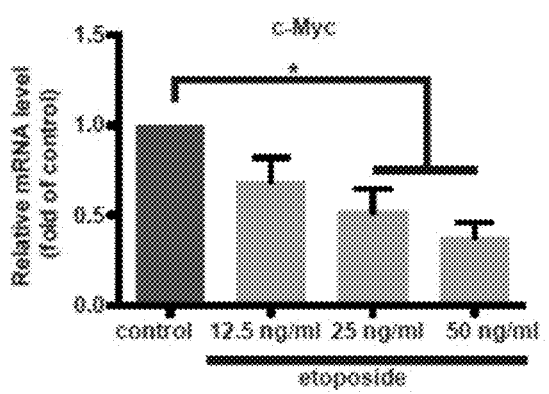
Figure 8C:
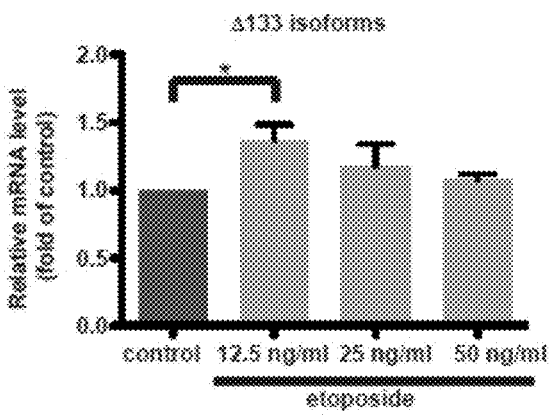
Figure 8D:
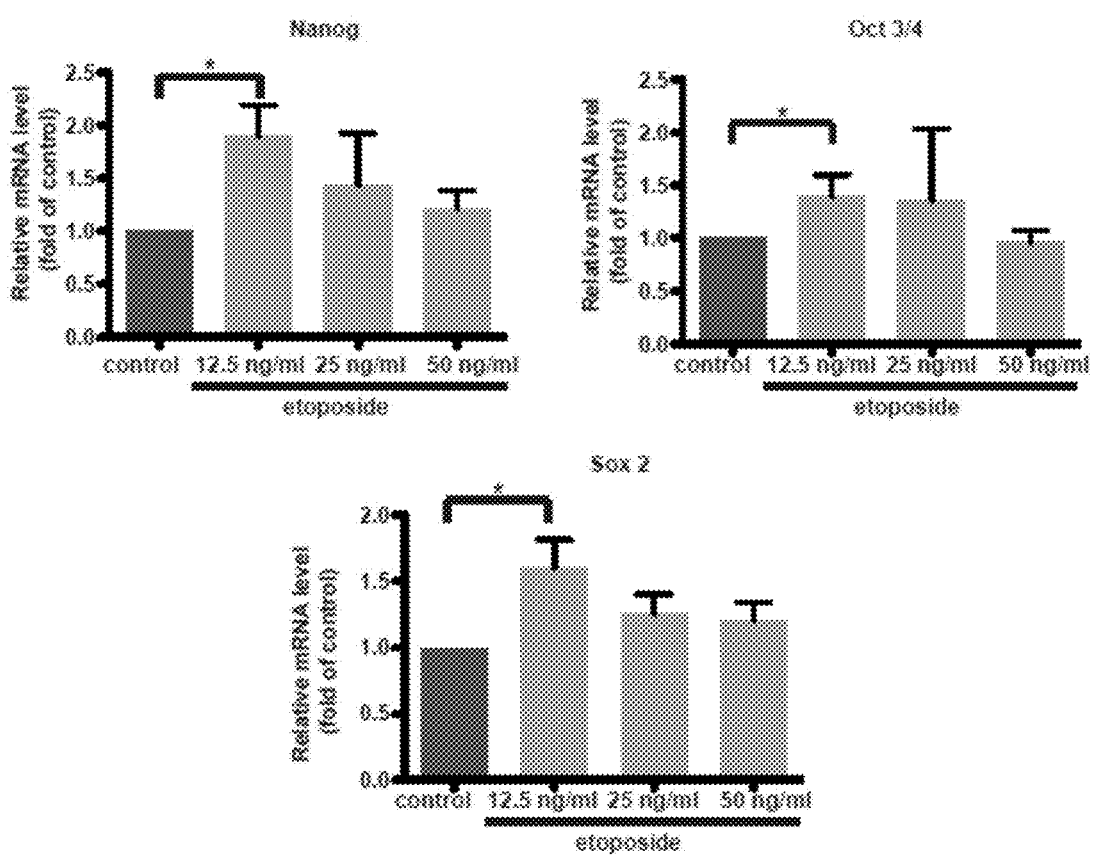

We then evaluated the effects of etoposide treatment in MDA-MB-231 D3H2LN cells. This cell line harbors the p53 R280K mutation and corresponds to a triple negative breast cancer type. This mutation is present in TAp53 and also in Δ133p53 isoforms. Incubation with increasing concentrations of etoposide did not affect TAp53 expression, and p21 expression was only weakly increased (FIG. 8A). This effect of mutant p53 protein on p21 expression was already described in literature (Bieging et al., 2014). Interestingly, c-Myc expression was significantly down-regulated, (FIGS. 8A and 8B). The expression of Δ133p53 isoforms was up-regulated (FIGS. 8A and 8C), but not in a dose-dependent manner as observed in MCF-7 cells. Similarly, the expression of Nanog, Sox 2 and Oct 3/4 (FIG. 8D) was also up-regulated following incubation with etoposide, like for Δ133p53 isoforms.

All together these data suggest that, in human breast cancer cells, the topoisomerase II inhibitor etoposide increases Δ133p53 expression, resulting in the activation of the reprogramming genes Nanog, Sox 2 and Oct 3/4.

BIBLIOGRAPHIC REFERENCES

Alix-Panabières C, Pantel K. Circulating tumor cells: liquid biopsy of cancer. Clin Chem. 2013 January;59 (1): 110-8.
Anensen N, Oyan A M, Bourdon J C et al. (2006) A distinct p53 protein isoform signature reflects the onset of induction chemotherapy for acute myeloid leukemia. Clin Cancer Res 12:3985-92

Avery-Kiejda, K. A., Morten, B., Wong-Brown, M. W., Mathe, A., and Scott, R. J. (2014). The relative mRNA expression of p53 isoforms in breast cancer is associated with clinical features and outcome. Carcinogenesis 35, 586-596.

Bernard H, Garmy-Susini B, Ainaoui N, Van Den Berghe L, Peurichard A, Javerzat S, Bikfalvi A, Lane D P, Bourdon J C, Prats A C. (2013) The p53 isoform, Δ133p53α, stimulates angiogenesis and tumour progression. Oncogene. 2013 Apr. 25; 32 (17): 2150-60

Bieging, K. T., Mello, S. S., and Attardi, L. D. (2014). Unravelling mechanisms of p53-mediated tumour suppression. Nature reviews Cancer 14, 359-370.

Boldrup, L., Bourdon, J. C., Coates, P. J., Sjostrom, B., and Nylander, K. (2007). Expression of p53 isoforms in squamous cell carcinoma of the head and neck. European journal of cancer 43, 617-623.

Bourdon, J. C., Fernandes, K., Murray-Zmijewski, F., Liu, G., Diot, A., Xirodimas, D. P., Saville, M. K., and Lane, D. P. (2005). p53 isoforms can regulate p53 transcriptional activity. Genes & development 19, 2122-2137.

Bourdon, J. C. (2007). p53 and its isoforms in cancer. Br J Cancer 97, 277-282.

Bourdon, J. C., Khoury, M. P., Diot, A., Baker, L., Fernandes, K., Aoubala, M., Quinlan, P., Purdie, C. A., Jordan, L. B., Prats, A. C., et al. (2011). p53 mutant breast cancer patients expressing p53gamma have as good a prognosis as wild-type p53 breast cancer patients. Breast cancer research: BCR 13, R7.

Charras G. T. (2008). A short history of blebbing. Journal of Microscopy, Vol. 231. Pt 3 pp. 446-478.

Cheng L., Ramesh A. V., Flesken-Nikitin A., Choi J., Nikitin A. Y. (2010) Mouse models for cancer stem cell research. *Toxicologic Pathology*. 2010; 38 (1): 62-71.

Chiou S-H., Wang M-L., Chou Y-T., Chen C-J;, Hong C-F., Hsieh W-J., Chang H-T., Chen Y-S., Lin T-W., Hsu H-S., Wu C-W. (2010) Coexpression of Oct4 and Nanog Enhances Malignancy in Lung Adenocarcinoma by Inducing Cancer Stem Cell-Like Properties and Epithelial Mesenchymal Transdifferentiation. Cancer Res; 70 (24) December 15.

Davidson, W. R., Kari, C., Ren, Q., Daroczi, B., Dicker, A. P., and Rodeck, U. Differential regulation of p53 function by the N-terminal DeltaNp53 and Delta113p53 isoforms in zebrafish embryos. BMC Dev Biol 10, 102.

Dovey, M. C., and Zon, L. I. (2009) Defining cancer stem cells by xenotransplantation in zebrafish, Meth. Mol. Biol. 568:1-5 (Chapter)

Fujita, K., Mondal, A. M., Horikawa, I., Nguyen, G. H., Kumamoto, K., Sohn, J. J., Bowman, E. D., Mathe, E. A., Schetter, A. J., Pine, S. R., et al. (2009). p53 isoforms Delta133p53 and p53beta are endogenous regulators of replicative cellular senescence. Nat Cell Biol 11, 1135-1142.

Gadea, G., de Toledo, M., Anguille, C., and Roux, P. (2007a). Loss of p53 promotes RhoA-ROCK-dependent cell migration and invasion in 3D matrices. J Cell Biol 178, 23-30.

Gadea, G., de Toledo, M., Anguille, C., and Roux, P. (2007b). Loss of p53 promotes RhoA-ROCK-dependent cell migration and invasion in 3D matrices. The Journal of cell biology 178, 23-30.

Gavert N, Vivanti A, Hazin J, Brabletz T, Ben-Ze'ev A. L1-mediated colon cancer cell metastasis does not require changes in EMT and cancer stem cell markers. Mol Cancer Res. 2011 January; 9 (1): 14-24.

Golebiewska A, Brons N H, Bjerkvig R, Niclou S P. Critical appraisal of the side population assay in stem cell and cancer stem cell research. Cell Stem Cell. 2011 Feb. 4; 8 (2): 136-47.

Grez, M., et al. (1990). Embryonic stem cell virus, a recombinant murine retrovirus with expression in embryonic stem cells. Proc. Natl. Acad. Sci. USA 87:9202-9206.

Hafsi, H., Santos-Silva, D., Courtois-Cox, S., and Hainaut, P. (2013). Effects of Delta40p53, an isoform of p53 lacking the N-terminus, on transactivation capacity of the tumor suppressor protein p53. BMC cancer 13, 134.

Hofstetter, G., Berger, A., Berger, R., Zoric, A., Braicu, E. I., Reimer, D., Fiegl, H., Marth, C., Zeimet, A. G., Ulmer, H., et al. (2012). The N-terminally truncated p53 isoform Delta40p53 influences prognosis in mucinous ovarian cancer. International journal of gynecological cancer: official journal of the International Gynecological Cancer Society 22, 372-379.

Hong, H., Takahashi, K., Ichisaka, T., Aoi, T., Kanagawa, O., Nakagawa, M., Okita, K., and Yamanaka, S. (2009). Suppression of induced pluripotent stem cell generation by the p53-p21 pathway. Nature 460, 1132-1135.

Jeter C R., Liu B., Liu X., Chen X., Liu C., Calhoun-Davis T., Repass J., Zaehres H., Shen J J., Tang D G., (2011). NANOG promotes cancer stem cells characteristics and prostate cancer resistance to androgen deprivation. Oncogene 30, 3833-3845.

Kawamura, T., Suzuki, J., Wang, Y. V., Menendez, S., Morera, L. B., Raya, A., Wahl, G. M., and Izpisua Belmonte, J. C. (2009). Linking the p53 tumour suppressor pathway to somatic cell reprogramming. Nature 460, 1140-1144.

Khoury, M. P., and Bourdon, J. C. (2011). p53 Isoforms: An Intracellular Microprocessor? Genes & cancer 2, 453-465.

Lane, D. P. (1992). Cancer. p53, guardian of the genome. Nature 358, 15-16.

Li, M., He, Y., Dubois, W., Wu, X., Shi, J., and Huang, J. (2012). Distinct regulatory mechanisms and functions for p53-activated and p53-repressed DNA damage response genes in embryonic stem cells. Mol Cell 46, 30-42.

Liu, Y., Dong, Q. Z., Zhao, Y., Dong, X. J., Miao, Y., Dai, S. D., Yang, Z. Q., Zhang, D., Wang, Y., Li, Q. C., et al. (2009). P120-catenin isoforms 1A and 3A differently affect invasion and proliferation of lung cancer cells. Exp Cell Res 315, 890-898.

Mavroudis D. Circulating cancer cells. Ann Oncol. 2010 October; 21 Suppl 7: vii95-100.

Miller, A. D. & Rosman, G. J. (1989). Improved retroviral vectors for gene transfer and expression. BioTechniques 7:980-990. Muller, P. A., Caswell, P. T., Doyle, B., Iwanicki, M. P., Tan, E. H., Karim, S., Lukashchuk, N., Gillespie, D. A., Ludwig, R. L., Gosselin, P., et al. (2009). Mutant p53 drives invasion by promoting integrin recycling. Cell 139, 1327-1341.

Norikatsu Miyoshi, Hideshi Ishiia,b,1, Ken-ichi Nagaia, Hiromitsu Hoshinoa, Koshi Mimorib, Fumiaki Tanakab, Hiroaki Naganoa, Mitsugu Sekimotoa, Yuichiro Dokia, and Masaki Mori. (2010). Defined factors induce reprogramming of gastrointestinal cancer cells. 40-45|PNAS vol. 107 | no. 1.

Oshima N., Yamada Y., Nagayama S., Kawada K., Hasegawa S., Okabe H., Sakai Y., TAoi T. (2014). Induction of Cancer Stem Cell Properties in Colon CancerCells by Defined Factors. PLOS ONE|www.plosone.org, Volume 9|Issue 7|e101735.

Roger, L., Jullien, L., Gire, V., and Roux, P. (2010). Gain of oncogenic function of p53 mutants regulates E-cadherin expression. uncoupled from cell invasion in colon cancer cells. Journal of cell science 123, 1295-1305.

Sarig, R., Rivlin, N., Brosh, R., Bornstein, C., Kamer, I., Ezra, O., Molchadsky, A., Goldfinger, N., Brenner, O., and Rotter, V. (2010). Mutant p53 facilitates somatic cell reprogramming and augments the malignant potential of reprogrammed cells. J Exp Med 207, 2127-2140.

Schatton T, Frank N Y, Frank M H. (2009) Identification and targeting of cancer stem cells. BioEssays: news and reviews in molecular, cellular and developmental biology. 2009 October; 31 (10): 1038-49.

Takahashi, R., Markovic, S. N., and Scrable, H. J. (2014). Dominant effects of Delta40p53 on p53 function and melanoma cell fate. The Journal of investigative dermatology 134, 791-800.

Telford W G. Stem cell side population analysis and sorting using DyeCycle violet. Curr Protoc Cytom. 2010 January; Chapter 9: Unit9.30.

Tirino V, Desiderio V, Paino F, De Rosa A, Papaccio F, La Noce M, Laino L, De Francesco F, Papaccio G. Cancer stem cells in solid tumors: an overview and new approaches for their isolation and characterization. FASEB J. 2013 January; 27 (1): 13-24.

Utikal, J., Polo, J. M., Stadtfeld, M., Maherali, N., Kulalert, W., Walsh, R. M., Khalil, A., Rheinwald, J. G., and Hochedlinger, K. (2009). Immortalization eliminates a roadblock during cellular reprogramming into iPS cells. Nature 460, 1145-1148.

Vinot, S., Anguille, C., de Toledo, M., Gadea, G., and Roux, P. (2008). Analysis of cell migration and its regulation by Rho GTPases and p53 in a three-dimensional environment. Methods Enzymol 439, 413-424.

Vojtesek et al., Conformational changes in p53 analysed using new antibodies to the core DNA binding domain of the protein. Oncogene. 1995 Jan. 19; 10 (2): 389-93

WO2009/029054.
WO2010/1431683.
WO2011/000891.
WO2012/044979.

Zhao, T., and Xu, Y. (2010). p53 and stem cells: new developments and new concerns. Trends Cell Biol 20, 170-175.

---

The invention claimed is:

1. A method for predicting a risk of cancer metastasis in a subject suffering from cancer from a cancer sample of said subject and treating said subject, comprising:
   a) detecting sphere-forming cancer cells expressing Δ133p53β isoform, Δ133p53γ isoform, or both Δ133p53β and Δ133p53γ isoforms in said cancer sample;
   b) concluding to the presence of a significant risk of cancer metastasis in said subject if sphere-forming cancer cells expressing Δ133p53β isoform, Δ133p53γ isoform, or both Δ133p53β and Δ133p53γ isoforms are detected and to the absence of a significant risk of cancer metastasis in said subject if sphere-forming cancer cells expressing Δ133p53β isoform, Δ133p53γ isoform, or both Δ133p53β and Δ133p53γ isoforms are not detected; and
   c) treating said subject, wherein
   (i) if the subject is determined as being at a significant risk of cancer metastasis, an agent reducing Δ133p53β isoform, Δ133p53γ isoform, or both Δ133p53β and Δ133p53γ isoforms expression and an anticancer treatment is administered to the subject, or
   (ii) if the subject is determined as not being at a significant risk of cancer metastasis, an anticancer treatment is administered to the subject,
      wherein the agent reducing Δ133p53β isoform, Δ133p53γ isoform, or both Δ133p53β and Δ133p53γ isoforms expression is antisense RNA or interfering RNA (iRNA).

2. The method according to claim 1, wherein the subject is suffering from one or more of:
   (i) solid cancers selected from the group consisting of breast cancer, ovarian cancer, pancreatic cancer, throat cancer, and gastrointestinal cancer including colorectal cancer, oesophageal cancer, gastric cancer, pancreatic cancer, hepatocellular carcinoma, cholangiocellular cancer and teratocarcinoma, and
   (ii) hematopoietic cancers selected from leukaemias and lymphomas.

3. The method according to claim 2, wherein the subject is suffering from breast cancer or colorectal cancer.

4. The method according to claim 1, wherein the cancer sample from which the expression level of Δ133p53β isoform, Δ133p53γ isoform, or both Δ133p53β and Δ133p53γ isoforms is measured in step a) is selected from:
  (i) a cancer biopsy, a complete or partial cancer surgical resection, and
  (ii) a blood sample.

5. The method according to claim 1, wherein sphere-forming cancer cells expressing Δ133p53β isoform or both Δ133p53β and Δ133p53γ isoforms in said cancer sample are detected in step a).

6. A method for predicting a risk of cancer metastasis in a subject suffering from cancer from a cancer sample of said subject and treating said subject, comprising:
  a) detecting sphere-forming cancer cells expressing Δ133p53β isoform, Δ133p53γ isoform, or both Δ133p53β and Δ133p53γ isoforms in said cancer sample;
  b) concluding to the presence of a significant risk of cancer metastasis in said subject if sphere-forming cancer cells expressing Δ133p53β isoform, Δ133p53γ isoform, or both Δ133p53β and Δ133p53γ isoforms are detected and to the absence of a significant risk of cancer metastasis in said subject if sphere-forming cancer cells expressing Δ133p53β isoform, Δ133p53γ isoform, or both Δ133p53β and Δ133p53γ isoforms are not detected; and
  c) treating said subject, wherein
  (i) if the subject is determined as being at a significant risk of cancer metastasis, an agent reducing Δ133p53β isoform, Δ133p53γ isoform, or both Δ133p53 and Δ133p53γ isoforms expression and an anticancer treatment is administered to the subject, or
  (ii) if the subject is determined as not being at a significant risk of cancer metastasis, an anticancer treatment is administered to the subject,
  wherein in step a) Δ133p53β isoform, Δ133p53γ isoform, or both Δ133p53 and Δ133p53γ isoforms are detected at nucleic acid level by measuring the amount of Δ133p53β isoform, Δ133p53γ isoform, or both Δ133p53β and Δ133p53γ isoforms mRNA or corresponding cDNA or at protein level,
  wherein the agent reducing Δ133p53β isoform, Δ133p53γ isoform, or both Δ133p53β and Δ133p53γ isoforms expression is antisense RNA or interfering RNA (iRNA).

7. The method according to claim 6, wherein in step a) Δ133p53β isoform, Δ133p53γ isoform, or both Δ133p53β and Δ133p53γ isoforms are detected by using q-RT-PCR.

8. The method according to claim 1, wherein the agent reducing Δ133p53β isoform, Δ133p53γ isoform, or both Δ133p53β and Δ133p53γ isoforms expression is selected from small interfering RNAs (siRNAs) and short hairpin RNAS (shRNAs).

9. The method according to claim 1, wherein the anticancer treatment is performed by a chemotherapeutic anticancer agent.

10. The method according to claim 9, wherein the chemotherapeutic anti-cancer agent is selected from topoisomerase II inhibitors, anti-tubuline agents, and antimetabolites.

11. A method for predicting a risk of cancer metastasis in a subject suffering from cancer from a cancer sample of said subject and treating said subject, comprising:
  a) detecting sphere-forming cancer cells expressing Δ133p53β isoform, Δ133p53γ isoform, or both Δ133p53β and Δ133p53γ isoforms in said cancer sample;
  b) concluding to the presence of a significant risk of cancer metastasis in said subject if sphere-forming cancer cells expressing Δ133p53β isoform, Δ133p53γ isoform, or both Δ133p53β and Δ133p53γ isoforms are detected and to the absence of a significant risk of cancer metastasis in said subject if sphere-forming cancer cells expressing Δ133p53β isoform, Δ133p53γ isoform, or both Δ133p53β and Δ133p53γ isoforms are not detected; and
  c) treating said subject, wherein
  (i) if the subject is determined as being at a significant risk of cancer metastasis, an agent reducing Δ133p53β isoform, Δ133p53γ isoform, or both Δ133p53 and Δ133p53γ isoforms expression and an anticancer treatment is administered to the subject, or
  (ii) if the subject is determined as not being at a significant risk of cancer metastasis, an anticancer treatment is administered to the subject,
  wherein the sphere-forming cancer cells expressing Δ133p53β isoform, Δ133p53γ isoform, or both Δ133p53β and Δ133p53γ isoforms in step a) are detected by performing an assay comprising the steps of:
  (i) resuspending cancer cells into a serum-free medium and plating them into tissue culture dishes, to which mammalian cells poorly adhere, at a seeding density between 250 and 2500 cells/cm$^2$;
  (ii) incubating the cancer cells during 7 to 15 days after the resuspending and plating in step (i);
  (iii) counting spheres that are at least 50 μm large; and
  (iv) measuring the expression of Δ133p53β isoform, Δ133p53γ isoform, or both Δ133p53β and Δ133p53γ isoforms in the spheres that are at least 50 μm large,
  wherein the resuspending of cancer cells in step (i) is performed in the presence of specific growth factors EGF and bFGF; the incubating of step (ii) is performed at 37° C. under 5% $CO_2$ atmosphere, and the counting in step (iii) is performed by a phase-contrast microscope.

* * * * *